(12) United States Patent
Montagne et al.

(10) Patent No.: US 8,609,666 B2
(45) Date of Patent: Dec. 17, 2013

(54) 2-MORPHOLINO-PYRIDO[3,2-D]PYRI-MIDINES

(75) Inventors: Cyril Montagne, Saint-Genis-Pouilly (FR); Agnés Bombrun, Chambesy (CH); Gwenaelle Desforges-Bouscary, Annemasse (FR); Anna Quattropani, Geneva (CH); Pascale Gaillard, Collonges-Sous-Saléve (FR)

(73) Assignee: Merck Serono SA, Coinsins, Vaud (CH)

(*) Notice: Subject to any disclaimer, the term of this patent is extended or adjusted under 35 U.S.C. 154(b) by 178 days.

(21) Appl. No.: 13/147,449

(22) PCT Filed: Feb. 4, 2010

(86) PCT No.: PCT/EP2010/051373
§ 371 (c)(1),
(2), (4) Date: Aug. 2, 2011

(87) PCT Pub. No.: WO2010/091996
PCT Pub. Date: Aug. 19, 2010

(65) Prior Publication Data
US 2011/0293564 A1 Dec. 1, 2011

Related U.S. Application Data

(60) Provisional application No. 61/207,744, filed on Feb. 17, 2009.

(30) Foreign Application Priority Data

Feb. 12, 2009 (EP) .................................... 09152709

(51) Int. Cl.
*A61K 31/519* (2006.01)
*C07D 471/04* (2006.01)

(52) U.S. Cl.
USPC ...................................... 514/258.1; 544/253

(58) Field of Classification Search
USPC ....................................... 544/253; 514/258.1
See application file for complete search history.

(56) References Cited

FOREIGN PATENT DOCUMENTS

| DE | 2117657 | 10/1972 | | |
|---|---|---|---|---|
| DE | 2202367 | 8/1973 | | |
| DE | 2208534 | 8/1973 | | |
| DE | 2208535 | 8/1973 | | |
| JP | 62221686 | 9/1987 | | |
| WO | WO 2006/090169 | 8/2006 | | |
| WO | WO-2006/090169 | * | 8/2006 | ........... A61K 31/519 |
| WO | WO 2008/023161 | 2/2008 | | |

OTHER PUBLICATIONS

Nishikawa, K, et al. "Structure-Activity Relationships of the Diuretic Activity of Triaza- and Tetraaza-naphthalene Compounds" *Chemical and Pharmaceutical Bulletin*, Jan. 1, 1976, pp. 2057-2077, vol. 24, No. 9.
Cantley, L. "The Phosphoinositide 3-Kinase Pathway" *Science*, May 31, 2002, pp. 1655-1657, vol. 296.
Fraser, J. D. et al. "Regulation of Interleukin-2 Gene Enhancer Activity by the T Cell Accessory Molecule CD28" *Science*, Jan. 18, 1991, pp. 313-316, vol. 251.
Fruman, D. A. et al. "Phosphoinositide Kinases" *Annual Review of Biochemistry*, 1998, pp. 481-507, vol. 67.
Gerard, C. et al. "Chemokines and disease" *Nature Immunology*, Feb. 2001, pp. 108-115, vol. 2, No. 2.
Jou, S. et al. "Essential, Nonredundant Role for the Phosphoinositide 3-Kinase p110δ in Signaling by the B-Cell Receptor Complex" *Molecular and Cellular Biology*, Dec. 2002, pp. 8580-8591, vol. 22, No. 24.
Laffargue, M. et al. "Phosphoinositide 3-Kinase γ Is an Essential Amplifier of Mast Cell Function" *Immunity*, Mar. 2002, pp. 441-451, vol. 16.
Lawlor, M. A. et al. "PKB/Akt: a key mediator of cell proliferation, survival and insulin responses?" *Journal of Cell Science*, 2001, pp. 2903-2910, vol. 114, No. 16.
Liebeskind, L. S. et al. "Heteroaromatic Thioether-Boronic Acid Cross-Coupling under Neutral Reaction Conditions" *Organic Letters*, 2002, pp. 979-981, vol. 4, No. 6.
Parker, P. J. "PI 3-kinase puts GTP on the Rac" *Current Biology*, 1995, pp. 577-579, vol. 5, No. 6.
Stein, R. C. et al. "PI3-kinase inhibition: a target for drug development?" *Molecular Medicine Today*, Sep. 2000, pp. 347-357, vol. 6.
Thelen, M. et al. "Wortmannin binds specifically to 1-phosphatidylinositol 3-kinase while inhibiting guanine nucleotide-binding protein-coupled receptor signaling in neutrophil leukocytes" *Proceedings of the National Academy of Sciences USA*, May 1994, pp. 4960-4964, vol. 91.
Theoharides, T. C. et al. "Critical role of mast cells in inflammatory diseases and the effect of acute stress" *Journal of Neuroimmunology*, 2004, pp. 1-12, vol. 146.
Toker, A. "Phosphoinositides and signal transduction" *Cellular and Molecular Life Sciences*, 2002, pp. 761-779, vol. 59.
Vanhaesebroeck, B. et al. "Synthesis and Function of 3-phosphorylated inositol Lipids" *Annual Review of Biochemistry*, 2001, pp. 535-602, vol. 70.
Vanhaesebroeck, B. et al. "Signalling by PI3K isoforms: insights from gene-targeted mice" *TRENDS in Biochemical Sciences*, Apr. 2005, pp. 194-204, vol. 30, No. 4.
Wymann, M. et al. "Lipids on the move: phosphoinositide 3-kinases in leukocyte function" *TRENDS Immunology Today*, Jun. 2000, pp. 260-264, vol. 21, No. 6.
Yao, R. et al. "Requirement for Phosphatidylinositol-3 Kinase in the Prevention of Apoptosis by Nerve Growth Factor" *Science*, Mar. 31, 1995, pp. 2003-2006, vol. 267.
Written Opinion in International Application No. PCT/EP2010/051373, Jun. 4, 2010, pp. 1-6.

* cited by examiner

*Primary Examiner* — Kamal Saeed
*Assistant Examiner* — Janet L Coppins
(74) *Attorney, Agent, or Firm* — Saliwanchik, Lloyd & Eisenschenk

(57) ABSTRACT

This invention relates to compounds of Formula (I) as Pi3k inhibitors for treating autoimmune diseases, inflammatory disorders, multiple sclerosis and other diseases like cancers.

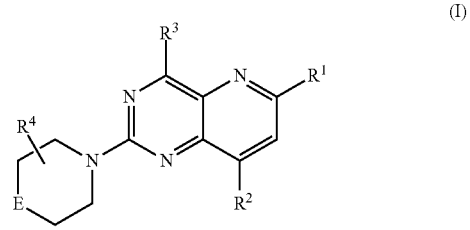

8 Claims, No Drawings

2-MORPHOLINO-PYRIDO[3,2-D]PYRIMIDINES

CROSS-REFERENCE TO RELATED APPLICATIONS

This application is the U.S. national stage application of International Patent Application No. PCT/EP2010/051373, filed Feb. 4, 2010, which claims the benefit of U.S. Provisional Patent Application No. 61/207,744, filed Feb. 17, 2009.

The invention relates to compounds of formula (I) and related formulae, their use as medicament and their use for treating autoimmune diseases, inflammatory disorders, multiple sclerosis and other diseases like cancers.

BACKGROUND OF THE INVENTION

Phosphoinositide 3-kinases (PI3Ks) have a critical signalling role in cell proliferation, cell survival, vascularization, membrane trafficking, glucose transport, neurite outgrowth, membrane ruffling, superoxide production, actin reorganization and chemotaxis (Cantley, 2000, Science, 296, 1655-1657).

The term PI3K is given to a family of lipid kinases which, in mammals, consists in eight identified PI3Ks that are divided into three sub-families according to their structure and their substrate specificity.

Class I group of PI3Ks consists in two sub-groups, Class IA and Class IB.

Class IA are a family of heterodimeric lipid kinases consisting in a 85 kDa regulatory unit (responsible for protein-protein interactions via the interaction of Src homology 2 (SH2) domain with phosphotyrosine residues of other proteins) and a catalytic sub-unit of 110 kDa that generate second messenger signals downstream of tyrosine kinases, thereby controlling cell metabolism, growth, proliferation, differentiation, motility and survival. Three catalytic forms (p110α, p110β and p110δ) and five regulatory isoforms (p85α, p85β, p55γ, p55α and p50α) exist for this class.

Class IB are stimulated by G protein bg sub-units of heterodimeric G proteins. The only characterized member of Class IB is PI3Kγ (p110γ catalytic sub-unit complex with a 101-kDa regulatory protein, p101).

Class 1A PI3Ks comprises α, β and γ isoforms, which are approximately of 170 kDa and characterized by the presence of a C-terminal C2 domain.

Class III PI3Ks includes the phosphatidylinositol specific 3-kinases.

The evolutionary conserved isoforms p110α and β are ubiquitously expressed, while δ and γ are more specifically expressed in the haematopoetic cell system, smooth muscle cells, myocytes and endothelial cells (Vanhaesebroeck et al., 2001, Annu. Rev. Biochem., 70, 535-602). Their expression might also be regulated in an inducible manner depending on the cellular-, tissue type and stimuli as well as disease context.

PI3Ks are enzymes involved in phospholipid signalling and are activated in response to a variety of extra-cellular signals such as growth factors, mitogens, integrins (cell-cell interactions) hormones, cytokines, viruses and neurotransmitters and also by intra-cellular cross regulation by other signalling molecules (cross-talk, where the original signal can activate some parallel pathways that in a second step transmit signals to PI3Ks by intra-cellular signalling events), such as small GTPases, kinases or phosphatases for example. Phosphatidylinositol (PtdIns) is the basic building block for the intracellular inositol lipids in eukaryotic cells, consisting of D-myo-inositol-1-phosphate (Ins1P) linked via its phosphate group to diacylglycerol. The inositol head group of PtdIns has five free hydroxy groups and three of these are found to be phosphorylated in cells in different combinations. PtdIns and its phosphorylated derivatives are collectively referred as inositol phospholipids or phosphoinositides (PIs). Eight PI species have been documented in eukaryotic cells (Vanhaesebroeck et al., 2001, above). PIs all reside in membranes and are substrates for kinases, phosphatases and lipases.

In vitro, PI3Ks phosphorylate the 3-hydroxyl group of the inositol ring in three different substrates: phosphatidylinositol (PtdIns), phosphatidylinositol-4-phosphate (PI(4)P) and phosphatidylinositol-4,5-biphosphate (PI(4,5)P2), respectively generating three lipid products, namely phosphatidylinositol 3-monophosphate (PI(3)P), phosphatidylinositol 3,4-bisphosphate (PI(3,4)P2) and phosphatidylinositol 3,4,5-trisphosphate (PI(3,4,5)P3.

The preferred substrate for Class I PI3Ks is PI(4,5)P2. Class II PIKs have a strong preference for PtdIns as substrate over PI(4)P and PI(4,5)P2. Class III PI3Ks can only use PtdIns as substrate in vivo and are likely to be responsible for the generation of most PI(3)P in cells (Vanhaesebroeck et al., 2001, above).

The phosphoinositides intracellular signalling pathway begins with the binding of a signalling molecule (extracellular ligands, stimuli, receptor dimidiation, transactivation by heterologous receptor (e.g. receptor tyrosine kinase)) to a G-protein linked transmembrane receptor integrated into the plasma membrane resulting in the activation of PI3Ks.

Once activated, PI3Ks convert the membrane phospholipid PI(4,5)P2 into PI(3,4,5)P3 which in turn can be further converted into another 3' phosphorylated form of phosphoinositides by 5'-specific phosphoinositide phosphatases, thus PI3K enzymatic activity results either directly or indirectly in the generation of two 3'-phosphoinositide sub-types that function as second messengers in intra-cellular signal transduction (Toker et al., 2002, Cell Mol. Life. Sci. 59(5) 761-79).

The role as second messengers of phosphorylated products of PtdIns act is involved in a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Stein, 2000, Mol. Med. Today 6(9) 347-57). Chemotaxis—the directed movement of cells toward a concentration gradient of chemical attractants, also called chemokines is involved in many important diseases such as inflammation/auto-immunity, neurodegeneration, angiogenesis, invasion/metastasis and wound healing (Wyman et al., 2000, Immunol Today 21(6) 260-4 and Gerard et al., 2001, Nat. Immunol. 2(2) 108-15).

PI3-kinase activation, is therefore believed to be involved in a range of cellular responses including cell growth, differentiation, migration and apoptosis (Parker et al., 1995, Current Biology, 5, 577-99; Yao et al., 1995, Science, 267, 2003-05).

Recent biochemical studies revealed that, Class I PI3Ks (e.g. Class IB isoform PI3Kγ) are dual-specific kinase enzymes, i.e. they display both lipid kinase activity (phosphorylation of phospho-inositides) as well as protein kinase activity, as they are able to induce the phosphorylation of other protein as substrates, including auto-phosphorylation as intra-molecular regulatory mechanism.

PI3Ks appear to be involved in a number of aspects of leukocyte activation. A p85-associated PI3-kinase activity has been shown to physically associate with the cytoplasmic domain of CD28, which is an important co-stimulatory molecule for the activation of T-cells in response to antigen.

These effects are linked to increases in the transcription of a number of genes including interleukin-2 (IL-2), an important T cell growth factor (Fraser et al., 1991, Science, 251, 313-16). Mutation of CD28 such that it can longer interact with PI3-kinase leads to a failure to initiate IL-2 production, suggesting a critical role for PI3-kinase in T cell activation.

Cellular processes in which PI3Ks play an essential role include suppression of apoptosis, reorganization of the actin skeleton, cardiac myocyte growth, glycogen synthase stimulation by insulin, TNFa-mediated neutrophil priming and superoxide generation, and leukocyte migration and adhesion to endothelial cells.

It has been described that PI3Kγ relays inflammatory signals through various G(i)-coupled receptors (Laffargue et al., 2002, Immunity 16(3)-441-51) and its central to mast cell function, stimuli in context of leukocytes, immunology includes cytokines, chemokines, adenosines, antibodies, integrins, aggregation factors, growth factors, viruses or hormones for example (Lawlor et al., 2001, J. Cell. Sci., 114 (Pt 16) 2903-10).

Two compounds, LY294002 and Wortmannin (cf. hereinafter), have been widely used as PI3-kinase inhibitors. These compounds are non-specific PI3K inhibitors, as they do not distinguish among the four members of Class I PI3-kinases.

IC50 values of Wortmannin against each of the various Class I PI3-kinases are in the range of 1-10 nM and IC50 values for LY294002 against each of these PI3-kinases are about 15-20 μM (Fruman et al., 1998, Ann. Rev. Biochem., 67, 481-507), also 5-10 μM on CK2 protein kinase and some inhibitory activity on phospholipases.

Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor (Thelen et al., 1994, Proc. Natl. Acad. Sci. USA, 91, 4960-64). Experiments with wortmannin, show that PI3K activity in cells of hematopoietic lineage, particularly neutrophils, monocytes, and other types of leukocytes, is involved in many of the non-memory immune response associated with acute and chronic inflammation.

Based on studies using Wortmannin, there is evidence that PI3-kinase function is also required for some aspects of leukocyte signalling through G-protein coupled receptors (Thelen et al., 1994, above). Moreover, it has been shown that Wortmannin and LY294002 block neutrophil migration and superoxide release.

Some results have indicated that PI3K inhibitors, for example, LY294002, can increase the in vivo antitumor activity of certain cytotoxic agents (e.g. paclitaxel) (Grant, 2003, Current Drugs, 6(10), 946-948).

However, in as much as these compounds do not distinguish among the various isoforms of PI3K, it remains unclear which particular PI3K isoform or isoforms are involved in these phenomena. Specific inhibitors against individual members of a family of enzymes provide valuable tools for deciphering functions of each enzyme as depending on the disease application, varying the degree of selectivity for PI3K isoforms can be of interest. p110 δ is expressed predominantly in cells of hemopoeitic origin such as leukocytes. To assess the role of the d isoform of the p110 catalytic subunit of PI3Ks, PI3Kδ-null mice have been recently developed (Jou et al., 2002, Molecular and Cellular biology, 22(4), 8580-8591) and their specific immunological phenotype has been well characterized (Vanhaesebroeck et al., 2005, Trends in Biochemical Sciences, 30(4), 194-204). These experiments show that the PI3Kδ-null animals are viable and that a deficiency in PI3Kδ results in a very specific loss of the function of the B-cell antigen specific receptor complex, while signalling through the cytokine receptor complexes is unaffected (Jou et al., 2002, above).

It has been also shown that the inactivation of the p110δ isoform of PI3K in mast cells leads to defective stem cell factor-mediated in vitro proliferation, adhesion and migration and to impaired allergen-IgE-induced degranulation and cytokine release. Inactivation of p110δ protects mice against anaphylactic allergic responses, suggesting p110δ as a target for therapeutic intervention in allergy and mast-cell-related pathologies (Ali. et al., 2004, Nature, 431, 1007-1010).

Mast cells have emerged as a unique immune cell that could participate in a variety of inflammatory diseases in the nervous system (e.g. multiple sclerosis), skin, joints as well as cardiopulmonary, intestinal and urinary systems (Theoharides et al., 2004, J. of Neuroimmunology, 146, 1-12).

The high relevance of the PI3K pathway in some widely spread diseases stresses the need to develop inhibitors, including selective inhibitors, of PI3K isozymes, in order that the functions of each isozyme can be better characterized.

Recently, PI3K inhibitors have been developed: thiazole derivatives (WO 2005/021519; and WO 04/078754), thiazolidine derivatives (WO 2004/007491 and WO 2004/056820) and Quinazolinones derivatives (WO 03/035075).

Pyrido[3,2-d]pyrimidine derivatives with particular substitution pattern have been studied. EP 1277738 describes 4-morpholino-pyrido[3,2-d]pyrimidine derivatives substituted in positions 2, 6 and 7, involved in the Pi3K inhibition for the treatment of cancer. No indication is provided regarding the selectivity of these compounds. WO2008/023161 provides methylmorpholino pyrido[3,2-d]pyrimidine derivatives as MTOR inhibitors. The patent WO2006/069805 discloses pyrido[3,2-d]pyrimidine derivatives substituted in position 2, 4, 6 and/or 7 for the treatment of disorder of central nervous system and autoimmune disorder. WO 2006/087229 provide 2, 4, 6-trisubstituted pyrido[3,2-d]pyrimidine derivatives active against autoimmune and central nervous system disorders and cardiovascular diseases. Other various pyrido [3,2-d]pyrimidine derivatives are disclosed in WO2008/009076, WO2008/077651 and WO 2009/003669.

The present invention provides morpholino pyrido[3,2-d] pyrimidine derivatives substituted in position 2, 6 and 8, and used as Pi3K modulators.

SUMMARY OF THE INVENTION

According to one aspect of the invention, are provided pyridopyrimidine compounds. According to another aspect of the invention, are provided pyrimidopyrimidine compounds which are suitable for the treatment and/or prevention of disorders related to phosphoinositide-3-kinases, PI3Ks, such as PI3K alpha or PI3K gamma or PI3K delta or PI3K beta.

According to another aspect of the invention, are provided pyridopyrimidine compounds, which are able to modulate, especially inhibit the activity or function of phosphoinositide-3-kinases, PI3Ks in disease states in mammals, especially in humans.

According to another aspect of the invention, are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect of the invention is provided a kit or a set comprising at least one compound of Formula (I), preferably in combination with immunomodulating agents. Alternatively, the kit consists of separate packs of:

(a) an effective amount of a compound of the formula (I) and/or pharmaceutically usable derivatives, solvates and stereoisomers thereof, including mixtures thereof in all ratios, and (b) an effective amount of a further medicament active ingredient.

According to another aspect of the invention, is provided a process for the synthesis of pyridopyrimidine compounds.

DETAILED DESCRIPTION OF THE INVENTION

In one embodiment, the invention provides compounds of Formula (I):

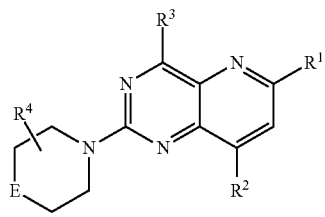

(I)

Wherein
R$^1$ denotes perfluoroalkyl, —NH$_2$, —NA$_2$, A*, —NH-A, —NH—(CH$_2$)$_p$-A, —SO-A, SO$_2$-A, —COOR$^T$, —(CH$_2$)$_p$—OR$^T$, —(CH$_2$)$_p$—SR$^T$, —COA, —CO-Het, —CO—N(H)$_{2-m}$(A)$_m$; —SO—N(H)$_{2-m}$(A)$_m$, SO$_2$—N(H)$_{2-m}$(A)$_m$, N(H)$_{1-q}$A$_q$SOA, N(H)$_{1-q}$A$_q$SO$_2$A, —(CH$_2$)$_p$—N(H)$_{2-m}$(A)$_m$, —CO—NH—(CH$_2$)$_p$—N(H)$_{2-m}$(A)$_m$, —(CH$_2$)$_p$—NH—(CH$_2$)$_p$—N(H)$_{2-m}$(A)$_m$, Ar*, Het R$^2$ denotes H, Hal, CF$_3$, A, Ar, Het, SA, OA, OH, —SOA, —SO$_2$A, —OCO-A, —N(H)$_{2-m}$(A)$_m$, —NH—(CH$_2$)$_p$—N(H)$_{2-m}$(A)$_m$, —NA-(CH$_2$)$_p$—N(H)$_{2-m}$(A)$_m$, —NA-(CH$_2$)$_p$—OR$^T$, —NH—(CH$_2$)$_p$—OA, —(CH$_2$)$_p$Het, —(CH$_2$)$_p$—N(H)$_{2-m}$(A)$_m$, —O(CH$_2$)$_p$OR$^T$, —N(R$^T$)$_2$, E denotes O, S, CHR$^T$, NR$^T$, R$^3$ denotes Ar, Het, R$^4$ denotes H, perfluoroalkyl, —NH$_2$, —NA$_2$, A, —NH-A, —NH—(CH$_2$)$_p$-A, —SO-A, SO$_2$-A, —COOR$^T$, —(CH$_2$)$_p$—OR$^T$, —(CH$_2$)$_p$—SR$^T$, —COA, —CO-Het, —CO—N(H)$_{2-m}$(A)$_m$; —SO—N(H)$_{2-m}$(A)$_m$, SO$_2$—N(H)$_{2-m}$(A)$_m$, N(H)$_{1-q}$A$_q$SOA, N(H)$_{1-q}$A$_q$SO$_2$A, —(CH$_2$)$_p$—N(H)$_{2-m}$(A)$_m$, —CO—NH—(CH$_2$)$_p$—N(H)$_{2-m}$(A)$_m$, —(CH$_2$)$_p$—NH—(CH$_2$)$_p$—N(H)$_{2-m}$(A)$_m$, Ar, Het R$^T$ denotes H, A, Ar, Het, Ar denotes a monocyclic or bicyclic, aromatic carbocyclic ring having 6 to 14 carbon atoms, which is unsubstituted or monosubstituted, disubstituted or trisubstituted by, Hal, CF$_3$, OCF$_3$, NO$_2$, CN, perfluoroalkyl, A, OA, OH, NH$_2$, COH, CONH$_2$, —NHCOA, —NHSO$_2$A, —NHSO$_2$—N(H)$_{2-m}$(A)$_m$, N(H)$_{1-q}$A$_q$COA, N(H)$_{1-q}$A$_q$SO$_2$—N(H)$_{2-m}$(A)$_m$, —N(H)$_{1-q}$A$_q$CON(H)$_{2-m}$(A)$_m$, —COOA, —SO$_2$A, —SO$_2$N(H)$_{2-m}$(A)$_m$, —SO$_2$Het, —(CH$_2$)$_p$—N(H)$_{2-m}$(A)$_m$, —(CH$_2$)$_p$—OR$^T$, or disubstituted or trisubstituted by OH and 1 or 2 of above described substituents.

Ar* denotes a monocyclic or bicyclic, aromatic carbocyclic ring having 6 to 14 carbon atoms, which is monosubstituted, disubstituted or trisubstituted by, Hal, CF$_3$, OCF$_3$, NO$_2$, CN, perfluoroalkyl, A, OA, OH, NH$_2$, COH, CONH$_2$, —NHCOA, —NHSO$_2$A, —NHSO$_2$—N(H)$_{2-m}$(A)$_m$, N(H)$_{1-q}$A$_q$COA, N(H)$_{1-q}$A$_q$SO$_2$—N(H)$_{2-m}$(A)$_m$, —N(H)$_{1-q}$A$_q$CON(H)$_{2-m}$(A)$_m$, —COOA, —SO$_2$A, —SO$_2$N(H)$_{2-m}$(A)$_m$, —SO$_2$Het, —(CH$_2$)$_p$—N(H)$_{2-m}$(A)$_m$, —(CH$_2$)$_p$—OR$^T$, or disubstituted or trisubstituted by OH and 1 or 2 of above described substituents.

Het denotes a monocyclic or bicyclic saturated, unsaturated or aromatic heterocyclic ring having 1, 2, 3 or 4 N, O and/or S atoms which is unsubstituted or monosubstituted, disubstituted or trisubstituted by alkyl having 1 to 8 carbon atoms, alkoxy having 1 to 8 carbon atoms, Hal, CF$_3$, OCF$_3$, NO$_2$, CN, perfluoroalkyl, A, OA, OH, NH$_2$, COH, CONH$_2$, —NHCOA, —NHSO$_2$A, —NHSO$_2$—N(H)$_{2-m}$(A)$_m$, N(H)$_{1-q}$A$_q$COA, N(H)$_{1-q}$A$_q$SO$_2$—N(H)$_{2-m}$(A)$_m$, —N(H)$_{1-q}$A$_q$CON(H)$_{2-m}$(A)$_m$, —COOA, —SO$_2$A, —SO$_2$N(H)$_{2-m}$(A)$_m$, —SO$_2$Het, —(CH$_2$)$_p$—N(H)$_{2-m}$(A)$_m$, —(CH$_2$)$_p$—OR$^T$, m denotes 0, 1 or 2;

p denotes 0, 1, 2, 3 or 4;

q denotes 0 or 1;

A is a branched or linear alkyl having 1 to 12 C-atoms, wherein one or more, preferably 1 to 7 H-atoms may be replaced by Hal, Ar, Het, OR$^6$, —CN, —COOalkyl or N(R$^6$)$_2$ and wherein one or more, preferably 1 to 7 non-adjacent CH$_2$-groups may be replaced by O, NR$^6$ or S and/or by —CH=CH— or —C≡C— groups, or denotes cycloalkyl or cycloalkylalkylen having 3-7 ring C atoms;

A* is a branched or linear alkyl having 2 to 12 C-atoms, wherein one or more, preferably 1 to 7 H-atoms may be replaced by Hal, Ar, Het, OR$^6$, —CN, —COOalkyl or N(R$^6$)$_2$ and wherein one or more, preferably 1 to 7 non-adjacent CH$_2$-groups may be replaced by O, NR$^6$ or S and/or by —CH=CH— or —C≡C— groups, or denotes cycloalkyl or cycloalkylalkylen having 3-7 ring C atoms;

R$^6$ is H, A, —(CH$_2$)$_p$—N(H)$_{2-m}$(A)$_m$, —(CH$_2$)$_p$—OA; CH$_2$NH$_2$, and pharmaceutically acceptable derivatives, solvates, tautomers, salts and stereoisomers thereof, including mixtures thereof in all ratios.

In a second embodiment, the invention relates to compounds of formulae (I')

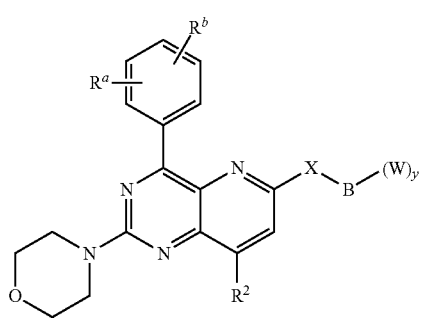

(I')

Wherein
R² is as defined above
X denotes CO, CS, or CH₂,
B denotes O, N, S, SO, SO₂ or a bond,
W denotes H, A, —(CH₂)$_p$—N(H)$_{2-m}$(A)$_m$, —(CH₂)—OA;
y is 1 or 2
R$^a$, R$^b$ denote independently from one another H, OH, OA, Hal, —(CH₂)$_p$OH, —(CH₂)$_p$OA, —(CH₂)$_p$—N(H)$_{2-m}$(A)$_m$,
wherein m, p, and A are as defined above.
and pharmaceutically acceptable derivatives, solvates, tautomers, salts and stereoisomers thereof, including mixtures thereof in all ratios.
In another embodiment, the invention relates to the compounds of formula (I″),

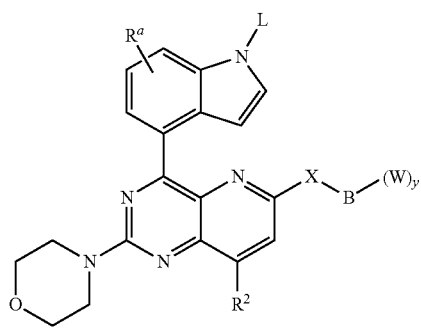

(I″)

Wherein
R², R$^a$, X, B, W, and y are as defined above
And L denotes H, or A,
wherein A is as above defined,
and pharmaceutically acceptable derivatives, solvates, tautomers, salts and stereoisomers thereof, including mixtures thereof in all ratios.
In another embodiment, the invention relates to compounds of Formula (I‴):

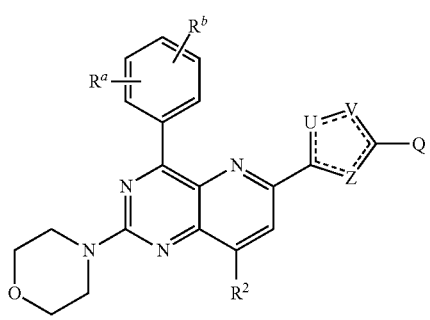

(I‴)

Wherein R², R$^a$ and R$^b$ are as defined above,
U, V and Z are independently of one another CH, O, S or N
---- is a single or a double bond
Q is H, Hal, CF₃, (C₁-C₈)alkyl, SA, OA, OH, —SOA, —SO₂A, —OCO-A, —N(H)$_{2-m}$(A)$_m$, —NH—(CH₂)$_p$—N(H)$_{2-m}$(A)$_m$, —NA-(CH₂)$_p$—OR$^T$, —NH—(CH₂)$_p$—OA, —(CH₂)$_p$Het, —(CH₂)$_p$—OR$^T$, —(CH₂)$_p$—NR$^T$,
Wherein R$^T$, A, m and p are as above defined,
and pharmaceutically acceptable derivatives, solvates, tautomers, salts and stereoisomers thereof, including mixtures thereof in all ratios.
Above and below, Me refers to a methyl group, Et refers to an ethyl group.

The formula (I) and related formulae also encompasses mixtures of the compounds of the formula (I), for example mixtures of two diastereomers, for example in the ratio 1:1, 1:2, 1:3, 1:4, 1:5, 1:10, 1:100 or 1:1000.
These are particularly preferably mixtures of stereoisomeric compounds.
"Alkyl" denotes a carbon chain having 1, 2, 3, 4, 5, 6, 7, 8, 9, 10, 11, or 12 carbon atoms. Alkyl preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl, pentafluoroethyl or 1,1,1-trifluoroethyl.
"Cycloalkyl" or "Cycloalkyl groups" denotes a cyclic alkyl containing 3 to 12 carbon atoms. Cycloalkyl preferably denotes cyclopropyl, cyclobutyl, cyclopentyl, cyclohexyl or cycloheptyl.
"Cycloalkylalkylene" or "cycloalkylalylen group" denotes a cycloalkyl group bond to the rest of the molecule via a carbon chain and having 1, 2, 3, 4, 5, 6, 7, 8, 9, 10, 11, 12, 13, 14, 15, 16, 17, or 18 carbon atoms. Cycloalkylalkylene preferably denotes cyclopropylmethylene, cyclobutylmethylene, cyclopentylmethylene, cyclohexylmethylene or cycloheptylmethylene.
"Alkylene" or "alkylene group" is a bivalent carbon chain having 1, 2, 3, 4, 5, 6, 7, 8, 9, 10, 11, or 12 carbon atoms. Alkylene is preferably methylene, ethylene, propylene, butylene, pentylene or hexylene, furthermore branched alkylene.
"Perfluoroalkyl" denotes an alkyl chain having 1, 2, 3, 4, 5, 6, 7, 8, 9, 10, 11, or 12 carbon atoms and wherein all the hydrogen atoms are replaced by F atoms, preferably denotes CF₃.
"Fluoroalkyl" denotes an alkyl chain having 1, 2, 3, 4, 5, 6, 7, 8, 9, 10, 11, or 12 carbon atoms and wherein one or more of the hydrogen atoms are replaced by F atoms.
Hal denotes Cl, Br, I, F and preferably F, Cl or Br.
"Alkoxy" or "alkoxy group" is branched or linear and preferably denotes a group —O—(CH₂)$_p$—CH₃ wherein p is as above defined. Most preferably alkoxy is Methoxy or Ethoxy.
"Carboxy" or "carboxy group" denotes a group —COOH.
"Hydroxy" or hydroxyl group" denotes an —OH group.
"Carboxyalkyl" denotes an ester group, preferably an alkyl ester, such as COOMe or COOEt.
"Sulfonyl" or "sulfonyl group" denotes a group —SO₂—.
"Alkylsulfonyl" denotes a group —SO₂-alkyl, preferably methylsulfonyl or ethylsulfonyl.
"Acyl" denotes a group —C(O)R, wherein R can be A, Ar, Het as defined above. Preferably Acyl denotes acetyl (—C(O)CH₃).
"Amino" or "amino group" denotes the group —NR'R" where each R', R" is independently hydrogen, (C₁-C₈)alkyl, Ar, Het or A. R' and R", together with the nitrogen atom to which they are attached, can optionally form a Het group. R' and R", together with the nitrogen atom to which they are attached, preferably form a 5-membered unsaturated or aromatic heterocyclic ring having 1, 2, 3, 4, heteroatoms selected in the group of N, O, and S.
"Alkylamine" denotes the group —(CH₂)$_p$—NR'R" wherein each R', R" is independently hydrogen, alkyl, Ar, Het or A, and wherein p is as defined above. R and R', together with the nitrogen atom to which they are attached, can optionally foun a Het group. R' and R", together with the nitrogen atom to which they are attached; preferably form a 5-membered unsaturated or aromatic heterocyclic ring having 1, 2, 3, 4, heteroatoms selected in the group of N, O, and S.

"Amido" refers to the group —C(O)NR'R" where each R', R" is independently hydrogen, alkyl, Ar, Het or A, and where R' and R", together with the nitrogen atom to which they are attached, can optionally form a Het group. R' and R", together with the nitrogen atom to which they are attached; preferably form a 5-membered unsaturated or aromatic heterocyclic ring having 1, 2, 3, 4, heteroatoms selected in the group of N, O, and S.

Ar denotes preferably a monocyclic or bicyclic, aromatic carbocyclic ring having 6 to 14 carbon atoms, which is unsubstituted or monosubstituted, disubstituted or trisubstituted by alkyl having 1 to 8 carbon atoms, alkoxy having 1 to 8 carbon atoms, Hal, $CF_3$, $OCF_3$, $NO_2$, CN, perfluoroalkyl, A, OA, amino, $CONH_2$, —NHCOA, —NHSO$_2$—N(H)$_{2-m}$(A)$_m$, COOA, —SO$_2$A, —SO$_2$N(H)$_{2-m}$(A)$_m$, —SO$_2$Het.

More particularly, Ar is unsubstituted or:

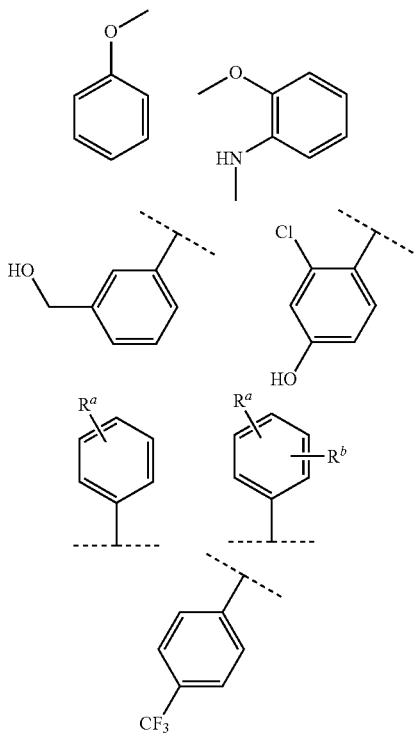

wherein $R^a$ and $R^b$ denote independently from each other Ar, Het, OA or A. $R^a$ preferably denotes OA, —SO$_2$NHA, —SO$_2$N(H)$_{2-m}$(A)$_m$, NHSO$_2$A, or —SO$_2$-A, NHA, and $R^b$ is preferably —CH$_2$OH, F, C$_1$ or CF$_3$.

In another preferred embodiment, $R^a$ is selected from the groups consisting of OA or CH$_2$OH, and $R^b$ is selected from the groups consisting of F, Cl or CF$_3$.

Very particularly, compounds of formula (I) are the more preferred, the more preferred substituents they carry.

Het preferably denotes monocyclic or bicyclic saturated, unsaturated or aromatic heterocyclic ring having 1 or 2 N and/or O atoms which is unsubstituted or monosubstituted, disubstituted or trisubstituted by alkyl having 1 to 8 carbon atoms, alkoxy having 1 to 8 carbon atoms, Hal, $CF_3$, $OCF_3$, $NO_2$, CN, perfluoroalkyl, A, OA, OH, NH$_2$, COH, CONH$_2$, —NHCOA, —NHSO$_2$A, —NHSO$_2$—N(H)$_{2-m}$(A)$_m$, N(H)$_{1-q}$A$_q$COA, N(H)$_{1-q}$A$_q$SO$_2$—N(H)$_{2-m}$(A)$_m$, —N(H)$_{1-q}$A$_q$CON(H)$_{2-m}$(A)$_m$, —COOA, —SO$_2$A, —SO$_2$N(H)$_{2-m}$(A)$_m$, —SO$_2$Het, —(CH$_2$)$_p$—N(H)$_{2-m}$(A)$_m$, —(CH$_2$)$_p$—OR$^T$, Het most preferably denotes one of the following groups:

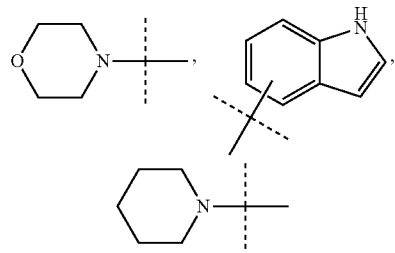

In a preferred embodiment, the invention provides compounds of Formula (I) wherein $R^2$ denotes one of the following groups:

H, Cl, -Me, —NMe(CH$_2$)$_2$OMe, —NMe(CH$_2$)$_2$OH, —NH(CH$_2$)$_2$OMe, —NH(CH$_2$)$_2$OH, —N(Me)$_2$, —NHMe, —O(CH$_2$)$_2$OMe, —NMe(CH$_2$)$_2$NMe$_2$, SO$_2$Me, methoxyphenyl or one of the following groups:

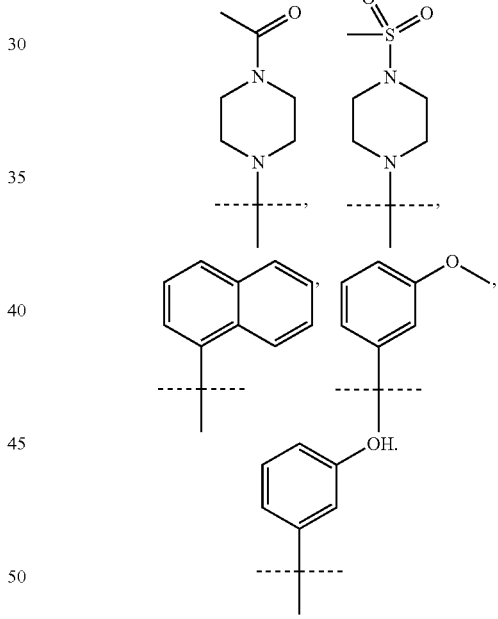

In a preferred embodiment, $R^3$ denotes one of the following groups:

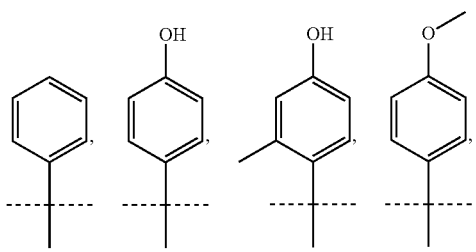

-continued
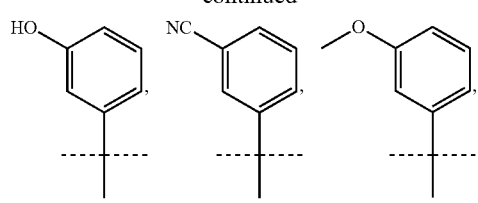
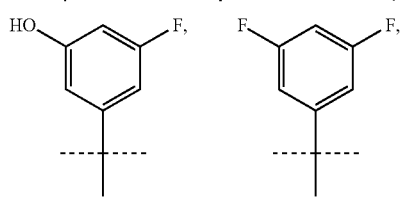
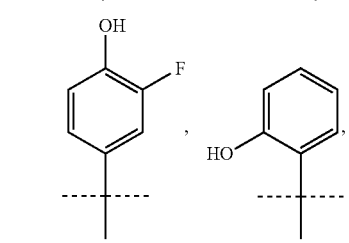
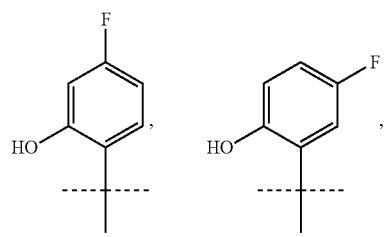
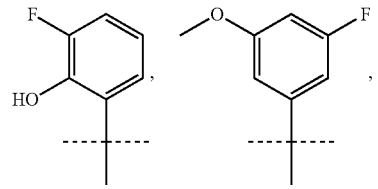
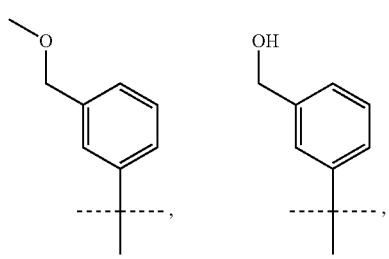
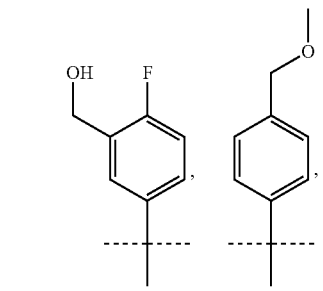
-continued
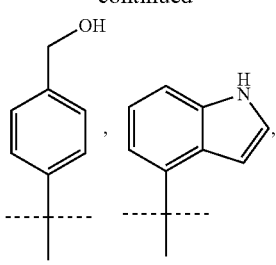
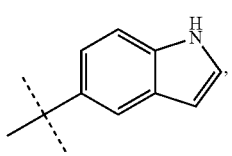
In another preferred embodiment, $R^1$ denotes $COOR^T$ wherein $R^T$ is as defined above. Alternatively, $R^1$ also denotes H, A or Ar.
Most preferably, the invention relates to compounds of Formula (I) selected from the following group:
| Example No | structures |
|---|---|
| 1 | 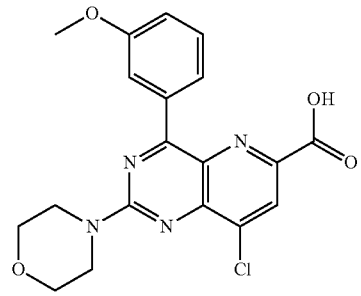 [SMILES: COc1cccc(-c2nc(N3CCOCC3)nc3c(Cl)cc(C(=O)O)nc23)c1] |
| 2 | 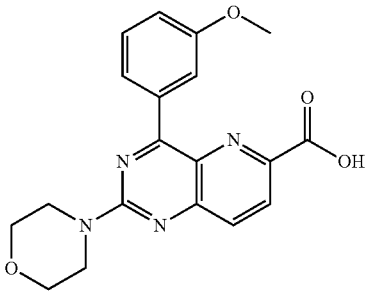 [SMILES: COc1cccc(-c2nc(N3CCOCC3)nc3ccc(C(=O)O)nc23)c1] |

-continued

| Example No | structures |
|---|---|
| 3 | (structure: 4-(4-hydroxyphenyl)-2-morpholino-8-[methyl(2-methoxyethyl)amino]pyrido[3,2-d]pyrimidine-6-carboxylic acid) |
| 4 | (structure: 4-(4-hydroxyphenyl)-2-morpholino-8-(dimethylamino)pyrido[3,2-d]pyrimidine-6-carboxylic acid) |
| 5 | (structure: 4-(4-hydroxyphenyl)-2-morpholino-8-[(2-methoxyethyl)amino]pyrido[3,2-d]pyrimidine-6-carboxylic acid) |

-continued

| Example No | structures |
|---|---|
| 6 | (structure: 4-(4-hydroxyphenyl)-2-morpholino-8-(2-methoxyethoxy)pyrido[3,2-d]pyrimidine-6-carboxylic acid) |
| 7 | (structure: 4-(4-hydroxyphenyl)-2-morpholino-8-[(2-hydroxyethyl)amino]pyrido[3,2-d]pyrimidine-6-carboxylic acid) |
| 8 | (structure: 4-(4-hydroxyphenyl)-2-morpholinopyrido[3,2-d]pyrimidine-6-carboxylic acid) |
| 9 | (structure: 4-(3-hydroxyphenyl)-2-morpholino-8-chloropyrido[3,2-d]pyrimidine-6-carboxylic acid) |

| Example No | structures |
|---|---|
| 10 | 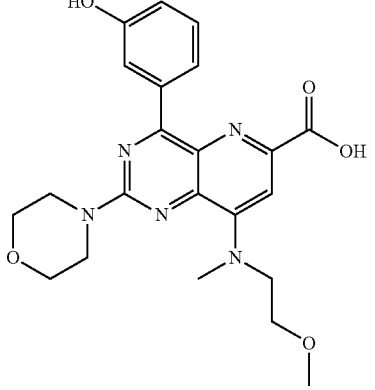 |
| 11 | 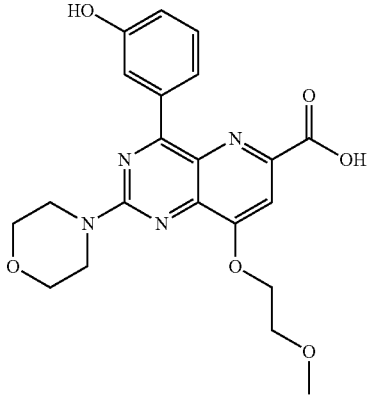 [SMILES: COCCOc1cc(C(=O)O)nc2c(-c3cccc(O)c3)nc(N3CCOCC3)nc12] |
| 12 | 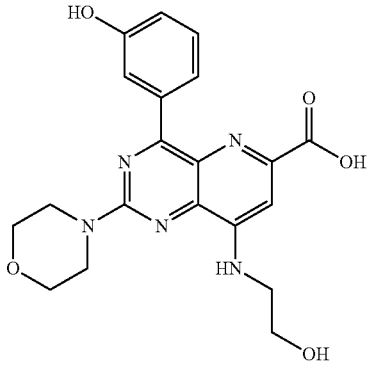 [SMILES: O=C(O)c1cc(NCCO)c2nc(N3CCOCC3)nc(-c3cccc(O)c3)c2n1] |
| 13 | 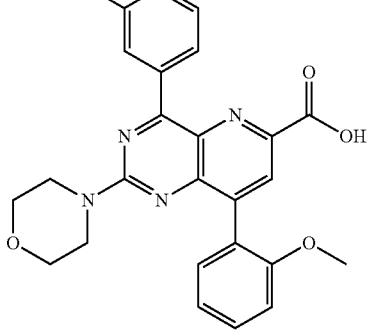 |
| 14 | 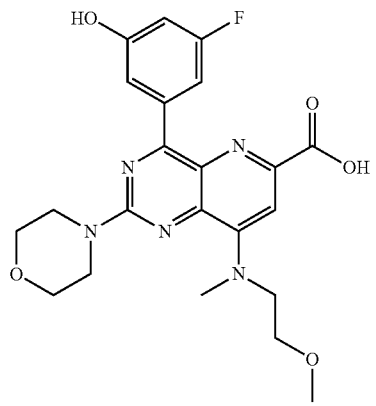 [SMILES: COCCN(C)c1cc(C(=O)O)nc2c(-c3cc(O)cc(F)c3)nc(N3CCOCC3)nc12] |
| 15 | 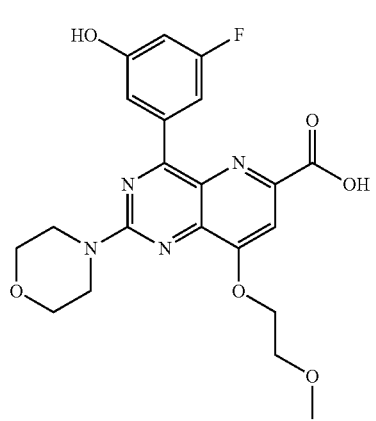 [SMILES: COCCOc1cc(C(=O)O)nc2c(-c3cc(O)cc(F)c3)nc(N3CCOCC3)nc12] |
| 16 | 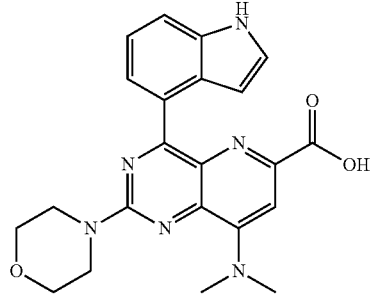 [SMILES: CN(C)c1cc(C(=O)O)nc2c(-c3cccc4[nH]ccc34)nc(N3CCOCC3)nc12] |
| 17 | |

-continued

| Example No | structures |
|---|---|
| 18 | 4-(1H-indol-4-yl)-2-morpholino-8-(methylamino)pyrido[3,2-d]pyrimidine-6-carboxylic acid |
| 19 | 4-(1H-indol-4-yl)-2-morpholino-8-((2-methoxyethyl)amino)pyrido[3,2-d]pyrimidine-6-carboxylic acid |
| 20 | 4-(1H-indol-4-yl)-2-morpholino-8-((2-hydroxyethyl)(methyl)amino)pyrido[3,2-d]pyrimidine-6-carboxylic acid |
| 21 | 4-(1H-indol-5-yl)-2-morpholino-8-((2-methoxyethyl)(methyl)amino)pyrido[3,2-d]pyrimidine-6-carboxylic acid |

-continued

| Example No | structures |
|---|---|
| 22 | 4-(4-(hydroxymethyl)phenyl)-2-morpholino-8-((2-methoxyethyl)(methyl)amino)pyrido[3,2-d]pyrimidine-6-carboxylic acid |
| 23 | 4-(3-(hydroxymethyl)phenyl)-2-morpholino-8-(dimethylamino)pyrido[3,2-d]pyrimidine-6-carboxylic acid |
| 24 | 4-(3-(hydroxymethyl)phenyl)-2-morpholino-8-((2-hydroxyethyl)(methyl)amino)pyrido[3,2-d]pyrimidine-6-carboxylic acid |
| 25 | 4-(3-(methoxymethyl)phenyl)-2-morpholino-8-(dimethylamino)pyrido[3,2-d]pyrimidine-6-carboxylic acid |

-continued
| Example No | structures |
|---|---|
| 26 | 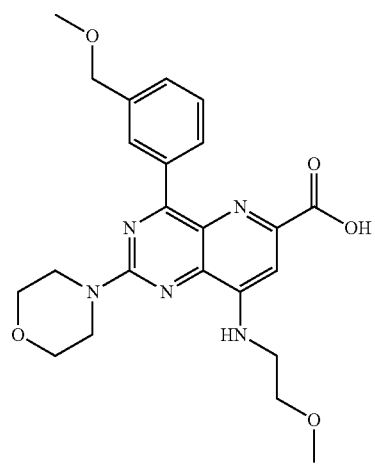 [SMILES: COCCNc1cc(C(=O)O)nc2c(-c3cccc(COC)c3)nc(N3CCOCC3)nc12] |
| 27 | 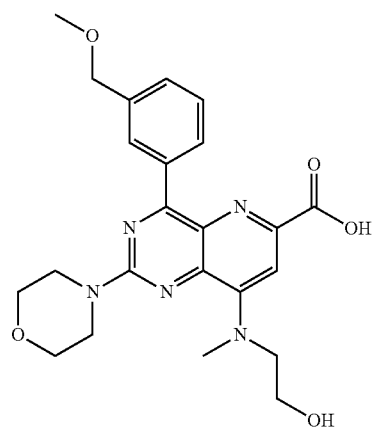 [SMILES: COCc1cccc(-c2nc(N3CCOCC3)nc3c(N(C)CCO)cc(C(=O)O)nc23)c1] |
| 28 | 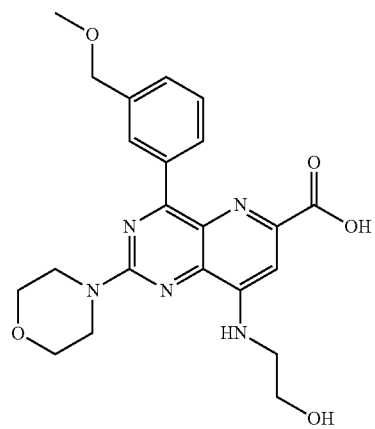 [SMILES: COCc1cccc(-c2nc(N3CCOCC3)nc3c(NCCO)cc(C(=O)O)nc23)c1] |
| 29 | 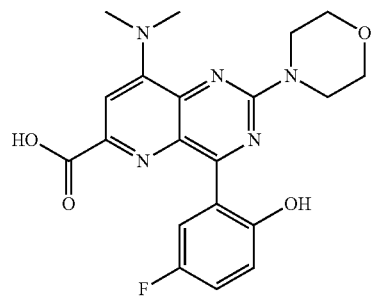 [SMILES: CN(C)c1cc(C(=O)O)nc2c(-c3cc(F)ccc3O)nc(N3CCOCC3)nc12] |
-continued
| Example No | structures |
|---|---|
| 30 | 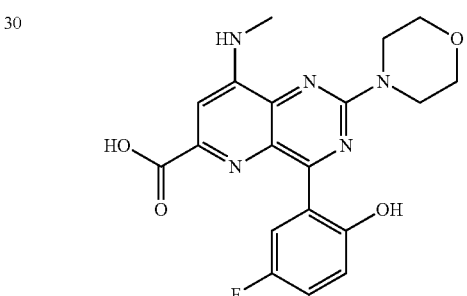 |
| 31 | 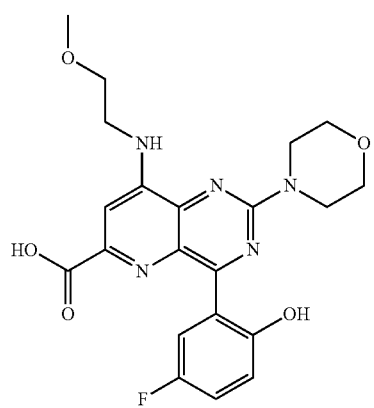 [SMILES: COCCNc1cc(C(=O)O)nc2c(-c3cc(F)ccc3O)nc(N3CCOCC3)nc12] |
| 32 | 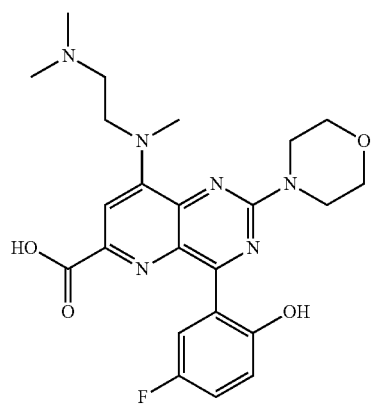 [SMILES: CN(C)CCN(C)c1cc(C(=O)O)nc2c(-c3cc(F)ccc3O)nc(N3CCOCC3)nc12] |
| 33 | 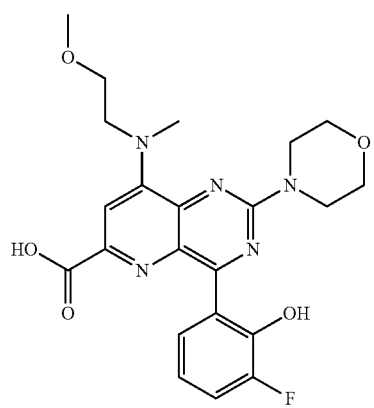 [SMILES: COCCN(C)c1cc(C(=O)O)nc2c(-c3cccc(F)c3O)nc(N3CCOCC3)nc12] |

-continued
| Example No | structures |
|---|---|
| 34 | 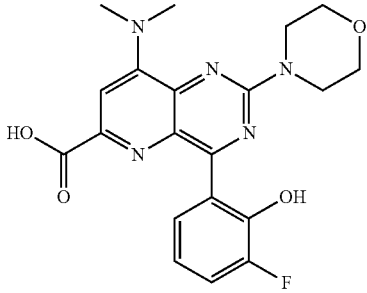 [SMILES: CN(C)c1cc(C(=O)O)nc2c(-c3cccc(F)c3O)nc(N3CCOCC3)nc12] |
| 35 | 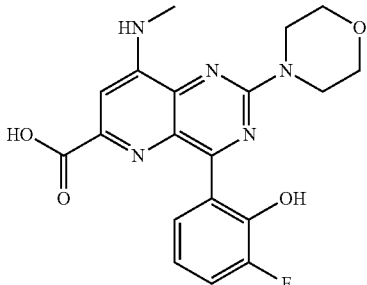 |
| 36 | 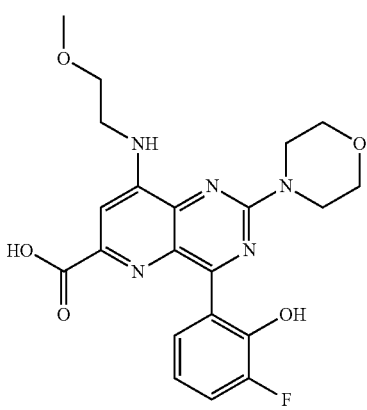 [SMILES: COCCNc1cc(C(=O)O)nc2c(-c3cccc(F)c3O)nc(N3CCOCC3)nc12] |
| 37 | 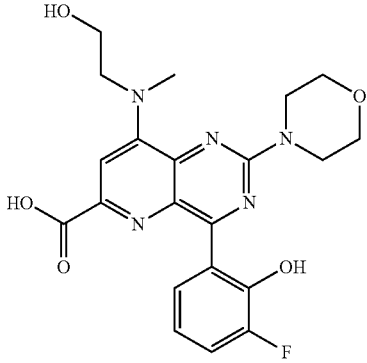 [SMILES: CN(CCO)c1cc(C(=O)O)nc2c(-c3cccc(F)c3O)nc(N3CCOCC3)nc12] |
| 38 | 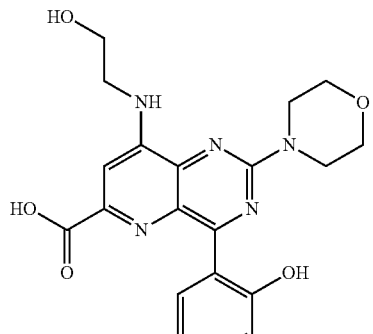 |
| 39 | 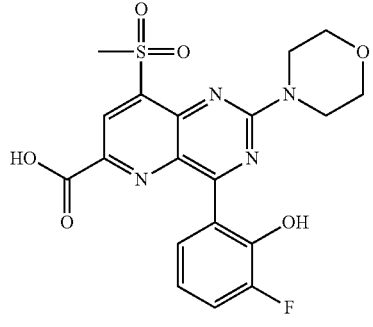 [SMILES: CS(=O)(=O)c1cc(C(=O)O)nc2c(-c3cccc(F)c3O)nc(N3CCOCC3)nc12] |
| 40 | 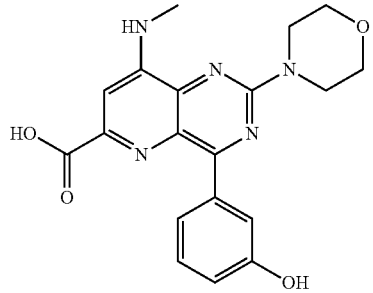 [SMILES: CNc1cc(C(=O)O)nc2c(-c3cccc(O)c3)nc(N3CCOCC3)nc12] |
| 41 | 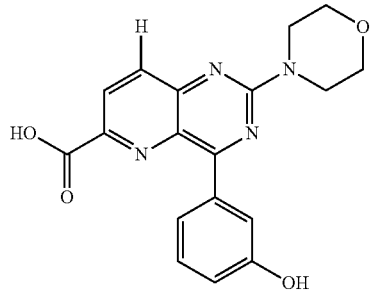 [SMILES: O=C(O)c1ccc2nc(N3CCOCC3)nc(-c3cccc(O)c3)c2n1] |
| 42 | 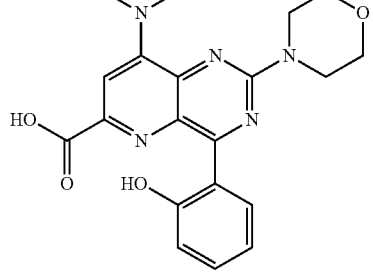 |

-continued
| Example No | structures |
|---|---|
| 43 | 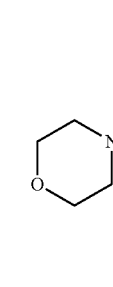 |
| 44 | 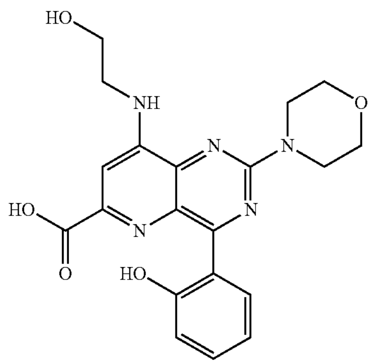 [SMILES: O=C(O)c1cc(NCCO)c2nc(N3CCOCC3)nc(-c3ccccc3O)c2n1] |
| 45 | 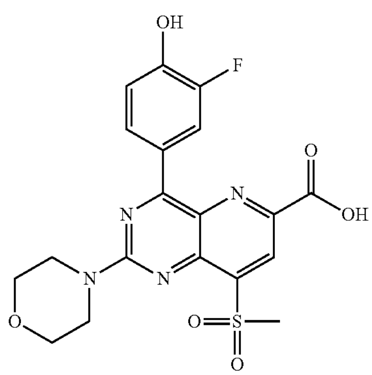 [SMILES: CS(=O)(=O)c1cc(C(=O)O)nc2c(-c3ccc(O)c(F)c3)nc(N3CCOCC3)nc12] |
| 46 | 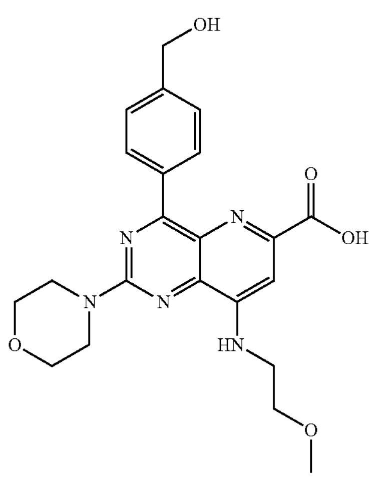 [SMILES: COCCNc1cc(C(=O)O)nc2c(-c3ccc(CO)cc3)nc(N3CCOCC3)nc12] |
-continued
| Example No | structures |
|---|---|
| 47 | 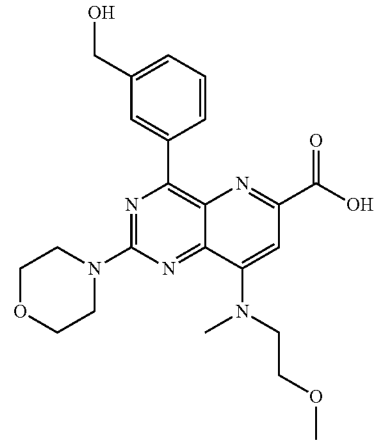 [SMILES: COCCN(C)c1cc(C(=O)O)nc2c(-c3cccc(CO)c3)nc(N3CCOCC3)nc12] |
| 48 | 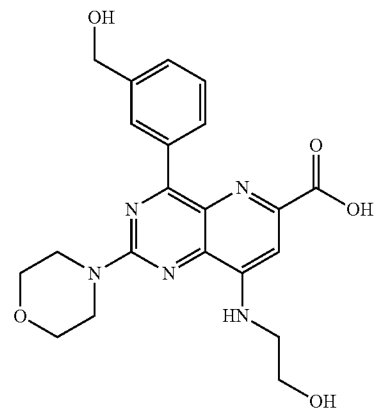 [SMILES: O=C(O)c1cc(NCCO)c2nc(N3CCOCC3)nc(-c3cccc(CO)c3)c2n1] |
| 49 | 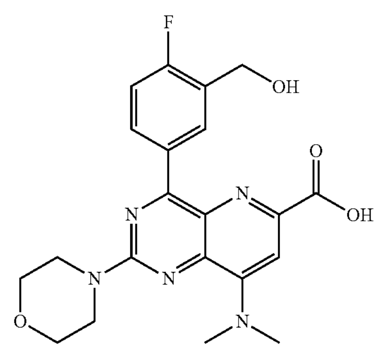 [SMILES: CN(C)c1cc(C(=O)O)nc2c(-c3ccc(F)c(CO)c3)nc(N3CCOCC3)nc12] |
| 50 | 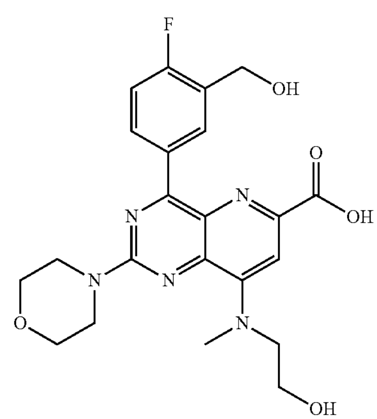 [SMILES: CN(CCO)c1cc(C(=O)O)nc2c(-c3ccc(F)c(CO)c3)nc(N3CCOCC3)nc12] |

-continued
| Example No | structures |
|---|---|
| 51 | 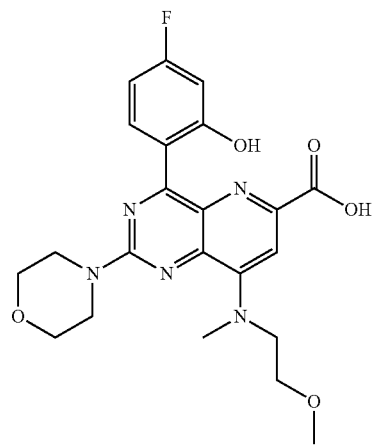 [SMILES: COCCN(C)c1cc(C(=O)O)nc2c(-c3ccc(F)cc3O)nc(N3CCOCC3)nc12] |
| 52 | 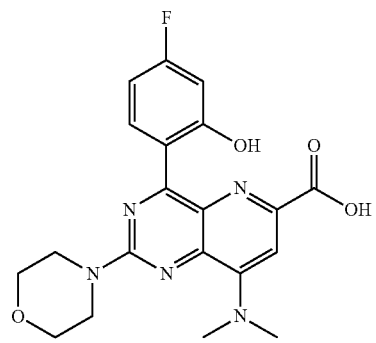 [SMILES: CN(C)c1cc(C(=O)O)nc2c(-c3ccc(F)cc3O)nc(N3CCOCC3)nc12] |
| 53 | 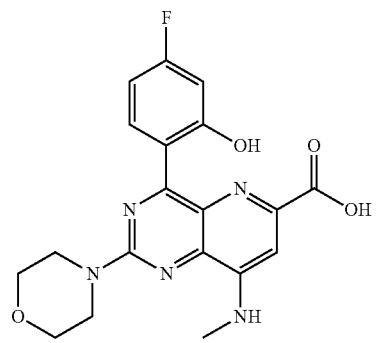 [SMILES: CNc1cc(C(=O)O)nc2c(-c3ccc(F)cc3O)nc(N3CCOCC3)nc12] |
| 54 | 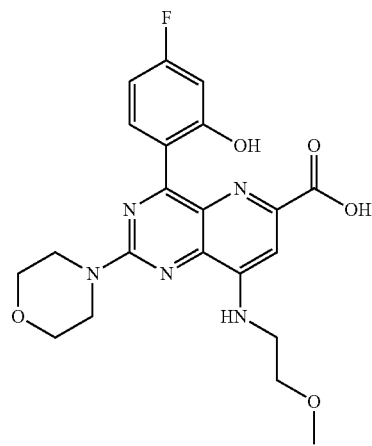 [SMILES: COCCNc1cc(C(=O)O)nc2c(-c3ccc(F)cc3O)nc(N3CCOCC3)nc12] |
-continued
| Example No | structures |
|---|---|
| 55 | 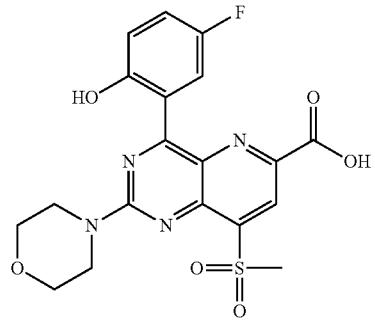 [SMILES: CS(=O)(=O)c1cc(C(=O)O)nc2c(-c3cc(F)ccc3O)nc(N3CCOCC3)nc12] |
| 56 | 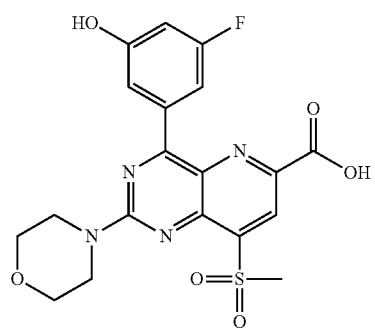 [SMILES: CS(=O)(=O)c1cc(C(=O)O)nc2c(-c3cc(O)cc(F)c3)nc(N3CCOCC3)nc12] |
| 57 | 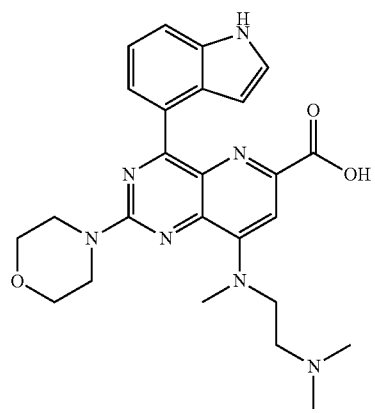 [SMILES: CN(C)CCN(C)c1cc(C(=O)O)nc2c(-c3cccc4[nH]ccc34)nc(N3CCOCC3)nc12] |
| 58 | 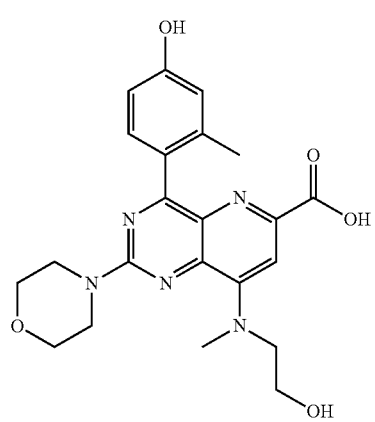 [SMILES: Cc1cc(O)ccc1-c1nc(N2CCOCC2)nc2c(N(C)CCO)cc(C(=O)O)nc12] |

-continued

| Example No | structures |
|---|---|
| 59 | (structure) |
| 60 | (structure) |
| 61 | (structure) |
| 62 | (structure) |

-continued

| Example No | structures |
|---|---|
| 63 | (structure) |
| 64 | (structure) |
| 65 | (structure) |
| 66 | (structure) |

| Example No | structures |
|---|---|
| 67 | 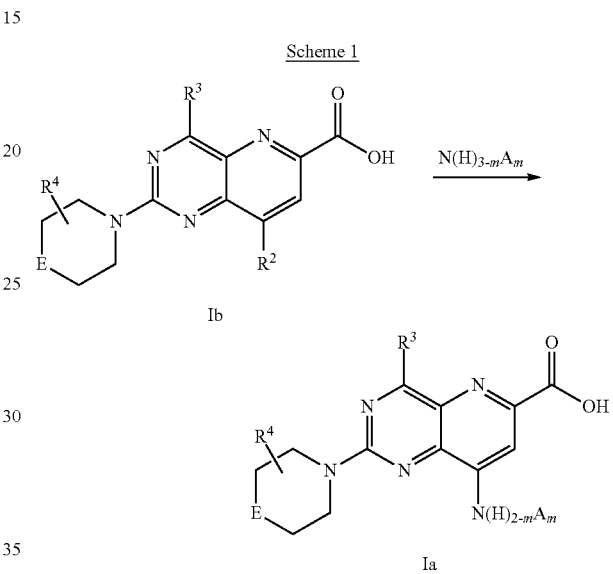 |

Synthesis of Compounds of the Invention

The pyridopyrimidine compounds according to Formula (I) may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The following abbreviations refer respectively to the definitions below:

ACN (acetonitrile), aq. (aqueous), Boc (tert-butoxycarbonyl), br s (broad signal), cHex (cyclohexane), CuTC (copper$^{(I)}$thiophene-2-carboxylate), d (doublet), DCM (dichloromethane), DIEA (diisopropylethylamine), DMA (dimethylacetamide), DMF (dimethylformamide), DMSO (dimethylsulfoxide), EA (ethyl acetate), eq. (equivalent), ES (electrospray ionization), EtOH (ethanol), Et$_2$O (diethyl ether), HPLC (high performance liquid chromatography), L (liter), LC (liquid chromatography), m (meter), MeOH (methanol), mg (milligram), min (minute), mL (milliliter), µL (microliter), mm (millimeter), µm (micrometer), mmol (millimole), MS (mass spectrometry), NMR (nuclear magnetic resonance), PE (petroleum ether), Ph (phenyl), RT (retention time), sat. (saturated), TEA (triethylamine), TFA (trifluoroacetic acid), THF (tetrahydrofurane), s (singlet), t (triplet), UV (ultraviolet).

Depending on the nature of E, $R^1$, $R^2$, $R^3$ and $R^4$ different synthetic strategies may be selected for the synthesis of compounds of Formula (I). In the process illustrated in the following schemes E, $R^1$, $R^2$, $R^3$ and $R^4$ are as above-defined in the description.

In general, the pyridopyrimidine compounds according to Formula (I) of this invention may be prepared from readily available starting materials. If such starting materials are not commercially available they may be prepared by standard synthetic techniques. The following general methods and procedures described hereinafter in the examples may be employed to prepare compounds of Formula (I).

Generally, compounds of Formula (Ia) wherein $R^3$, $R^4$ and E are as above defined can be prepared from the corresponding compounds of Formula (Ib), wherein $R^3$, $R^4$ and E are as above defined, and $R^2$ is F, Cl, Br or I, preferably Cl, by reaction with an amine of formula N(H)$_{3-m}$A$_m$ wherein A and m are as above defined, or a salt thereof, as depicted in scheme 1. The reaction may be performed in the presence or the absence of a base such as TEA or DIEA. The reaction is preferably performed in a solvent such as water, methanol, ethanol, n-propanol, i-propanol, THF, dioxane, or a mixture thereof at a temperature ranging from about −20° C. to about 200° C., preferably from 100° C. to 200° C. Microwave or conventional heating can be used. The reaction is preferably performed for few minutes to few hours, more preferably for one to 4 hours. Most preferably, the reaction of scheme 1 is performed under microwave irradiation in water in the presence of DIEA at 170° C. for few minutes to few hours.

Scheme 1

Preferably, the method can be used for preparing the following compounds of Formula (Ia) selected below:

4-(4-Hydroxy-phenyl)-8-[(2-methoxy-ethyl)-methyl-amino]-2-morpholin-4-yl-pyrido[3,2-d]pyrimidine-6-carboxylic acid 8-Dimethylamino-4-(4-hydroxy-phenyl)-2-morpholin-4-yl-pyrido[3,2-d]pyrimidine-6-carboxylic acid 8-(2-Hydroxy-ethylamino)-4-(4-hydroxy-phenyl)-2-morpholin-4-yl-pyrido[3,2-d]pyrimidine-6-carboxylic acid 4-(4-Hydroxy-phenyl)-8-(2-methoxy-ethylamino)-2-morpholin-4-yl-pyrido[3,2-d]pyrimidine-6-carboxylic acid 4-(3-Hydroxy-phenyl)-8-[(2-methoxy-ethyl)-methyl-amino]-2-morpholin-4-yl-pyrido[3,2-d]pyrimidine-6-carboxylic acid 8-(2-Hydroxy-ethylamino)-4-(3-hydroxy-phenyl)-2-morpholin-4-yl-pyrido[3,2-d]pyrimidine-6-carboxylic acid 4-(3-Fluoro-5-hydroxy-phenyl)-8-[(2-methoxy-ethyl)-methyl-amino]-2-morpholin-4-yl-pyrido[3,2-d]pyrimidine-6-carboxylic acid 4-(3-Fluoro-5-hydroxy-phenyl)-8-(2-hydroxy-ethylamino)-2-morpholin-4-yl-pyrido[3,2-d]pyrimidine-6-carboxylic acid 8-Dimethylamino-4-(1H-indol-4-yl)-2-morpholin-4-yl-pyrido[3,2-d]pyrimidine-6-carboxylic acid 4-(1H-Indol-4-yl)-8-methylamino-2-morpholin-4-yl-pyrido[3,2-d]pyrimidine-6-carboxylic acid 4-(1H-Indol-4-yl)-8-(2-methoxy-ethylamino)-2-morpholin-4-yl-pyrido[3,2-d]pyrimidine-6-carboxylic acid 8-[(2-Hydroxy-ethyl)-methyl-amino]-4-(1H-indol-4-yl)-2-morpholin-4-yl-pyrido[3,2-d]pyrimidine-6-carboxylic acid 4-(1H-Indol-5-yl)-8-[(2-methoxy-ethyl)-methyl-amino]-2-morpholin-4-yl-pyrido[3,2-d]pyrimidine-6-carboxylic acid 4-(4-Hydroxymethyl-phenyl)-8-[(2-methoxy-ethyl)-methyl-amino]-2-morpholin-4-yl-pyrido[3,2-d]pyrimidine-6-carboxylic acid 8-Dimethylamino-4-(3-hydroxymethyl-phenyl)-2-morpholin-4-yl-pyrido[3,2-d]pyrimidine-6-carboxylic acid 8-[(2-Hydroxy-ethyl)-methyl-amino]-4-(3-hydroxymethyl-phenyl)-2-morpholin-4-yl-pyrido[3,2-d]pyrimidine-6-carboxylic acid 8-Dimethylamino-4-(3-methoxymethyl-phenyl)-2-morpholin-4-yl-pyrido[3,2-d]pyrimidine-6-carboxylic acid 8-(2-Methoxy-ethylamino)-4-(3-methoxymethyl-phenyl)-2-morpholin-4-yl-pyrido[3,2-d]pyrimidine-6-carboxylic acid 8-[(2-Hydroxy-ethyl)-methyl-amino]-4-(3-methoxymethyl-phenyl)-2-morpholin-4-yl-pyrido[3,2-d]pyrimidine-6-carboxylic acid 8-(2-Hydroxy-ethylamino)-4-(3-methoxymethyl-phenyl)-2-morpholin-4-yl-pyrido[3,2-d]pyrimidine-6-carboxylic acid 8-(Dimethylamino)-4-(5-fluoro-2-hydroxyphenyl)-2-morpholin-4-ylpyrido[3,2-d]pyrimidine-6-carboxylic acid 4-(5-Fluoro-2-hydroxyphenyl)-8-(methylamino)-2-morpholin-4-ylpyrido[3,2-d]pyrimidine-6-carboxylic acid 4-(5-Fluoro-2-hydroxyphenyl)-8-[(2-methoxyethyl)amino]-2-morpholin-4-ylpyrido[3,2-d]pyrimidine-6-carboxylic acid 8-[[2-(Dimethylamino)ethyl](methyl)amino]-4-(5-fluoro-2-hydroxyphenyl)-2-morpholin-4-ylpyrido[3,2-d]pyrimidine-6-carboxylic acid 4-(3-Fluoro-2-hydroxyphenyl)-8-[(2-methoxyethyl)(methyl)amino]-2-morpholin-4-ylpyrido[3,2-d]pyrimidine-6-carboxylic acid 8-(Dimethylamino)-4-(3-fluoro-2-hydroxyphenyl)-2-morpholin-4-ylpyrido[3,2-d]pyrimidine-6-carboxylic acid 4-(3-Fluoro-2-hydroxyphenyl)-8-(methylamino)-2-morpholin-4-ylpyrido[3,2-d]pyrimidine-6-carboxylic acid 4-(3-Fluoro-2-hydroxyphenyl)-8-[(2-methoxyethyl)amino]-2-morpholin-4-ylpyrido[3,2-d]pyrimidine-6-carboxylic acid 4-(3-Fluoro-2-hydroxyphenyl)-8-[(2-hydroxyethyl)(methyl)amino]-2-morpholin-4-ylpyrido[3,2-d]pyrimidine-6-carboxylic acid 4-(3-Fluoro-2-hydroxyphenyl)-8-[(2-hydroxyethyl)amino]-2-morpholin-4-ylpyrido[3,2-d]pyrimidine-6-carboxylic acid 4-(3-Hydroxyphenyl)-8-(methylamino)-2-morpholin-4-ylpyrido[3,2-d]pyrimidine-6-carboxylic acid 8-(Dimethylamino)-4-(2-hydroxyphenyl)-2-morpholin-4-ylpyrido[3,2-d]pyrimidine-6-carboxylic acid 8-[[2-(Dimethylamino)ethyl](methyl)amino]-4-(2-hydroxyphenyl)-2-morpholin-4-ylpyrido[3,2-d]pyrimidine-6-carboxylic acid 8-[(2-Hydroxyethyl)amino]-4-(2-hydroxyphenyl)-2-morpholin-4-ylpyrido[3,2-d]pyrimidine-6-carboxylic acid 4-[4-(Hydroxymethyl)phenyl]-8-[(2-methoxyethyl)amino]-2-morpholin-4-ylpyrido[3,2-d]pyrimidine-6-carboxylic acid 4-[3-(Hydroxymethyl)phenyl]-8-[(2-methoxyethyl)(methyl)amino]-2-morpholin-4-ylpyrido[3,2-d]pyrimidine-6-carboxylic acid 8-[(2-Hydroxyethyl)amino]-4-[3-(hydroxymethyl)phenyl]-2-morpholin-4-ylpyrido[3,2-d]pyrimidine-6-carboxylic acid 8-(Dimethylamino)-4-[4-fluoro-3-(hydroxymethyl)phenyl]-2-morpholin-4-ylpyrido[3,2-d]pyrimidine-6-carboxylic acid 4-[4-Fluoro-3-(hydroxymethyl)phenyl]-8-[(2-hydroxyethyl)(methyl)amino]-2-morpholin-4-ylpyrido[3,2-d]pyrimidine-6-carboxylic acid 4-(4-Fluoro-2-hydroxyphenyl)-8-[(2-methoxyethyl)(methyl)amino]-2-morpholin-4-ylpyrido[3,2-d]pyrimidine-6-carboxylic acid 8-(Dimethylamino)-4-(4-fluoro-2-hydroxyphenyl)-2-morpholin-4-ylpyrido[3,2-d]pyrimidine-6-carboxylic acid 4-(4-Fluoro-2-hydroxyphenyl)-8-(methylamino)-2-morpholin-4-ylpyrido[3,2-d]pyrimidine-6-carboxylic acid 4-(4-Fluoro-2-hydroxyphenyl)-8-[(2-methoxyethyl)amino]-2-morpholin-4-ylpyrido[3,2-d]pyrimidine-6-carboxylic acid 8-[[2-(Dimethylamino)ethyl](methyl)amino]-4-(1H-indol-4-yl)-2-morpholin-4-ylpyrido[3,2-d]pyrimidine-6-carboxylic acid 8-[(2-Hydroxyethyl)(methyl)amino]-4-(4-hydroxy-2-methylphenyl)-2-morpholin-4-ylpyrido[3,2-d]pyrimidine-6-carboxylic acid 4-(4-Fluoro-2-hydroxyphenyl)-8-[(2-hydroxyethyl)(methyl)amino]-2-morpholin-4-ylpyrido[3,2-d]pyrimidine-6-carboxylic acid 4-(3-Hydroxyphenyl)-8-[4-(methylsulfonyl)piperazin-1-yl]-2-morpholin-4-ylpyrido[3,2-d]pyrimidine-6-carboxylic acid 4-(3,5-Difluorophenyl)-8-[(2-methoxyethyl)(methyl)amino]-2-morpholin-4-ylpyrido[3,2-d]pyrimidine-6-carboxylic acid 4-(3-Cyanophenyl)-8-(dimethylamino)-2-morpholin-4-ylpyrido[3,2-d]pyrimidine-6-carboxylic acid 8-[4-(Methylsulfonyl)piperazin-1-yl]-2-morpholin-4-yl-4-phenylpyrido[3,2-d]pyrimidine-6-carboxylic acid Generally, compounds of Formula (Ic) wherein $R^3$, $R^4$, A and E are as above defined can be prepared from the corresponding derivatives of Formula (IIa), wherein A is as above defined, preferably methyl or ethyl, and $R^2$ is F, Cl, Br or I, preferably Cl, by reaction with AO—Na, or another salt thereof, as depicted in Scheme 2. The reaction may be carried out in the presence or the absence of a base such as TEA or DIEA, in a solvent such as water, methanol, ethanol, n-propanol, i-propanol, THF, dioxane, DMF or a mixture thereof. The reaction is performed at a temperature ranging from about −20° C. to about 200° C., preferably from 100° C. to 200° C., under microwave or conventional heating. The reaction is preferably performed for few hours to few days, more preferably from about ten to about twenty hours. Most preferably, the reaction is performed with AO—Na in DMF at 120° C. for about 16 h.

Scheme 2

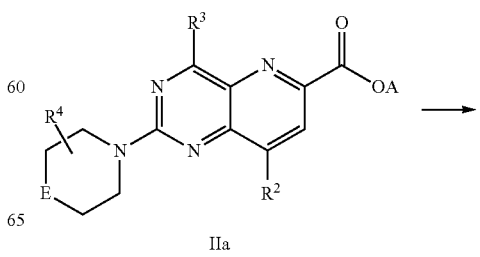

IIa

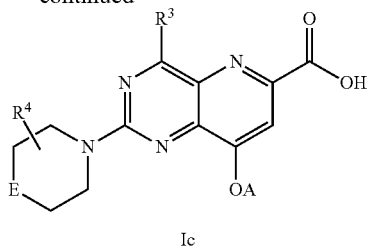

Ic

Preferably, the method can be used for preparing the following compounds of Formula (Ic) selected below:

4-(4-Hydroxy-phenyl)-8-(2-methoxy-ethoxy)-2-morpholin-4-yl-pyrido[3,2-d]pyrimidine-6-carboxylic acid 4-(3-Hydroxy-phenyl)-8-(2-methoxy-ethoxy)-2-morpholin-4-yl-pyrido[3,2-d]pyrimidine-6-carboxylic acid 4-(3-Fluoro-5-hydroxy-phenyl)-8-(2-methoxy-ethoxy)-2-morpholin-4-yl-pyrido[3,2-d]pyrimidine-6-carboxylic acid Generally, compounds of Formula (Id) wherein $R^3$, $R^4$ and E are as above defined can be prepared from the corresponding compound of Formula (IIb), wherein $R^3$, $R^4$, E and A are as above defined, preferably A is methyl or ethyl, by hydrolysis, as depicted in Scheme 3. This reaction is preferably performed using reagents such as, but not limited to, LiOH, NaOH or KOH in solvents such as water, methanol, ethanol, n-propanol, i-propanol, THF, dioxane, or a mixture thereof at a temperature ranging from about −20° C. to about 120° C., preferably from 20° C. to 50° C. The reaction is preferably performed for few hours to few days, more preferably from ten to twenty hours. Most preferably, the hydrolysis is performed with NaOH in a mixture THF/water at room temperature for about 14 hours.

Scheme 3

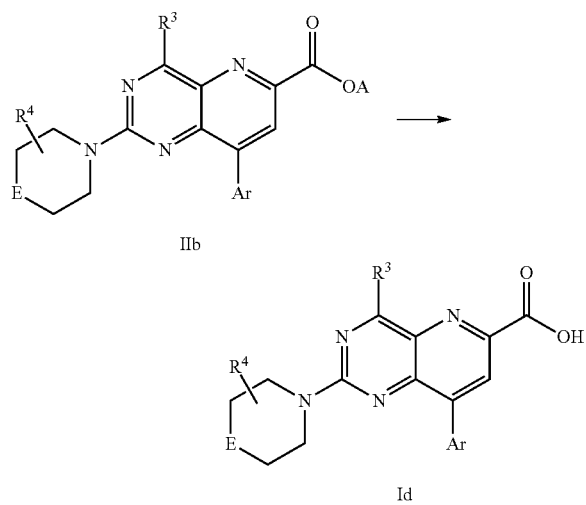

Preferably, the method can be used for preparing the following compounds of Formula (Id) selected below:

4-(3-hydroxyphenyl)-8-(2-methoxyphenyl)-2-morpholin-4-ylpyrido[3,2-d]pyrimidine-6-carboxylic acid 4-(3-Hydroxyphenyl)-2-morpholin-4-ylpyrido[3,2-d]pyrimidine-6-carboxylic acid 4-(3-Hydroxyphenyl)-2-morpholin-4-yl-8-(1-naphthyl)pyrido[3,2-d]pyrimidine-6-carboxylic acid Generally, compounds of Formula (Ie) wherein $R^3$, $R^4$ and E are as above defined can be prepared from the corresponding esters of Formula (IIc), wherein A is as above defined, preferably methyl or ethyl, by hydrolysis, as depicted in Scheme 4. The reaction may be performed using reagents such as, but not limited to, LiOH, NaOH or KOH in solvents such as water, methanol, ethanol, n-propanol, i-propanol, THF, dioxane, or a mixture thereof at a temperature ranging from about −20° C. to about 120° C., preferably from 20° C. to 50° C. The reaction is preferably performed for few hours to few days, more preferably from about ten to about twenty hours. Most preferably, the hydrolysis is performed with NaOH in a mixture THF/water at room temperature for about 14 hours.

Scheme 4

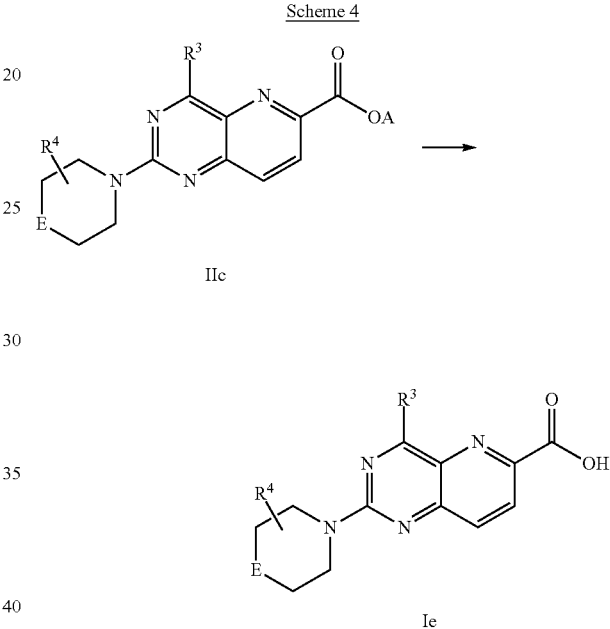

Preferably, the method can be used for preparing the following compounds of Formula (Ie) selected below:

4-(3-Methoxyphenyl)-2-morpholin-4-ylpyrido[3,2-d]pyrimidine-6-carboxylic acid 4-(4-Hydroxy-phenyl)-2-morpholin-4-yl-pyrido[3,2-d]pyrimidine-6-carboxylic acid Generally, compounds of Formula (Ib) wherein $R^3$, $R^4$ and E are as above defined, and $R^2$ is halogen, preferably Cl, can be prepared from the corresponding compounds of Formula (IIa), wherein A is as above defined, preferably methyl or ethyl, $R^2$ is halogen, preferably Cl, by hydrolysis, as depicted in Scheme 5. The reaction may be performed using reagents such as, but not limited to, LiOH, NaOH or KOH in solvents such as water, methanol, ethanol, n-propanol, i-propanol, THF, dioxane, or a mixture thereof at a temperature ranging from −20° C. to 120° C., preferably from 20° C. to 100° C. This reaction is preferably performed for few hours, more preferably from one to five hours. Most preferably, the hydrolyisis is performed using LiOH in a mixture THF/MeOH/water.

Scheme 5

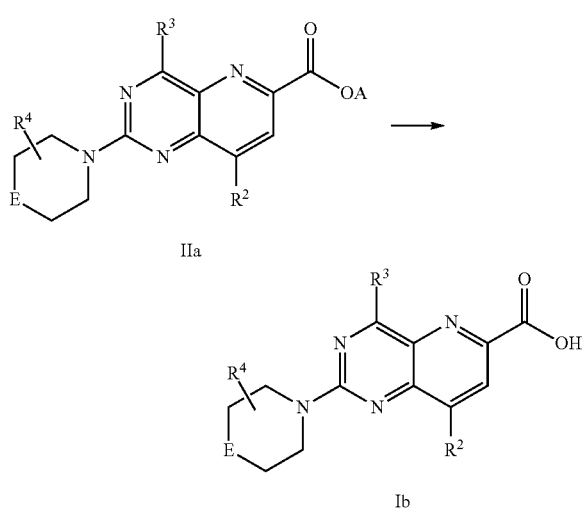

IIa

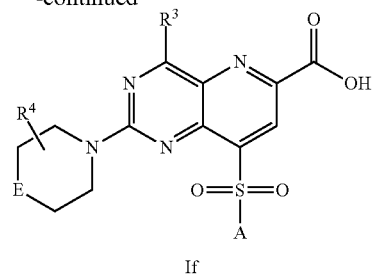

If

Preferably, the method can be used for preparing the following compounds of Formula (If) selected below:
4-(5-Fluoro-2-hydroxyphenyl)-8-(methylsulfonyl)-2-morpholin-4-ylpyrido[3,2-d]pyrimidine-6-carboxylic acid
4-(3-Fluoro-4-hydroxyphenyl)-8-(methylsulfonyl)-2-morpholin-4-ylpyrido[3,2-d]pyrimidine-6-carboxylic acid
4-(3-Fluoro-2-hydroxyphenyl)-8-(methylsulfonyl)-2-morpholin-4-ylpyrido[3,2-d]pyrimidine-6-carboxylic acid
4-(3-Fluoro-5-hydroxyphenyl)-8-(methylsulfonyl)-2-morpholin-4-ylpyrido[3,2-d]pyrimidine-6-carboxylic acid Generally, compounds of Formula (Ig) wherein $R^4$, $R^3$ and E are as above defined and $R^2$ is A, preferably methyl, can be prepared from the compounds of Formula (Ib), wherein $R^2$ is Br, I, Cl, preferably Cl, via a cross coupling reaction with an alkyl boronic acid of Formula A-B(OH)$_2$ or an organozincic of Formula A-Zn—X in the presence of a palladium source such as Pd(PPh$_3$)$_4$, Pd(PPh$_3$)$_2$Cl$_2$, Pd$_2$(dba)$_3$, Pd(OAc)$_2$ or PdCl$_2$(ACN)$_2$, as depicted in Scheme 7. The reaction may be performed in a solvent such as THF, dioxane, toluene, EtOH, DMF or DMA, or a mixture thereof at a temperature ranging from about 20° C. to about 100° C., preferably from 60° C. to 100° C. The reaction is preferably performed for few hours, more preferably from about ten to about twenty hours. Most preferably, this reaction is performed using Me-ZnCl and Pd(PPh$_3$)$_4$ in dioxane at about 80° C. for about 16 hours.

Ib

Preferably, the method can be used for preparing the following compounds of Formula (I-b) selected below:
8-Chloro-4-(3-methoxyphenyl)-2-morpholin-4-ylpyrido[3,2-d]pyrimidine-6-carboxylic acid
8-Chloro-4-(3-hydroxyphenyl)-2-morpholin-4-ylpyrido[3,2-d]pyrimidine-6-carboxylic acid
8-Chloro-2-morpholin-4-yl-4-phenylpyrido[3,2-d]pyrimidine-6-carboxylic acid Generally, compounds of Formula (If) wherein $R^3$, $R^4$ and E are as above defined, and $R^2$ is SO$_2$A, preferably SO$_2$Me, can be prepared from the corresponding compounds of Formula (IIa), wherein A is as above defined, preferably methyl or ethyl, $R^2$ is halogen, preferably Cl, in two steps as depicted in Scheme 6 by SN$_{Ar}$ followed by oxidation. The first step may be performed using reagents such as AS—Na or ASH in the presence or not of a base in solvents such as DMF, dioxane, or a mixture thereof at a temperature ranging from –20° C. to 120° C., preferably from 50° C. to 100° C. This reaction is preferably performed for few hours, more preferably from five to twenty hours. Most preferably, the SN$_{Ar}$ is performed using MeS—Na in DMF in a sealed tube. The oxidation may be performed using reagents such as m-CPBA, hydrogen peroxide in the presence of a catalyst such as sodium tungstate, in solvents such as DCM, MeOH or ethanol at a temperature ranging from –20° C. to 120° C., preferably from 0° C. to 50° C. This reaction is preferably performed for few hours, more preferably from two to five hours. Most preferably, the oxidation is performed using hydrogen peroxide in the presence of sodium tungstate in MeOH.

Scheme 6

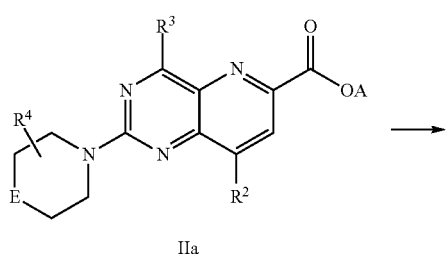

IIa

Scheme 7

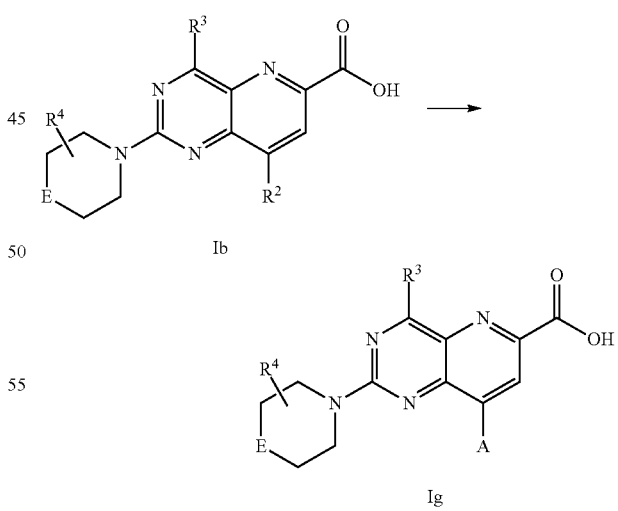

Preferably, the method can be used for preparing the following compounds of Formula (Ig) selected below:
4-(3-Hydroxyphenyl)-8-methyl-2-morpholin-4-ylpyrido[3,2-d]pyrimidine-6-carboxylic acid Generally, compounds of Formula (Ih) wherein $R^4$, $R^3$ and E are as above defined and $R^2$ is 4-acylpiperazine, preferably 4-acetylpiperazine, can be prepared from the compounds of Formula (Ia), wherein R² is piperazine by reaction with an acyl chloride or an acid anhydride as depicted in Scheme 8. The reaction may be performed in a solvent such as DCM, THF, dioxane, DMF or DMA, or a mixture thereof, in the presence or not of a base such as triethylamine or DIEA, at a temperature ranging from about −20° C. to about 100° C., preferably from 0° C. to 40° C. The reaction is preferably performed for few hours, more preferably from about ten to about twenty hours. Most preferably, this reaction is performed using acetyl chloride in DCM at about 20° C. for about 18 hours.

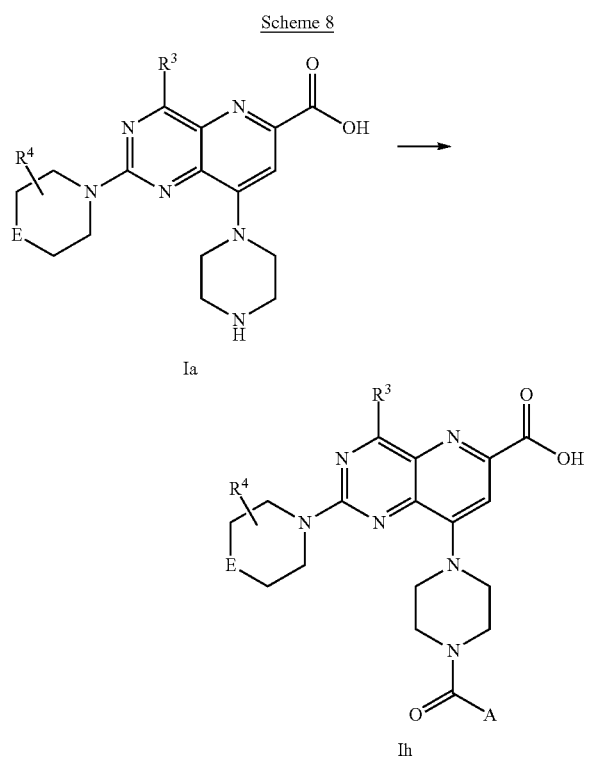

Scheme 8

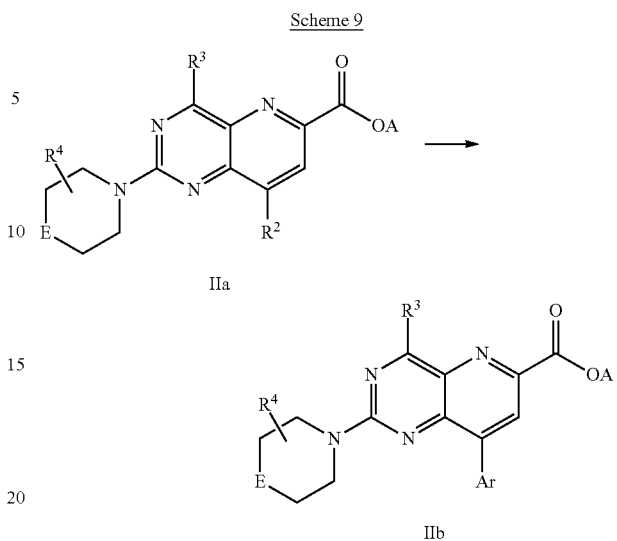

Scheme 9

Preferably, the method can be used for preparing the following compounds of Formula (Ih) selected below:

8-(4-Acetylpiperazin-1-yl)-4-(3-hydroxyphenyl)-2-morpholin-4-ylpyrido[3,2-d]pyrimidine-6-carboxylic acid.

Generally, compounds of Formula (IIb) wherein R³, R⁴ and E are as above defined and A is preferably methyl or ethyl, can be prepared from compounds of Formula (IIa), wherein A is as above defined, preferably methyl or ethyl, and R² is Cl, Br or I, preferably Cl, via a cross coupling reaction with an aryl boronic acid of Formula Ar—B(OH)₂, an aryl boronic ester of Formula Ar—B(OA)₂ or an aryl stannane of Formula Ar—SnA₃, as depicted in Scheme 9. The reaction may be performed in the presence of a palladium source such as Pd(PPh₃)₄, Pd(PPh₃)₂Cl₂, Pd₂(dba)₃, Pd(OAc)₂ or PdCl₂(ACN)₂. The reaction may also be performed in the presence of a base such as TEA, DIEA, Cs₂CO₃, K₂CO₃ in solvent such as THF, dioxane, toluene, EtOH, DMF or DMA, or a mixture thereof, at a temperature ranging from about 50° C. to about 150° C., preferably from 70° C. to 120° C. This reaction is preferably performed for few hours, more preferably from about 2 to about 6 hours. Most preferably, the reaction is performed using Ar—B(OH)₂, Cs₂CO₃ and Pd(PPh₃)₄ in dioxane at about 90° C. for about 4 hours.

Generally, compounds of Formula (IIc) wherein R³, R⁴ and E are as above defined and A is preferably methyl or ethyl, can be prepared from compounds of Formula (IIa), wherein A is as above defined, preferably methyl or ethyl, and R² is Cl, Br or I, preferably Cl, via a reduction as depicted in Scheme 10. Such a reaction may use a palladium source such as Pd/C and hydrogen or a source of hydrogen such as formic acid, ammonium formate, cyclohexadiene, in a solvent such as a water, methanol, ethanol, n-propanol, i-propanol, ethyl acetate or a mixture thereof at a temperature ranging from about 0° C. to about 120° C., preferably from r.t. to 100° C. The reaction is preferably performed for a few minutes to a few hours, more preferably from 30 minutes to about 2 hours (Scheme 7). Most preferably, the reaction is performed using Pd/C and HCOONH₄, in boiling ethanol.

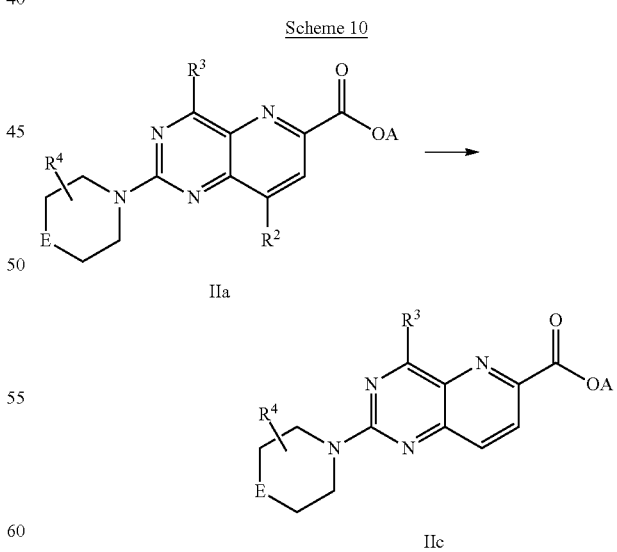

Scheme 10

Generally, compounds of Formula (IIa) wherein R⁴, R³ and E are as above defined, R² is Br, I, Cl, preferably Cl, and A is as above defined, preferably methyl or ethyl, can be prepared from the compounds of Formula (IIIa), wherein A is as above defined, preferably methyl or ethyl and R² is Br, I, Cl, preferably Cl, via a cross coupling reaction with an aryl boronic acid of Formula Ar—B(OH)$_2$ or an heteroaryl boronic acid of formula Het-B(OH)$_2$ in the presence of a palladium source such as Pd(PPh$_3$)$_4$, Pd(PPh$_3$)$_2$Cl$_2$, Pd$_2$(dba)$_3$, Pd(OAc)$_2$ or PdCl$_2$(ACN)$_2$, as depicted in Scheme 11. The reaction may be performed in the presence of a copper salt such as CuTC, in a solvent such as THF, dioxane, toluene, EtOH, DMF or DMA, or a mixture thereof at a temperature ranging from about 20° C. to about 100° C., preferably from 40° C. to 70° C. The reaction is preferably performed for few hours, more preferably from about six to about twenty hours as described for example in *Org. Lett.* 2002, 4, 979-81. Most preferably, this reaction is performed using Ar—B(OH)$_2$ or Het-B(OH)$_2$, CuTC, Pd(PPh$_3$)$_4$ in dioxane at about 55° C. for about 16 hours.

Scheme 11

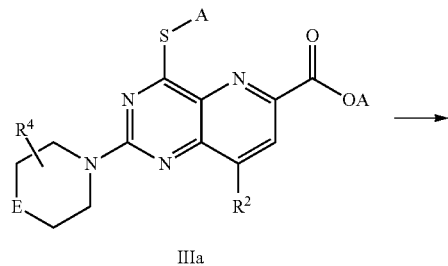

IIIa

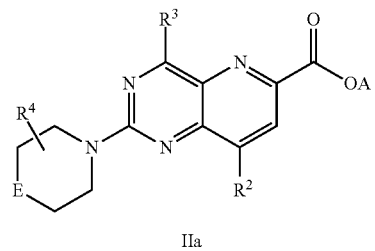

IIa

Alternatively, compounds of Formula (IIa) wherein R$^4$, R$^3$ and E are as above defined, R$^2$ is Cl, Br, I, preferably Cl, and wherein A is as above defined, preferably methyl or ethyl, can be prepared from compounds of Formula (IVa), wherein A is as above defined, preferably methyl or ethyl, R$^2$ is Cl, Br, I, preferably Cl, by reaction with an amine of Formula (VII), or a salt thereof, as depicted in Scheme 12. The reaction may be performed in the presence or the absence of a base such as TEA or DIEA, in a solvent such as water, a THF, dioxane, DMF, DMA, ACN or a mixture thereof at a temperature ranging from −20° C. to 100° C., preferably from about 0° C. to about 40° C. The reaction is preferably performed for few hours, more preferably from one to three hours. Most preferably, compounds of Formula (IIa) wherein E is O and R$^4$ is H are prepared using morpholine in the presence of DIEA in ACN, at room temperature for about one hour.

Scheme 12

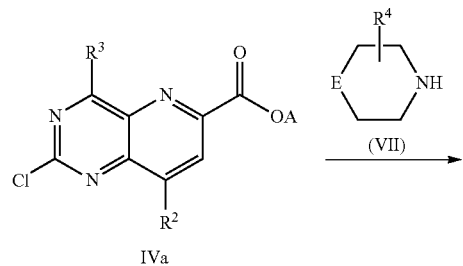

IVa

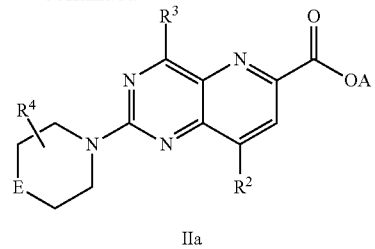

IIa

Generally, compounds of Formula (IIIa) wherein E and R$^4$ are as above defined, A is preferably methyl or ethyl, and R$^2$ is Cl, Br, I, preferably Cl, can be prepared from the compounds of Formula (V), wherein A is as above defined, preferably methyl or ethyl, and R$^2$ is Cl, Br, I, preferably Cl, by reaction with an amine of Formula (VII), or a salt thereof, as depicted in Scheme 13. The reaction may be performed in the presence or the absence of a base such as TEA or DIEA, in a solvent such as water, a THF, dioxane, DMF, DMA, ACN or a mixture thereof at a temperature ranging from about −20° C. to about 100° C., preferably from 0° C. to 40° C., for a few hours, preferably from ten to twenty hours. Most preferably, compounds of Formula (IIIa) wherein E is O and R$^4$ is H may be prepared using morpholine in the presence of DIEA in ACN at room temperature for about 12 hours.

Scheme 13

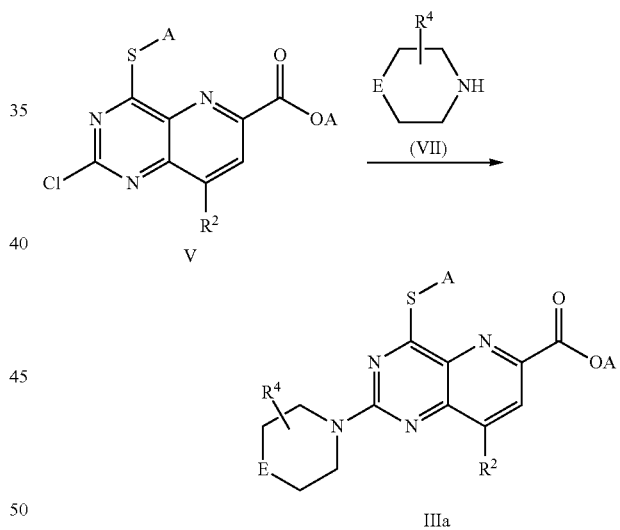

Generally, compounds of Formula (IVa) wherein A and R$^3$ are as above defined, preferably methyl or ethyl, and R$^2$ is Cl, Br, I, preferably, Cl, can be prepared from the compounds of Formula (V), wherein A is as above defined, preferably methyl or ethyl, and R$^2$ is Cl, Br, I, preferably, Cl, via a cross coupling reaction with an aryl boronic acid of Formula Ar—B (OH)$_2$ or an heteroaryl boronic acid of formula Het-B(OH)$_2$ in the presence of a palladium source such as Pd(PPh$_3$)$_4$, Pd(PPh$_3$)$_2$Cl$_2$, Pd$_2$(dba)$_3$, Pd(OAc)$_2$ or PdCl$_2$(ACN)$_2$, as depicted in Scheme 14. The reaction may be performed in the presence of a copper salt such as CuTC, in a solvent such as THF, dioxane, toluene, EtOH, DMF or DMA, or a mixture thereof at a temperature ranging from about 20° C. to about 100° C., preferably from 40° C. to 70° C., for a few hours, preferably from about ten to about twenty hours. Most preferably, the reaction is performed using Ar—B(OH)$_2$ or Het-B(OH)$_2$, CuTC, and Pd(PPh$_3$)$_4$ in dioxane at about 55° C. for about 16 hours.

Scheme 14

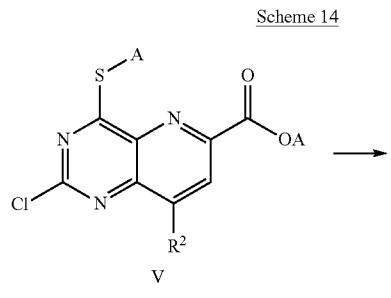

Scheme 15

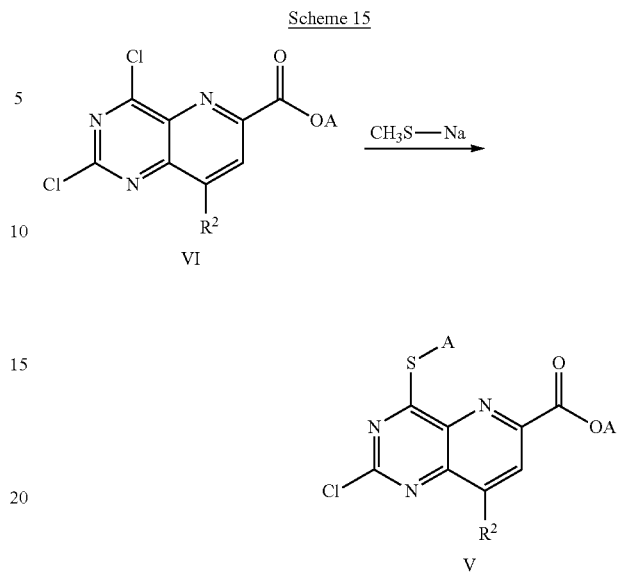

Compound of Formula (VI) wherein R$^2$ is Cl, can be prepared in 3 steps starting from 5-aminouracil and dimethyl acetylene dicarboxylate as described in *J. Org. Chem.* 1979, 44, 435-440 (Scheme 16).

Scheme 16

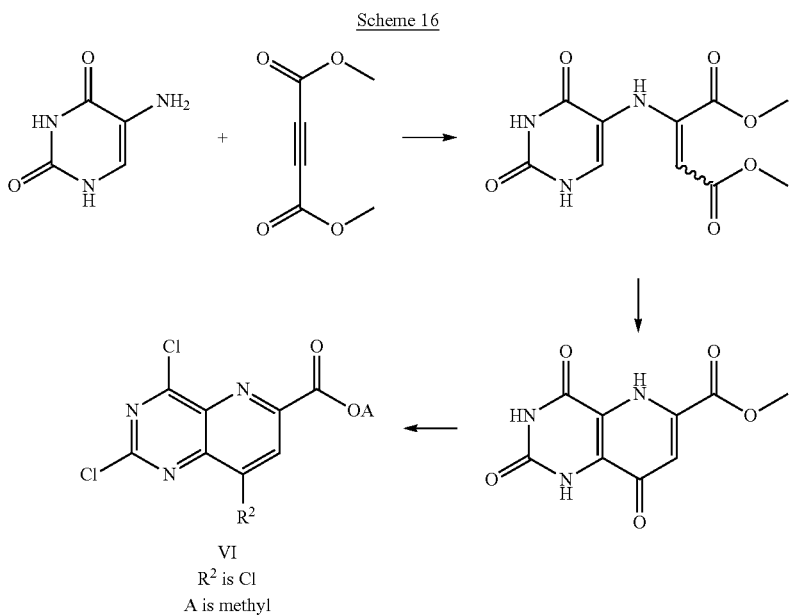

VI
R$^2$ is Cl
A is methyl

Compounds of Formula (V) can be prepared from compounds of Formula (VI), by reaction with a thiol of Formula (A-SH) wherein A is as above defined, or a salt thereof, as depicted in Scheme 15. The reaction may be performed in the presence or the absence of a base such as TEA or DIEA, in a solvent such as THF, dioxane, DCM, DCE, ACN, DMF, DMA or a mixture thereof, at a temperature ranging from −40° C. to 40° C., preferably from −20° C. to 10° C., for a few hours, preferably from one to five hours. Most preferably, the reaction is performed in DCM at about −10° C. for about 3 hours.

According to a further general process, compounds of formula (I), and any subformulae can be converted to alternative compounds of formula (I) and any subformulae, employing suitable inter-conversion techniques well known by a person skilled in the art.

In another preferred embodiment, compounds of Formula (I) wherein R$^1$ is CO$_2$(C$_1$-C$_8$)alkyl or H and R$^2$ is Hal or H, and R$^3$ is SA, Ar or Het, may be obtained by reacting the intermediate M wherein R$^1$ is CO$_2$(C$_1$-C$_8$)alkyl or H and R$^2$ is Hal or H, and R$^3$ is SA, Ar or Het, with morpholine or the amine (VII) wherein E and R$^4$ are as above defined, preferably morpholine.

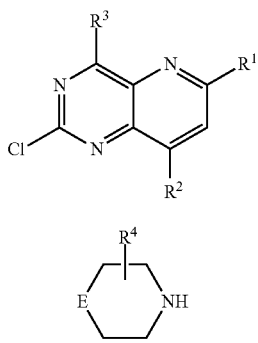

(VII)

The compounds of the formula (I) and related formulae and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), under reaction conditions which are known and suitable for the said reactions. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Use can also be made here of variants which are known per se, but are not mentioned here in greater detail.

If desired, the starting materials can also be formed in situ so that they are not isolated from the reaction mixture, but instead are immediately converted further into the compounds of the formula (I).

The starting compounds for the preparation of compounds of formula (I) and related formulae are generally known. If they are novel, they can, however, be prepared by methods known per se.

The reactions are preferably carried out in an inert solvent.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

In another aspect, the invention relates to a mixture of several compounds of formula (I), preferably a mixture of 2 to 10 compounds, more preferably, a mixture of 2 or 3 compounds of Formula (I). In another aspect, the invention may also encompass isomers, stereoisomers, diasteroisomers, enentiomers, as well as geometric isomers of compounds of Formula (I).

The invention also encompasses mixtures of isomers, e.g. stereoisomers, diasteroisomers, enentiomers and geometric isomers, of compounds of Formula (I).

In a further aspect, the invention provides pharmaceutically acceptable derivatives, solvates, tautomers, salts and stereoisomers of Formula (I).

Accordingly, the invention relates, in particular, to the use of formula (I) and related formulae as defined above, as a medicament.

Accordingly, the invention relates, in particular, to the use of compounds of the formula (I) and related formulae as defined above, for the preparation of pharmaceutical formulations for the prevention and/or the treatment of multiple sclerosis, cancers and related disorders.

The said compounds of the formula (I) and related formulae can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula I and related formulae contains an acidic center, such as a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example sodium- or potassium methoxide and sodium or potassium-propoxide, alkalihydrides, such as sodium- or potassiumhydride; and various organic bases, such as piperidine, diethanolamine and N-methyl-glutamine, benzathine, choline, diethanolamine, ethylenediamine, meglumine, benethamine, diethylamine, piperazine and tromethamine. The aluminium salts of the compounds of the formula (I) and related formulae are likewise included. In the case of certain compounds of the formula I and related formulae, which contain a basic center, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzene-sulfonate, and other organic acids and corresponding salts thereof, such as acetate, trifluoro-acetate, tartrate, maleate, succinate, citrate, benzoate, salicylate, ascorbate and the like. Accordingly, pharmaceutically acceptable acid-addition salts of the compounds of the formula I and related formulae include the following: acetate, adipate, alginate, arginate, aspartate, benzoate, benzene-sulfonate (besylate), bisulfate, bisulfite, bromide, butyrate, camphorate, camphor-sulfonate, caprylate, chloride, chlorobenzoate, citrate, cyclopentane-propionate, digluconate, dihydrogen-phosphate, dinitrobenzoate, dodecyl-sulfate, ethanesulfonate, fumarate, galacterate (from mucic acid), galacturonate, glucoheptanoate, gluco-nate, glutamate, glycerophosphate, hemi-succinate, hemisulfate, heptanoate, hexanoate, hippurate, hydrochloride, hydrobromide, hydroiodide, 2-hydroxy-ethanesulfonate, iodide, isethionate, isobutyrate, lactate, lactobionate, malate, maleate, malonate, mandelate, metaphosphate, methanesulfonate, methylbenzoate, mono-hydrogen-phosphate, 2-naphthalenesulfonate, nicotinate, nitrate, oxalate, oleate, palmo-ate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula (I) and related formulae include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanol-amine, diethyl-amine, 2-diethyl-aminoethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanol-amine, triethylamine, trimethylamine, tripropyl-amine and tris(hydroxy-methyl)-methylamine (tromethamine), but this is not intended to represent a restriction.

Compounds of the formula (I) and related formulae of the present invention which contain basic nitrogen-containing groups can be quaternised using agents such as $(C_1-C_4)$-alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, do-decyl, lauryl, myristyl and stearyl chloride, bromide and iodide; and aryl-$(C_1-C_4)$alkyl halides, for example benzyl chloride and phenethyl bromide. Both water- and oil-soluble compounds of the formula I can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, me-glumine, nitrate, oleate, phosphonate, pivalate, sodium phosphate, stea-rate, sulfate, sulfosalicylate, tartrate, thiomalate, tosylate and tro-meth-amine, but this is not intended to represent a restriction.

The acid-addition salts of basic compounds of the formula (I) and related formulae are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts other-wise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanol-amine, ethylenediamine, N-methyl-D-glucamine and procaine.

The base-addition salts of acidic compounds of the formula I and related formulae are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts other-wise correspond to the respective free acid forms thereof.

If a compound of the formula (I) and related formulae contains more than one group which is capable of forming pharmaceutically acceptable salts of this type, the formula (I) also encompasses multiple salts. Typical multiple salt forms include, for example, bitartrate, diacetate, difumarate, dimeglumine, di-phosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula (I) and related formulae in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The term "leaving group" or "leaving groups" denotes an atom or a group of atoms easily cleaved, hydrolysed or substituted with a reagent. Preferred leaving groups are halogens, alkylsulfonates, arylsulfonates, alcoholates or activated esters.

The term "reducing agent" denotes a reagent able to donate electrons. Preferred reducing agents are Boranes, Catecholborane, Copper hydride, Copper (low valent), Chromium (low valent), Decaborane, DIBAL-H, Diborane, Diethyl 1,4-dihydro-2,6-dimethyl-3,5-pyridinedicarboxylate, Diisobutylaluminium hydride, Dimethylsulfide borane, DMSB, Fe, Formaldehyde, Formic acid, Hantzsch Ester, Hydrazine, Hydrogen, Indium (low valent), Iron, Isopropanol, LAH, Lithium, Lithium aluminum hydride, Lithium tetrahydridoaluminate, LiBH4, Magnesium, Manganese, 3-Mercaptopropionic acid, 3-MPA, Neodymium (low valent), Nickel, Nickel borohydride, Niobium (low valent), Phenylsilane, PMHS, Polymethylhydrosiloxane, Potassium, 2-Propanol, Red-Al, Rongalite, Samarium (low valent), Silanes, Sodium, Sodium bis(2-methoxyethoxy)aluminumhydride, Sodium borohydride, Sodium cyanoborohydride, Sodium dithionite, Sodium hydrosulfite, Sodium hydroxymethanesulfinate, Sodium tetrahydroborate, Sodium triacetoxyborohydride, Strontium, Tetramethyldisiloxane, Tin hydrides, Titanium (low valent), TMDSO, Tributylstannane, Tributyltin hydride, Trichlorosilane, Triphenylphosphine, Triphenylphosphite, Triethylsilane, Tris(trimethylsilyl)silane, TTMSS, Zinc.

The term "prodrug derivatives" or "prodrug" is taken to mean compounds of the formula (I) which have been modified with, for example, alkyl or acyl groups, sugars or oligopeptides and which are rapidly cleaved in the organism to form the active compounds. These also include biodegradable polymer derivatives of the compounds according to the invention, as described, for example, in Int. J. Pharm. 115, 61-67 (1995).

Owing to their molecular structure, the compounds of the formula (I) and related formulae can be chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of compounds of Formula (I) for the manufacture of a medicament for the prevention and/or the treatment of the diseases associated to Phosphoinositide 3-kinases disorders.

The invention also relates to the use of compounds of Formula (I) for the manufacture of a medicament for the prevention and/or the treatment of multiple sclerosis, cancers, autoimmune disorder, and related disorders.

The invention also relates to the use of compounds of Formula (I) for the manufacture of a medicament for the prevention and/or the treatment of the disease selected from the group consisting of amyotrophic lateral sclerosis (ALS), systemic lupus erythematosus, chronic rheumatoid arthritis, inflammatory bowel disease, psoriasis, autoimmune myositis, Wegener's granulomatosis, ichthyosis, bone marrow or organ transplant rejection or graft-versus-host disease, Hashimoto's thyroiditis, myasthenia gravis, uveitis, posterior uveitis, rheumatic fever inflammatory and hyperproliferative skin diseases, atopic dermatitis, contact dermatitis, areata, keratoconjunctivitis, autoimmune hemolytic anemia, agranulocytosis, cutaneous T cell lymphoma, chronic lymphocytic leukemia, arteriosclerosis, atherosclerosis, aortitis syndrome, polyarteritis nodosa, lung cancer, carcinogenesis, metastasis of carcinoma and hypobaropathy, disease caused by histamine or leukotriene-C4 release, autoimmune hepatitis, primary biliary cirrhosis, Parkinson's disease.

The invention furthermore relates to the use of compounds of formula (I) and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene; methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonabcd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes. The invention furthermore relates to the use of compounds of formula I and related formulae in combination with at least one further medicament active ingredient, preferably medicaments used in the treatment of cancer wherein said antitumoral compounds are selected from those well known by the one skilled in the related art. These compositions can be used as medicaments in human and veterinary medicine.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and related formulae and salts, solvates and physiologically functional derivatives thereof and the other active ingredients can also be administered in the form of liposome delivery systems, such as, for exam-ple, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention furthermore relates to a method for treating a subject suffering from a PI3K related disorder, comprising administering to said subject an effective amount of a compound of formula I and related formulae. The present invention preferably relates to a method, wherein the PI3Kassociated disorder is an autoimmune disorder or condition associated with an overactive immune response or cancer. The present invention furthermore relates to a method of treating a subject suffering from an immunerogulatory abnormality, comprising administering to said subject a compound of formula (I) and related formulae in an amount that is effective for treating said immunoregulatory inhibitors. The present invention preferably relates to a method wherein the immunoregulatory abnormality is an autoimmune or chronic inflammatory disease selected from the group consisting of: amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma. The present invention furthermore relates to a method wherein the immunoregulatory abnormality is bone marrow or organ transplant rejection or graft-versus-host disease. The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, aneryrthroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, and chronic bacterial infection.

Preferred compounds of formula (I) and related formulae exhibit a $IC_{50}$ for the binding to PI3K of less than about 5 μM, preferably less than about 1 μM and even more preferably less than about 0.100 μM.

Compounds according to formula (I) and related formulae may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In general, the synthesis pathways for any individual compound of formula (I) and related formulae will depend on the specific substitutents of each molecule and upon the ready availability of intermediates necessary; again such factors being appreciated by those of ordinary skill in the art.

Compounds of this invention can be isolated in association with solvent molecules by crystallization from evaporation of an appropriate solvent. The pharmaceutically acceptable acid addition salts of the compounds of formula (I) and related formulae which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula (I) and related formulae, which contain an acid center, with a suitable base. Both types of salts may be formed or interconverted using ion-exchange resin techniques.

In the following the present invention shall be illustrated by means of some examples, which are not construed to be viewed as limiting the scope of the invention.

EXPERIMENTAL PART

Nomenclature of the compounds of this invention has been determined using ACD/Name Version 7.0 software.

The commercially available starting materials used in the following experimental description were purchased from Sigma-Aldrich-Fluka unless otherwise reported. However, specific reagents were purchased from other suppliers: 3-fluoro-5-hydroxyphenyl boronic acid (Combiblock), indole-4-boronic acid (Combiblock), 3-methoxymethyl-phenyl boronic acid (Frontier).

NMR, HPLC and MS data provided in the examples described below are registered on: NMR: Bruker DPX-300 MHz or 400 MHz, using residual signal of deuterated solvent as internal reference.

HPLC: (Method A) column Atlantis C18 (5 μm 4.6×75 mm), conditions: solvent A ($H_2O$ with 0.1% TFA), solvent B (ACN), gradient 5% B to 100% B over 8 min, UV detection. (Method B) column Waters XBridge C8 (3.5 μm 4.6×50 mm), conditions: solvent A ($H_2O$ with 0.1% TFA), solvent B (ACN with 0.05% TFA), gradient 5% B to 100% B over 8 min, UV detection. LC/MS: (Method A) column XBridge C8 (3.5 μm 4.6×50 mm), conditions: solvent A ($H_2O$ with 0.1% TFA) solvent B (ACN with 0.1% TFA), gradient 5% B to 100% B over 8 min, UV detection. MS (ES positive and negative mode). (Method B) Column Waters BEH C18 (1.7 μm 2.1×50 mm), conditions: solvent A (10 mM ammonium acetate in water+5% ACN), solvent B (ACN), gradient 5% B to 100% B over 3 min. MS (ES positive and negative mode).

The microwave chemistry is performed on a single mode microwave reactor Emrys™ Optimiser from Personal Chemistry.

Mass triggered preparative HPLC is performed on a mass directed autopurification Fractionlynx system from Waters equipped with a Sunfire Prep C18 OBD column 19×100 mm 5 μm, unless otherwise reported. All HPLC purifications were performed with a gradient of $ACN/H_2O$ or $ACN/H_2O$/HCOOH (0.1%).

General Procedure A

A suspension of a 4-methylthio-pyrido[3,2-d]pyrimidine derivative (1 eq.), a boronic acid (2 eq.), CuTC (2 eq.) and $Pd(PPh_3)_4$ (0.05 to 0.1 eq.) in dry and degassed dioxane was stirred at 55° C. for 16 hours under nitrogen. The reaction mixture was then concentrated in vacuo, the residue taken up in DCM, washed successively with 10% sodium bicarbonate, water and brine, dried over sodium sulfate and concentrated in vacuo.

Intermediate 1

Dimethyl (2E)-2-[(2,4-dioxo-1,2,3,4-tetrahydropyrimidin-5-yl)amino]but-2-enedioate

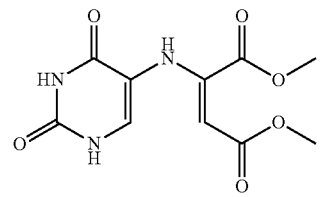 [SMILES: COC(=O)/C=C(/Nc1c[nH]c(=O)[nH]c1=O)C(=O)OC]

To a suspension of 5-aminouracil (275 g, 2.16 mol) in dry methanol (5.5 L) was added dropwise dimethyl acetylene dicarboxylate (344 g, 2.42 mol) at room temperature. After the end of the addition, the mixture was stirred at room temperature for 24 hours. The precipitate was filtered off, washed with MeOH (500 mL) and dried under vacuum to afford the title compound (430 g, 74%) as a yellow solid.

LC/MS (Method A): RT 0.87 min (purity: 96%). MS (ES−): 267.6.

$^1$H NMR (400 MHz, DMSO-d$_6$) δ 11.33 (br s, 1H), 10.82 (br s, 1H), 9.07 (s, 1H), 7.42 (s, 1H), 5.21 (s, 1H), 3.65 (s, 3H), 3.63 (s, 3H).

Intermediate 2

Methyl 2,4,8-trioxo-1,2,3,4,5,8-hexahydropyrido[3,2-d]pyrimidine-6-carboxylate

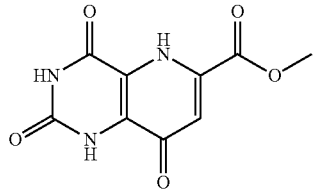 [SMILES: COC(=O)c1cc(=O)c2[nH]c(=O)[nH]c(=O)c2[nH]1]

A suspension of Intermediate 1 (50 g, 0.182 mol) in Dowtherm® A (1 L) was refluxed for 1 hour. The reaction mixture was cooled to room temperature and diluted with PE (2 L). The precipitate was filtered, washed with PE (1 L) and dried under vacuum. The crude product was slurred in DMF (200 mL) and the insoluble material was collected by filtration to afford the title compound as a brown solid.

LC/MS (Method A): RT 0.77 min (purity: 83%). MS (ES−): 235.8.

$^1$H NMR (400 MHz, DMSO-d$_6$) δ 12.05 (br s, 1H), 11.57 (br s, 1H), 10.91 (br s, 1H), 7.57 (s, 1H), 3.86 (s, 3H).

Intermediate 3

Methyl 2,4,8-trichloropyrido[3,2-d]pyrimidine-6-carboxylate

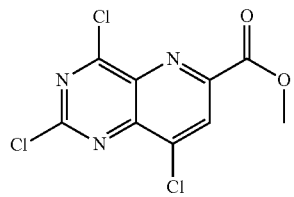 [SMILES: COC(=O)c1cc(Cl)c2nc(Cl)nc(Cl)c2n1]

To a suspension of Intermediate 2 (10 g, 42.2 mmol) in phosphorous oxychloride (250 mL) was added dropwise N,N-diethylaniline (10 mL) at room temperature. After the end of the addition, the mixture was refluxed for 18 hours then concentrated in vacuo to ca. 50 mL. The residue was poured onto ice/water (1 L) and the solid was filtered off, washed with water and dried to afford the title compound (10 g, 81%) as a brown solid.

LC/MS (Method A): RT 1.52 min (purity: 87%). MS (ES+): 293.1.

$^1$H NMR (400 MHz, DMSO-d$_6$) δ 8.46 (s, 1H), 3.93 (s, 3H).

Intermediate 4

Methyl 2,8-dichloro-4-(methylthio)pyrido[3,2-d]pyrimidine-6-carboxylate

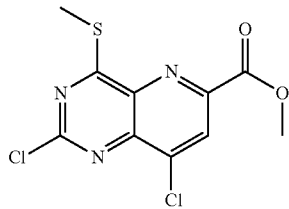 [SMILES: COC(=O)c1cc(Cl)c2nc(Cl)nc(SC)c2n1]

To a suspension of Intermediate 3 (5 g, 17 mmol) in dry dichloromethane (150 mL) was added sodium thiomethoxide (1.2 g, 17 mmol) in portions at −10° C. over a period of 15 min. The reaction mixture was stirred at −10° C. for 3 hours, then quenched by addition of water (2 mL). The precipitate was filtered off, washed with water (2×100 mL) then brine (100 mL), and dried in vacuo. The crude solid was slurred in methanol (100 mL), filtered off and dried to afford the title compound as a brown solid, which was used without further purification.

LC/MS (method A): RT=2.45 min (purity: 83%). MS (ES+): 305.8. $^1$H NMR (400 MHz, DMSO-d$_6$): δ 8.63 (s, 1H), 3.97 (s, 3H), 2.65 (s, 3H).

HPLC (Method A): RT=4.07 min (purity: 96%).

Intermediate 5

Methyl 8-chloro-4-(methylthio)-2-morpholin-4-ylpyrido[3,2-d]pyrimidine-6-carboxylate

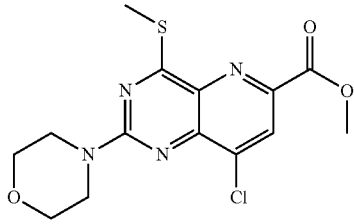 [SMILES: COC(=O)c1cc(Cl)c2nc(N3CCOCC3)nc(SC)c2n1]

Morpholine (1.54 mL, 17.6 mmol) was added to a suspension of Intermediate 4 (5.0 g, 16 mmol) and DIEA (5.73 mL, 33 mmol) in ACN (150 mL) at 0° C. over 10 minutes and the reaction mixture was stirred for a further 12 hours. The precipitate was filtered off, washed with cold methanol (20 mL) and dried to afford the title compound (5 g, 85%) as a brownish solid.

LC/MS (method A): RT=4.88 min (purity: 98%). MS (ES+): 355.1

$^1$H NMR (400 MHz, CDCl$_3$): δ 8.38 (s, 1H), 4.10-4.45 (m, 4H), 4.02 (s, 3H), 3.85-3.83 (m, 4H), 2.60 (s, 3H).

HPLC (Method A): RT=5.58 min (purity: 98%).

Intermediate 6

Methyl 8-chloro-4-(3-methoxyphenyl)-2-morpholin-4-ylpyrido[3,2-d]pyrimidine-6-carboxylate

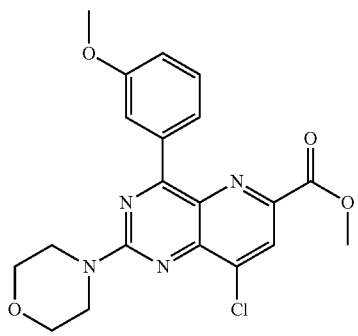 [SMILES: COC(=O)c1cc(Cl)c2nc(N3CCOCC3)nc(-c3cccc(OC)c3)c2n1]

Intermediate 4 (500 mg, 1.64 mmol), 3-methoxybenzeneboronic acid (500 mg, 3.3 mmol), CuTC (627 mg, 3.3 mmol) and Pd(PPh$_3$)$_4$ (95 mg, 0.08 mmol) were reacted in dioxane (20 mL) according to General Procedure A. Purification by trituration in MeOH and filtration afforded the crude dichloro derivative a brownish solid. The solid was suspended in ACN (15 mL) and morpholine (358 mg, 4.11 mmol) was added dropwise. The reaction mixture was stirred at room temperature for 1 hour then concentrated in vacuo. The residue was taken up in DCM, washed with sat. aq. NH$_4$Cl then brine, dried over magnesium sulfate and concentrated in vacuo to afford the title compound as a yellow solid.

LC/MS (method B): RT=1.70 min (purity: 98%). MS (ES+): 415.1

$^1$H NMR (300 MHz, CDCl$_3$): δ 8.33 (s, 1H), 8.23 (t, J=2.0 Hz, 1H), 7.95 (d, J=7.8 Hz, 1H), 7.46 (t, J=8.0 Hz, 1H), 7.18 (dd, J=7.8, 2.0 Hz, 1H), 4.00 (br s, 4H), 3.90 (s, 3H), 3.87 (s, 3H), 3.75 (br t, J=4.8 Hz, 4H).

HPLC (Method B): RT=4.98 min (purity: 98%).

Intermediate 7

Methyl 4-(3-methoxyphenyl)-2-morpholin-4-ylpyrido[3,2-d]pyrimidine-6-carboxylate

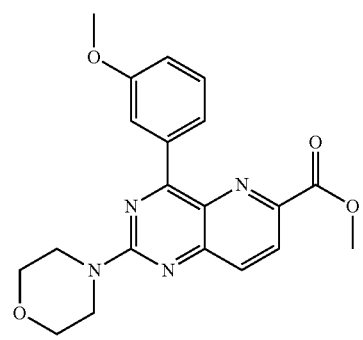 [SMILES: COC(=O)c1ccc2nc(N3CCOCC3)nc(-c3cccc(OC)c3)c2n1]

A mixture of Intermediate 6 (100 mg, 0.24 mmol), ammonium formate (304 mg, 4.82 mmol) and 5% pd/C (20 mg) in EtOH (20 mL) was stirred at reflux for 60 min. The reaction mixture was filtered through a short plug of Celite® and the resulting yellow solution was concentrated in vacuo. The solid residue was taken up in DCM and MnO$_2$ (5 g) was added. The resulting mixture was stirred at 50° C. for 3 hours then at room temperature for 15 hours. The suspension was filtered through a short plug of Celite®, and the solution was concentrated in vacuo. The residue was suspended in MeOH, stirred at 60° C. for 5 minutes, allowed to return to room temperature and the precipitate collected by filtration to afford the title compound (67 mg, 73%) as a yellow solid.

LC/MS (method B): RT=1.49 min (purity: 98%). MS (ES+): 381.2.

$^1$H NMR (300 MHz, CDCl$_3$): δ 8.29 (dd, J=2.5, 1.5 Hz, 1H), 8.26 (d, J=8.9 Hz, 1H), 8.04 (d, J=8.9 Hz, 1H), 7.99 (dt, J=7.8, 1.5 Hz, 1H), 7.48 (t, J=8.1 Hz, 1H), 7.18 (dd, J=8.2, 2.6 Hz, 1H), 4.01-3.94 (m, 4H), 3.91 (s, 3H), 3.89 (s, 3H), 3.74 (br t, J=4.7 Hz, 4H).

HPLC (Method B): RT=3.98 min (purity: 97%).

Intermediate 8

Methyl 8-chloro-4-(4-hydroxy-phenyl)-2-morpholin-4-yl-pyrido[3,2-d]pyrimidine-6-carboxylate

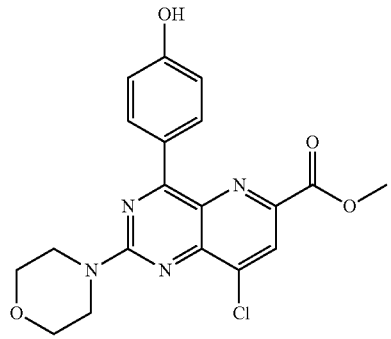 [SMILES: COC(=O)c1cc(Cl)c2nc(N3CCOCC3)nc(-c3ccc(O)cc3)c2n1]

Intermediate 5 (2 g, 5.6 mmol), 4-hydroxy phenyl boronic acid (1.54 g, 11 mmol), CuTC (2.13 g, 11 mmol) and Pd(PPh$_3$)$_4$ (0.51 g, 0.4 mmol) were reacted in dioxane (100 mL) according to General Procedure A. Purification by column chromatography (CHCl$_3$/MeOH, 9/1) afforded the title compound as a yellow solid.

LC/MS (method A): RT=4.79 min (purity: 96%). MS (ES+): 400.8

$^1$H NMR (400 MHz, DMSO-d$_6$): δ 10.23 (br s, 1H), 8.50 (d, J=8.8 Hz, 2H), 8.33 (s, 1H), 6.92 (d, J=8.8 Hz, 2H), 4.10-3.90 (m, 4H), 3.92 (s, 3H), 3.75-3.73 (m, 4H).

HPLC (Method A): RT=5.33 min (purity: 96%).

Intermediate 9

8-Chloro-4-(4-hydroxy-phenyl)-2-morpholin-4-yl-pyrido[3,2-d]pyrimidine-6-carboxylic acid

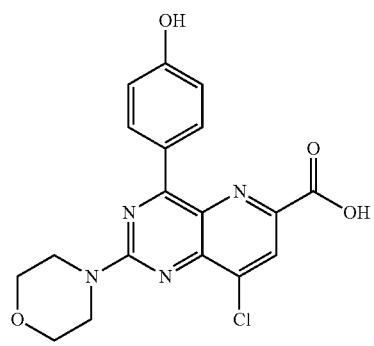

To a solution of Intermediate 8 (1.0 g, 2.5 mmol) in a mixture of methanol/THF/water (3/2/1, 30 mL), lithium hydroxide (0.18 g, 7.5 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.95 g, 98%) as a yellow solid.

LC/MS (method A): RT=3.56 min (purity: 91%). MS (ES+): 387.1.

Intermediate 10

Methyl 4-(4-hydroxy-phenyl)-2-morpholin-4-yl-pyrido[3,2-d]pyrimidine-6-carboxylate

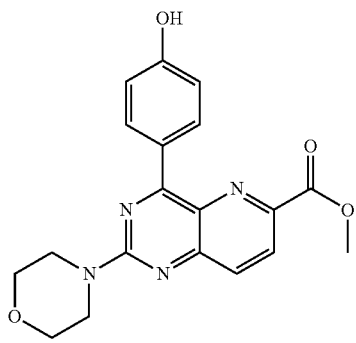 [SMILES: COC(=O)c1ccc2nc(N3CCOCC3)nc(-c3ccc(O)cc3)c2n1]

A mixture of Intermediate 8 (0.1 g, 0.24 mmol), ammonium formate (0.31 g, 4.9 mmol) and 10% Pd/C (10 mg) in EtOH (20 mL), was stirred at reflux for 24 hours. After filtration through a short plug of Celite®, the solution was concentrated in vacuo and the residue washed with Et$_2$O to afford the title compound (74 mg, 84%) as a yellow solid.

LC/MS (method A): RT=4.18 min (purity: 96%). MS (ES+): 367.4

$^1$H NMR (400 MHz, DMSO-d$_6$): δ 8.55 (d, J=8.8 Hz, 2H), 8.21 (d, J=8.8 Hz, 1H), 7.97 (d, J=8.8 Hz, 1H), 6.93 (J=8.8 Hz, 2H), 3.97-3.93 (m, 4H), 3.91 (S, 3H), 3.73-3.72 (m, 4H).

Intermediate 11

Methyl 8-chloro-4-(3-hydroxy-phenyl)-2-morpholin-4-yl-pyrido[3,2-d]pyrimidine-6-carboxylate

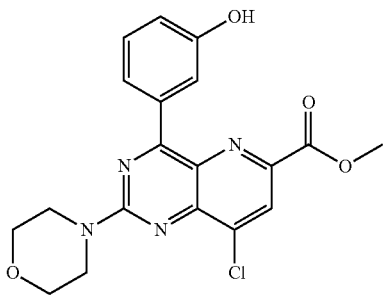 [SMILES: COC(=O)c1cc(Cl)c2nc(N3CCOCC3)nc(-c3cccc(O)c3)c2n1]

Intermediate 5 (5.0 g, 14.1 mmol), 3-hydroxy phenyl boronic acid (3.89 g, 28.2 mmol), CuTC (5.37 g, 28.2 mmol) and Pd(PPh$_3$)$_4$ (1.15 g, 0.7 mmol) in dioxane (300 mL) were reacted according to General Procedure A. Purification column chromatography (CHCl$_3$/MeOH, 9/1) afforded the title compound as a yellow solid.

LC/MS (method A): RT=4.78 min (purity: 91%). MS (ES+): 401.1

$^1$H NMR (400 MHz, DMSO-d$_6$): δ 9.66 (s, 1H), 8.36 (s, 1H), 7.85-7.82 (m, 1H), 7.73-7.72 (m, 1H), 7.36-7.32 (m, 1H), 7.01-6.99 (m, 1H) 4.10-3.90 (m, 4H), 3.90 (s, 3H), 3.76-3.74 (m, 4H).

HPLC (Method A): RT=4.75 min (purity: 99%).

Intermediate 12

Methyl 8-chloro-4-(3-fluoro-5-hydroxy-phenyl)-2-morpholin-4-yl-pyrido[3,2-d]pyrimidine-6-carboxylate

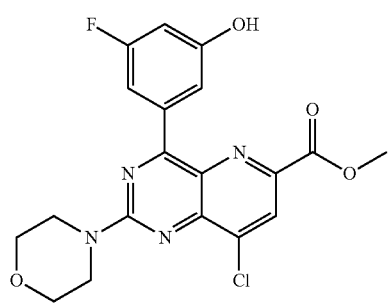 [SMILES: COC(=O)c1cc(Cl)c2nc(N3CCOCC3)nc(-c3cc(O)cc(F)c3)c2n1]

Intermediate 5 (2 g, 5.6 mmol), 3-fluoro-5-hydroxy phenyl boronic acid (1.74 g, 11 mmol), CuTC (2.13 gm, 11 mmol) and Pd(PPh$_3$)$_4$ (0.51 g, 0.4 mmol) in dioxane (100 mL) were reacted according to General Procedure A. Purification column chromatography (n-hexane/ethyl acetate, 1/1) afforded the title compound as a yellow solid.

LC/MS (method A): RT=5.02 min (purity: 97%). MS (ES+): 419.0

$^1$H NMR (400 MHz, DMSO-d$_6$): δ 10.19 (s, 1H), 8.36 (s, 1H), 7.77 (dd, J=1.4, 9.0 Hz, 1H), 7.65 (d, J=1.4 Hz, 1H), 6.83-6.79 (m, 1H), 4.10-3.90 (m, 4H), 3.91 (s, 3H), 3.76-3.74 (m, 4H).

HPLC (Method A): RT=5.03 min (purity: 96%).

Intermediate 13

8-Chloro-4-(3-fluoro-5-hydroxy-phenyl)-2-morpholin-4-yl-pyrido[3,2-d]pyrimidine-6-carboxylic acid

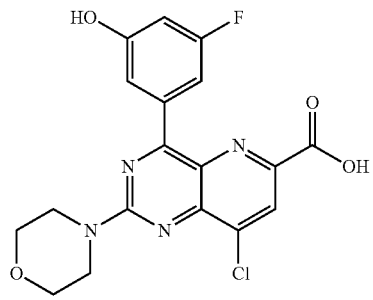

To a solution of Intermediate 12 (1.0 g, 2.4 mmol) in a mixture of methanol/THF/water (3/2/1, 30 mL), lithium hydroxide (0.17 g, 7.2 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.75 g, 78%) as a yellow solid.

LC/MS (method A): RT=4.34 min (purity: 99%). MS (ES+): 405.0.

$^1$H NMR (400 MHz, DMSO-$d_6$): δ 13.50 (br s, 1H), 10.17 (s, 1H), 8.35 (s, 1H), 7.83-7.80 (m, 1H), 7.69-7.66 (m, 1H), 6.82-6.80 (m, 1H), 4.04-3.99 (m, 4H), 3.76-3.74 (m, 4H).

Intermediate 14

Methyl 8-chloro-4-(1H-indol-4-yl)-2-morpholin-4-yl-pyrido[3,2-d]pyrimidine-6-carboxylate

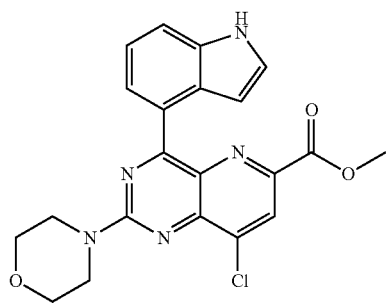 [SMILES: COC(=O)c1cc(Cl)c2nc(N3CCOCC3)nc(-c3cccc4[nH]ccc34)c2n1]

Intermediate 5 (5 g, 14.1 mmol), indole-4-boronic acid (4.53 g, 28.2 mmol), CuTC (5.37 g, 28.2 mmol) and Pd(PPh$_3$)$_4$ (1.15 g, 1 mmol) in dioxane (300 mL) were reacted according to General Procedure A. Purification by column chromatography (CHCl$_3$/MeOH, 9/1) afforded the title compound as a yellow solid.

LC/MS (method A): RT=5.08 min (purity: 99%). MS (ES+): 423.9

$^1$H NMR (400 MHz, DMSO-$d_6$): δ 11.38 (s, 1H), 8.36 (d, J=1.0 Hz, 1H), 7.83 (t, J=6.7 Hz, 1H), 7.63 (d, J=8.0 Hz, 1H), 7.48 (t, J=2.8 Hz, 1H), 7.24 (t, J=7.8 Hz, 1H), 6.74 (d, J=2.0 Hz, 1H), 4.03-4.00 (m, 4H), 3.85 (s, 3H), 3.77-3.75 (m, 4H).

HPLC (Method A): RT=5.11 min (purity: 97%).

Intermediate 15

8-Chloro-4-(1H-indol-4-yl)-2-morpholin-4-yl-pyrido[3,2-d]pyrimidine-6-carboxylic acid

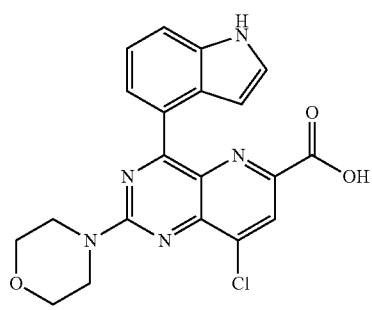 [SMILES: O=C(O)c1cc(Cl)c2nc(N3CCOCC3)nc(-c3cccc4[nH]ccc34)c2n1]

To a solution of Intermediate 14 (1.0 g, 2.3 mmol) in a mixture of methanol/THF/water (3/2/1, 30 mL), lithium hydroxide (0.19 g, 7.4 mmol) was added. The reaction mixture was stirred at 90° C. for 1 hour then concentrated in vacuo. The residue was dissolved in water (5 mL) and neutralized with 20% aqueous citric acid. The aqueous layer was then extracted with ethyl acetate (3×50 mL), the combined organic phase washed with water (50 mL) and brine (50 mL) and dried over sodium sulfate to afford, after evaporation, the title compound (0.95 g, 98%) as a yellow solid.

LC/MS (method A): RT=4.40 min (purity: 98%). MS (ES+): 409.9

$^1$H NMR (400 MHz, DMSO-$d_6$): δ 13.33 (br s, 1H), 11.35 (s, 1H) 8.34 (s, 1H), 7.86 (d, J=7.4 Hz, 1H), 7.62 (d, J=8.0 Hz, 1H), 7.48 (t, J=2.6 Hz, 1H), 7.24 (t, J=7.7 Hz, 1H), 6.74 (s, 1H), 4.04-3.99 (m, 4H), 3.77-3.76 (m, 4H).

HPLC (Method A): RT=4.42 min (purity: 99%).

Intermediate 16

Methyl 8-chloro-4-(1H-indol-5-yl)-2-morpholin-4-yl-pyrido[3,2-d]pyrimidine-6-carboxylate

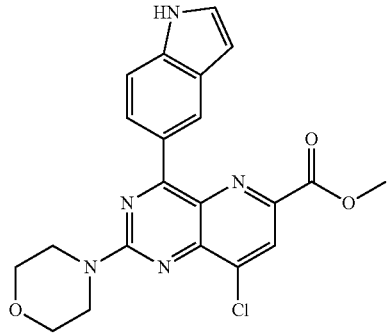 [SMILES: COC(=O)c1cc(Cl)c2nc(N3CCOCC3)nc(-c3ccc4[nH]ccc4c3)c2n1]

Intermediate 5 (4 g, 11 mmol), indole-5-boronic acid (3.6 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by column chromatography (CHCl$_3$/MeOH, 9/1)afforded the title compound as a yellow solid.

LC/MS (method A): RT=5.21 min (purity: 98%). MS (ES+): 423.9

$^1$H NMR (400 MHz, DMSO-$d_6$): δ 11.41 (br s, 1H), 8.96 (s, 1H), 8.35 (s, 1H), 8.27 (d, J=8.6 Hz, 1H), 7.52 (d, J=8.6 Hz, 1H), 7.46 (t, J=2.5 Hz, 1H), 6.60 (s, 1H), 4.06-4.00 (m, 4H), 3.92 (s, 3H), 3.77-3.75 (m, 4H).

HPLC (Method A): RT=5.22 min (purity: 98%).

Intermediate 17

8-Chloro-4-(1H-indol-5-yl)-2-morpholin-4-yl-pyrido[3,2-d]pyrimidine-6-carboxylic acid

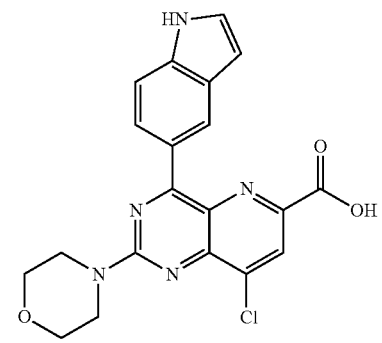 [SMILES: O=C(O)c1cc(Cl)c2nc(N3CCOCC3)nc(-c3ccc4[nH]ccc4c3)c2n1]

To a solution of Intermediate 16 (1.2 g, 2.8 mmol) in a mixture of methanol/THF/water (3/2/1, 30 mL), lithium hydroxide (0.2 g, 8.5 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (1 g, 86%) as a yellow solid.

LC/MS (method A): RT=4.48 min (purity: 93%). MS (ES+): 409.9.

Intermediate 18

Methyl 8-chloro-4-(4-hydroxymethyl-phenyl)-2-morpholin-4-yl-pyrido[3,2-d]pyrimidine-6-carboxylate

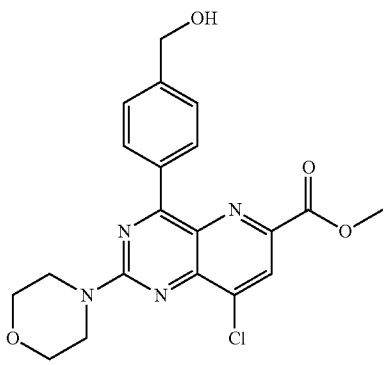 [SMILES: COC(=O)c1cc(Cl)c2nc(N3CCOCC3)nc(-c3ccc(CO)cc3)c2n1]

Intermediate 5 (5 g, 14 mmol), 4-(hydroxy methyl)-phenyl boronic acid (4.28 g, 28.2 mmol), CuTC (5.37 g, 28.2 mmol), and Pd(PPh₃)₄ (1.15 g, 1 mmol) in dioxane (300 mL) were reacted according to General Procedure A. Purification by column chromatography (CHCl₃/MeOH, 9/1) afforded the title compound as a yellow solid.

LC/MS (method A): RT=4.58 min (purity: 98%). MS (ES+): 415.1

$^1$H NMR (400 MHz, DMSO-$d_6$): δ 8.37-8.35 (m, 3H), 7.49 (d, J=8.4 Hz, 2H), 5.37 (t, J=5.8 Hz, 1H), 4.62 (d, J=5.7 Hz, 2H), 4.06-3.96 (m, 4H), 3.90 (s, 3H), 3.76-3.74 (m, 4H).

HPLC (Method A): RT=4.55 min (purity: 96%).

Intermediate 19

8-Chloro-4-(4-hydroxymethyl-phenyl)-2-morpholin-4-yl-pyrido[3,2-d]pyrimidine-6-carboxylic acid

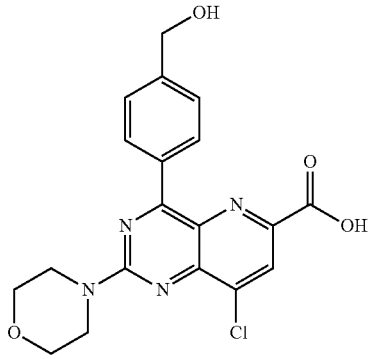 [SMILES: O=C(O)c1cc(Cl)c2nc(N3CCOCC3)nc(-c3ccc(CO)cc3)c2n1]

To a solution of Intermediate 18 (1.0 g, 2.4 mmol) in a mixture of methanol/THF/water (3/2/1, 30 mL), lithium hydroxide (0.17 g, 7.2 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.7 g, 72%) as a yellow solid.

LC/MS (method A): RT=3.89 min (purity: 96%). MS (ES+): 400.8.

Intermediate 20

Methyl 8-chloro-4-(3-hydroxymethyl-phenyl)-2-morpholin-4-yl-pyrido[3,2-d]pyrimidine-6-carboxylate

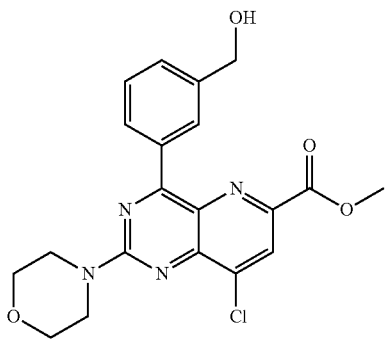 [SMILES: COC(=O)c1cc(Cl)c2nc(N3CCOCC3)nc(-c3cccc(CO)c3)c2n1]

Intermediate 5 (4 g, 11 mmol), 3-(hydroxymethyl)phenyl boronic acid (3.4 g, 22 mmol), CuTC (4.26 g, 22 mmol) and Pd(PPh₃)₄ (1.02 g, 0.8 mmol) in dry dioxane (200 mL) were reacted according to General Procedure A. Purification by column chromatography (CHCl₃/MeOH, 9/1) afforded the title compound as a yellow solid.

LC/MS (method A): RT=4.55 min (purity: 95%). MS (ES+): 414.8

$^1$H NMR (400 MHz, DMSO-$d_6$): δ 8.35-8.33 (m, 2H), 8.24 (d, J=7.7 Hz, 1H), 7.57 (d, J=7.6 Hz, 1H), 7.51 (t, J=7.6 Hz, 1H), 5.32 (t, J=5.8 Hz, 1H), 4.61 (d, J=5.7 Hz, 2H), 4.05-3.97 (m, 4H), 3.89 (s, 3H), 3.76-3.74 (m, 4H).

HPLC (Method A): RT=4.54 min (purity: 97%).

Intermediate 21

8-Chloro-4-(3-hydroxymethyl-phenyl)-2-morpholin-4-yl-pyrido[3,2-d]pyrimidine-6-carboxylic acid

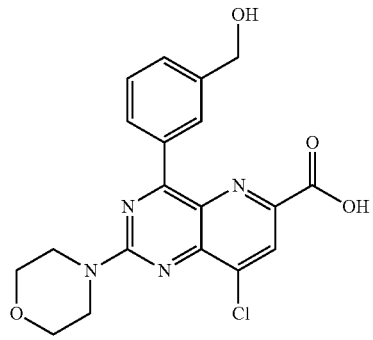 [SMILES: O=C(O)c1cc(Cl)c2nc(N3CCOCC3)nc(-c3cccc(CO)c3)c2n1]

To a solution of Intermediate 20 (1.0 g, 2.4 mmol) in a mixture of methanol/THF/water (3/2/1, 30 mL), lithium hydroxide (0.17 g, 7.2 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.85 g, 87%) as a yellow solid.

LC/MS (method A): RT=3.82 min (purity: 94%). MS (ES+): 400.8.

$^1$H NMR (400 MHz, DMSO-$d_6$): δ 13.40 (br s, 1H), 8.35 (s, 1H), 8.29-8.28 (m, 2H), 7.57-7.49 (m, 2H), 5.30 (t, J=5.6 Hz, 1H), 4.60 (d, J=5.3 Hz, 2H), 4.01 (m, 4H), 3.75 (t, J=4.7 Hz, 4H).

HPLC (Method A): RT=3.83 min (purity: 94%).

Intermediate 22

Methyl 8-chloro-4-(3-methoxymethyl-phenyl)-2-morpholin-4-yl-pyrido[1,2-d]pyrimidine-6-carboxylate

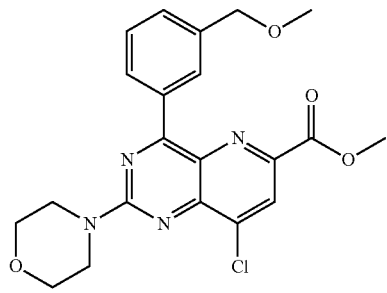 [SMILES: COCc1cccc(-c2nc(N3CCOCC3)nc3c(Cl)cc(C(=O)OC)nc23)c1]

Intermediate 5 (5 g, 14.1 mmol), 3-methoxymethyl-phenyl boronic acid (4.68 g, 28.2 mmol), CuTC (5.37 g, 28.2 mmol) and Pd(PPh$_3$)$_4$ (1.15 g, 1 mmol) in dioxane (300 mL) were reacted according to General Procedure A. Purification by column chromatography (n-hexane/ethyl acetate, 2/1) afforded the title compound as a yellow solid.

LC/MS (method A): RT=5.32 min (purity: 92%). MS (ES+): 428.8

$^1$H NMR (400 MHz, DMSO-$d_6$): δ 8.38-8.36 (m, 2H), 8.26 (d, J=6.2 Hz, 1H), 7.56-7.53 (m, 2H), 4.53 (s, 2H), 4.06-3.98 (m, 4H), 3.89 (s, 3H), 3.77-3.74 (m, 4H), 3.32 (s, 3H).

HPLC (Method A): RT=5.32 min (purity: 95%).

Intermediate 23

8-Chloro-4-(3-methoxymethyl-phenyl)-2-morpholin-4-yl-pyrido[3,2-d]pyrimidine-6-carboxylic acid

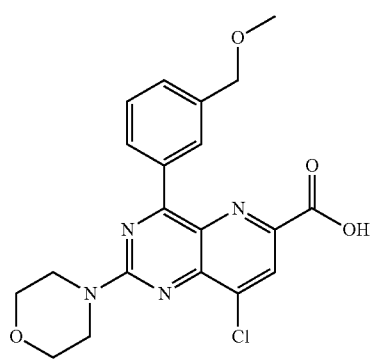 [SMILES: COCc1cccc(-c2nc(N3CCOCC3)nc3c(Cl)cc(C(=O)O)nc23)c1]

To a solution of Intermediate 22 (1.2 g, 2.7 mmol) in a mixture of methanol/THF/water (3/2/1, 30 mL), lithium hydroxide (0.2 g, 8.3 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.95 g, 83%) as a yellow solid.

LC/MS (method A): RT=3.82 min (purity: 94%). MS (ES−): 412.9.

$^1$H NMR (400 MHz, DMSO-$d_6$): δ 13.60 (br s, 1H), 8.33-8.28 (m, 3H), 7.55-7.53 (m, 2H), 4.51 (s, 2H), 4.00-3.99 (m, 4H), 3.75 (t, J=4.7 Hz, 4H), 3.34 (s, 3H).

HPLC (Method A): RT=4.49 min (purity: 91%).

Intermediate 24

8-Chloro-4-(5-fluoro-2-hydroxy-phenyl)-2-morpholin-4-yl-pyrido[3,2-d]pyrimidine-6-carboxylic acid methyl ester

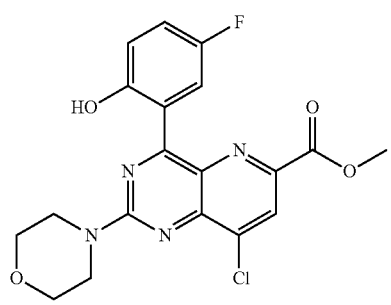 [SMILES: COC(=O)c1cc(Cl)c2nc(N3CCOCC3)nc(-c3cc(F)ccc3O)c2n1]

Intermediate 5 (4 g, 11 mmol), 5-fluoro-2-hydroxy phenyl boronic acid (3.49 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by column chromatography (n-hexane/ethyl acetate, 1/1) afforded the title compound as an orange solid.

LC/MS (method A): RT=5.40 min (purity: 90%). MS (ES+): 419.0

$^1$H NMR (400 MHz, DMSO-$d_6$): δ 10.40 (s, 1H), 8.38 (s, 1H), 7.65-7.62 (dd, J=3.2, 6.4 Hz, 1H), 7.28-7.24 (m, 1H), 6.98-6.94 (dd, J=4.8, 4.2 Hz, 1H), 3.95 (m, 4H), 3.86 (s, 3H), 3.74 (m, 4H).

HPLC (Method A): RT=6.52 min (purity: 93%).

Intermediate 25

8-Chloro-4-(5-fluoro-2-hydroxy-phenyl)-2-morpholin-4-yl-pyrido[3,2-d]pyrimidine-6-carboxylic acid

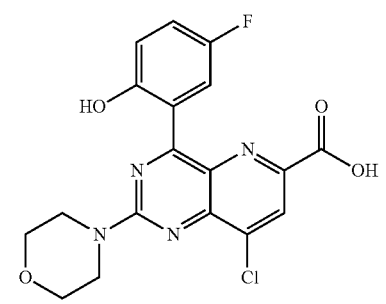 [SMILES: O=C(O)c1cc(Cl)c2nc(N3CCOCC3)nc(-c3cc(F)ccc3O)c2n1]

The title compound was prepared as described for Intermediate 23 starting from Intermediate 24.

LC/MS (method A): RT=1.89 min (purity: 96%). MS (ES+): 404.8.

Intermediate 26

8-Chloro-4-(3-fluoro-2-hydroxy-phenyl)-2-morpholin-4-yl-pyrido[3,2-d]pyrimidine-6-carboxylic acid methyl ester

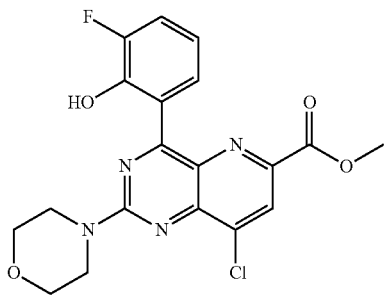 [SMILES: COC(=O)c1cc(Cl)c2nc(N3CCOCC3)nc(-c3cccc(F)c3O)c2n1]

Intermediate 5 (4 g, 11 mmol), 3-fluoro-2-hydroxy phenyl boronic acid (3.49 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by column chromatography (n-hexane/ethyl acetate, 1/1) afforded the title compound as an orange solid.

LC/MS (method A): RT=5.28 min (purity: 98%). MS (ES+): 419.0

$^1$H NMR (400 MHz, DMSO-d$_6$): δ 10.60 (1s, 1H), 8.39 (s, 1H), 7.55-7.53 (d, J=7.9 Hz, 1H), 7.40-7.35 (m, 1H), 6.98-6.93 (m, 1H), 3.96 (m, 4H), 3.86 (s, 3H), 3.74 (m, 4H).

HPLC (Method A): RT=6.32 min (purity: 98%).

Intermediate 27

8-Chloro-4-(3-fluoro-2-hydroxy-phenyl)-2-morpholin-4-yl-pyrido[3,2-d]pyrimidine-6-carboxylic acid

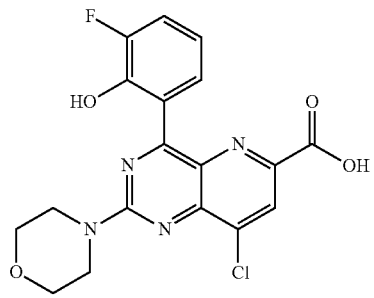 [SMILES: O=C(O)c1cc(Cl)c2nc(N3CCOCC3)nc(-c3cccc(F)c3O)c2n1]

To a solution of Intermediate 26 (1.0 g, 2.4 mmol) in a mixture of methanol/THF/water (3/2/1, 30 mL), lithium hydroxide (0.2 g, 4.8 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.96 g, 99%) as a yellow solid.

LC/MS (method A): RT=4.48 min (purity: 92%). MS (ES+): 405.0

$^1$H NMR (400 MHz, DMSO-d$_6$): δ 13.69 (s, 1H), 11.04, (s, 1H, s), 8.38 (s, 1H, s), 7.64-7.62 (d, J=8.0 Hz, 1H), 7.41-7.36 (m, 1H), 6.98-6.93 (m, 1H), 3.96 (m, 4H), 3.74 (m, 4H).

HPLC (Method A): RT=4.47 min (purity: 93%).

Intermediate 28

8-Chloro-4-(2-hydroxy-phenyl)-2-morpholin-4-yl-pyrido[3,2-d]pyrimidine-6-carboxylic acid methyl ester

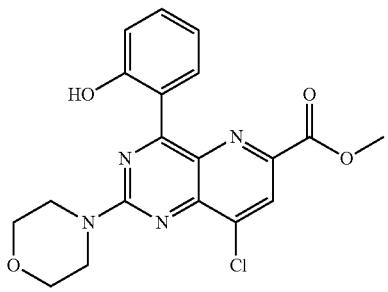 [SMILES: COC(=O)c1cc(Cl)c2nc(N3CCOCC3)nc(-c3ccccc3O)c2n1]

Intermediate 5 (4 g, 11 mmol), 2-hydroxy phenyl boronic acid (3.08 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by trituration in ACN then Et$_2$O afforded the title compound as a yellow solid.

LC/MS (method A): RT=5.24 min (purity: 100%). MS (ES+): 400.8.

$^1$H NMR (400 MHz, DMSO-d$_6$): δ 10.40 (s, 1H), 8.36 (s, 1H), 7.75-7.73 (d, J=7.6 Hz, 1H), 7.41-7.37 (m, 1H), 6.98-6.93 (m, 2H), 3.95 (m, 4H), 3.85 (s, 3H), 3.73 (m, 4H).

HPLC (Method A): RT=5.21 min (purity: 100%).

Intermediate 29

8-Chloro-4-(2-hydroxy-phenyl)-2-morpholin-4-yl-pyrido[3,2-d]pyrimidine-6-carboxylic acid

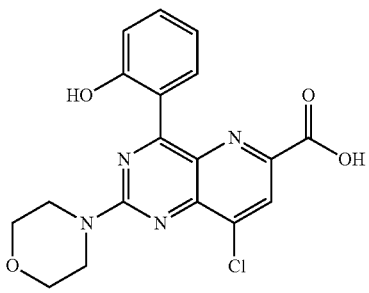 [SMILES: O=C(O)c1cc(Cl)c2nc(N3CCOCC3)nc(-c3ccccc3O)c2n1]

The title compound was prepared as described for Intermediate 23 starting from Intermediate 28.

LC/MS (method A): RT=4.37 min (purity: 96%). MS (ES+): 387.0.

Intermediate 30

8-Chloro-4-(3-fluoro-4-hydroxy-phenyl)-2-morpholin-4-yl-pyrido[3,2-d]pyrimidine-6-carboxylic acid methyl ester

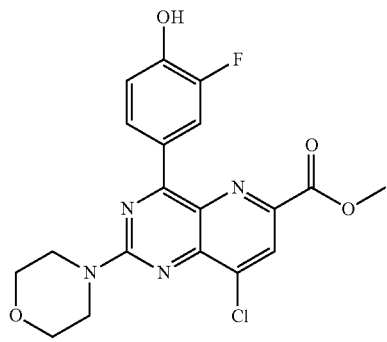 [SMILES: COC(=O)c1cc(Cl)c2nc(N3CCOCC3)nc(-c3ccc(O)c(F)c3)c2n1]

Intermediate 5 (4 g, 11 mmol), 3-fluoro-4-hydroxy phenyl boronic acid (3.49 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by column chromatography (n-hexane/ethyl acetate, 1/1) afforded the title compound as an orange solid.

LC/MS (method A): RT=4.96 min (purity: 94%). MS (ES+): 419.0.

$^1$H NMR (400 MHz, DMSO-d$_6$): δ 10.74 (s, 1H), 8.58-8.56 (dd, J=2.0, 11.5 Hz, 1H), 8.37-8.31 (m, 2H), 7.12-7.08 (t, J=8.9 Hz, 1H) 3.99 (m, 4H), 3.92 (s, 3H), 3.75-3.73 (m, 4H).

HPLC (Method A): RT=4.97 min (purity: 95%).

Intermediate 31

8-Chloro-4-(3-fluoro-4-hydroxy-phenyl)-2-morpholin-4-yl-pyrido[3,2-d]pyrimidine-6-carboxylic acid

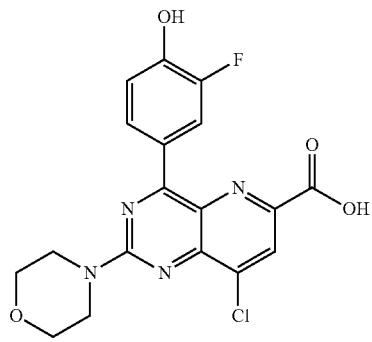 [SMILES: O=C(O)c1cc(Cl)c2nc(N3CCOCC3)nc(-c3ccc(O)c(F)c3)c2n1]

The title compound was prepared as described for Intermediate 23 starting from Intermediate 30.

LC/MS (method A): RT=1.71 min (purity: 99%). MS (ES+): 404.8.

Intermediate 32

8-Chloro-4-(4-fluoro-3-hydroxymethyl-phenyl)-2-morpholin-4-yl-pyrido[3,2-d]pyrimidine-6-carboxylic acid methyl ester

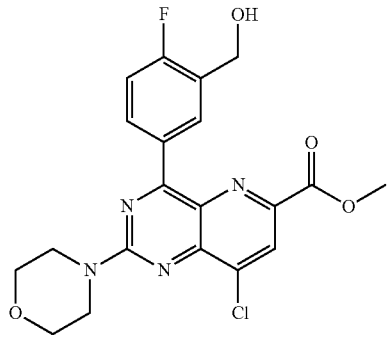 [SMILES: COC(=O)c1cc(Cl)c2nc(N3CCOCC3)nc(-c3ccc(F)c(CO)c3)c2n1]

Intermediate 5 (2 g, 5.6 mmol), 4-fluoro-3-hydroxymethyl phenyl boronic acid (1.9 g, 11 mmol), CuTC (2.13 g, 11 mmol) and Pd(PPh$_3$)$_4$ (0.51 g, 0.4 mmol) in dioxane (100 mL) were reacted according to General Procedure A. Purification by trituration in ACN afforded the title compound as a yellow solid.

LC/MS (method A): RT=4.71 min (purity: 95%). MS (ES+): 433.0.

$^1$H NMR (400 MHz, DMSO-d$_6$): δ 8.60 (dd, J=2.0, 5.4 Hz, 1H), 8.45-8.41 (m, 1H), 8.4 (s, 1H), 7.35 (t, J=9.0 Hz, 1H), 5.39 (t, J=5.8 Hz, 1H), 4.64 (d, J=5.6 Hz, 2H), 4.01 (m, 4H), 3.90 (s, 3H), 3.77-3.74 (m, 4H).

HPLC (Method A): RT=4.71 min (purity: 99%).

Intermediate 33

8-Chloro-4-(4-fluoro-3-hydroxymethyl-phenyl)-2-morpholin-4-yl-pyrido[1,2-d]pyrimidine-6-carboxylic acid

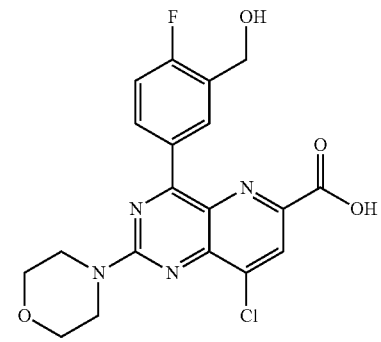 [SMILES: O=C(O)c1cc(Cl)c2nc(N3CCOCC3)nc(-c3ccc(F)c(CO)c3)c2n1]

The title compound was prepared as described for Intermediate 23 starting from Intermediate 32.

LC/MS (method A): RT=3.97 min (purity: 84%). MS (ES+): 419.0.

Intermediate 34

8-Chloro-4-(4-fluoro-2-hydroxy-phenyl)-2-morpholin-4-yl-pyrido[3,2-d]pyrimidine-6-carboxylic acid methyl ester

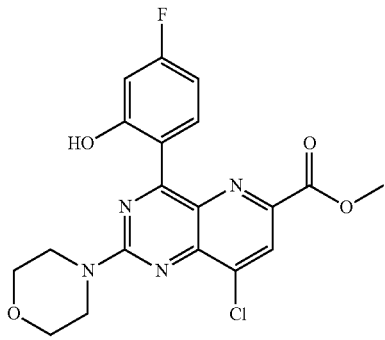 [SMILES: COC(=O)c1cc(Cl)c2nc(N3CCOCC3)nc(-c3ccc(F)cc3O)c2n1]

Intermediate 5 (4 g, 11 mmol), 4-fluoro-2-hydroxy phenyl boronic acid (3.49 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by trituration in cold methanol afforded the title compound as an orange solid.

LC/MS (method A): RT=5.52 min (purity: 98%). MS (ES+): 419.0.

$^1$H NMR (400 MHz, DMSO-d$_6$): δ 11.15 (s, 1H), 8.38 (s, 1H), 7.94-7.90 (m, 1H), 6.84-6.76 (m, 2H), 3.95 (m, 4H), 3.87 (s, 3H), 3.74 (m, 4H).

HPLC (Method A): RT=6.50 min (purity: 98%).

Intermediate 35

8-Chloro-4-(4-fluoro-2-hydroxy-phenyl)-2-morpholin-4-yl-pyrido[3,2-d]pyrimidine-6-carboxylic acid

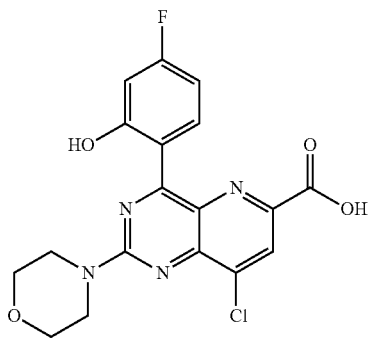 [SMILES: O=C(O)c1cc(Cl)c2nc(N3CCOCC3)nc(-c3ccc(F)cc3O)c2n1]

The title compound was prepared as described for Intermediate 23 starting from Intermediate 34.

LC/MS (method A): RT=4.60 min (purity: 99%). MS (ES+): 405.0.

Intermediate 36

4-(3-Hydroxyphenyl)-2-morpholin-4-yl-8-piperazin-1-ylpyrido[3,2-d]pyrimidine-6-carboxylic acid

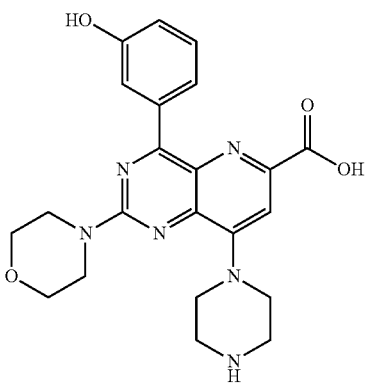 [SMILES: O=C(O)c1cc(N2CCNCC2)c2nc(N3CCOCC3)nc(-c3cccc(O)c3)c2n1]

A mixture of Example 9 (100 mg; 0.26 mmol), 1-Boc-piperazine (241 mg; 1.29 mmol) and N-ethyl-N-isopropyl-propan-2-amine (0.09 mL; 0.52 mmol) in THF (3 mL) and water (2 mL) was stirred at 130° C. for 16 hours then concentrated in vacuo. The residue was taken up in water and acidified to pH 2 with 1M HCl 1 N. The solution was washed with EA and acetonitrile was added until precipitation occurred. The solid was collected by filtration and washed with Et$_2$O to afford the title compound as a red solid.

HPLC (Method B): RT=1.90 min (purity: 88%).

Intermediate 37

8-Chloro-4-(4-hydroxy-2-methyl-phenyl)-2-morpholin-4-yl-pyrido[3,2-d]pyrimidine-6-carboxylic acid methyl ester

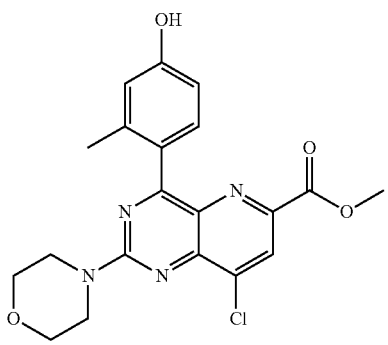 [SMILES: COC(=O)c1cc(Cl)c2nc(N3CCOCC3)nc(-c3ccc(O)cc3C)c2n1]

Intermediate 5 (4 g, 11 mmol), 4-hydroxy-2-methyl phenyl boronic acid (3.4 g, 22 mmol), CuTC (4.26 g, 22 mmol) and Pd(PPh$_3$)$_4$ (1.02 g, 0.8 mmol) in dioxane (200 mL) were reacted according to General Procedure A. Purification by trituration in ACN then Et$_2$O afforded the title compound as a yellow solid.

LC/MS (method A): RT=4.81 min (purity: 97%). MS (ES+): 414.8.

¹H NMR (400 MHz, DMSO-d₆): δ 9.80 (s, 1H), 8.32 (d, J=4.9 Hz, 1H), 7.36 (d, J=8.4 Hz, 1H), 6.74 (d, J=2.0 Hz, 1H), 6.70 (dd, J=2.3, 6.0 Hz, 1H), 3.95 (m, 4H), 3.83 (s, 3H), 3.72 (m, 4H), 2.19 (s, 3H).
HPLC (Method A): RT=5.82 min (purity: 94%).

Intermediate 38

8-Chloro-4-(4-hydroxy-2-methyl-phenyl)-2-morpholin-4-yl-pyrido[3,2-d]pyrimidine-6-carboxylic acid

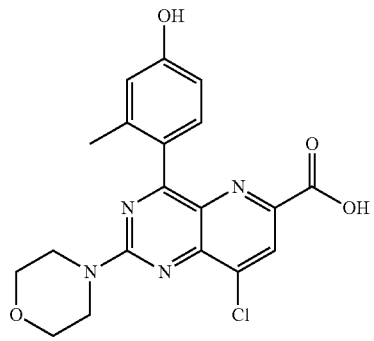 [SMILES: Cc1cc(O)ccc1-c1nc(N2CCOCC2)nc2c(Cl)cc(C(=O)O)nc12]

To a solution of Intermediate 37 (1.0 g, 2.4 mmol) in a mixture of methanol/THF/water (3/2/1, 30 mL), lithium hydroxide (0.2 g, 4.8 mmol) was added. The reaction mixture was stirred at 90° C. for 1 hour then concentrated in vacuo. The residue was dissolved in water (5 mL) and neutralized with 20% aq. citric acid. The aqueous layer was then extracted with ethyl acetate (3×50 mL), the combined organic phase washed with water (50 mL) and brine (50 mL) and dried over sodium sulfate to afford, after evaporation, the title compound (0.95 g, 98%) as a yellow solid.
LC/MS (method A): RT=4.11 min (purity: 95%). MS (ES+): 400.8.
¹H NMR (400 MHz, DMSO-d₆): δ 13.42 (s, 1H), 9.78, (s, 1H), 8.30 (s, 1H), 7.37 (d, J=8.4 Hz, 1H), 6.74-6.68 (m, 2H), 4.01-3.99 (m, 4H), 3.74-3.70 (m, 4H), 2.19 (s, 3H).
HPLC (Method A): RT=4.13 min (purity: 97%).

Intermediate 39

Methyl 8-chloro-2-morpholin-4-yl-4-phenylpyrido[3,2-d]pyrimidine-6-carboxylate

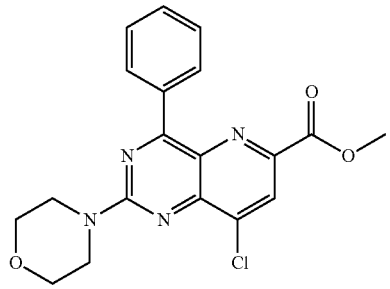 [SMILES: COC(=O)c1cc(Cl)c2nc(N3CCOCC3)nc(-c3ccccc3)c2n1]

Intermediate 5 (250 mg, 0.7 mmol), phenyl boronic acid (129 mg, 1.1 mmol), CuTC (269 mg, 1.4 mmol) and Pd(PPh₃)₄ (41 mg, 0.04 mmol) were reacted in dioxane (9 mL) according to General Procedure A. Purification by crystallization from MeOH afforded the title compound (200 mg, 74%) as a yellow solid.
¹H NMR (300 MHz, DMSO-d₆): δ 8.39-8.37 (m, 2H), 8.37-8.35 (m, 1H), 7.64-7.54 (m, 3H), 4.06-3.99 (m, 4H), 3.91 (s, 3H), 3.79-3.73 (m, 4H).
HPLC (Method B): RT=4.99 min (purity: 67%).

Intermediate 40

Methyl 8-chloro-4-(3,5-difluorophenyl)-2-morpholin-4-ylpyrido[3,2-d]pyrimidine-6-carboxylate

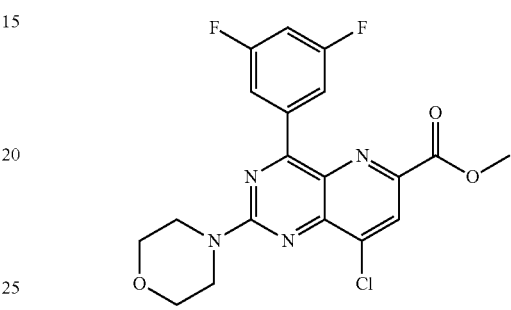

Intermediate 5 (250 mg, 0.7 mmol), 3,5-difluorophenyl boronic acid (167 mg, 1.1 mmol), CuTC (269 mg, 1.4 mmol) and Pd(PPh₃)₄ (41 mg, 0.04 mmol) were reacted in dioxane (9 mL) according to General Procedure A. Purification by crystallization from MeOH afforded the title compound as a yellow solid.
¹H NMR (300 MHz, DMSO-d₆): δ 8.40 (s, 1H), 8.26-8.19 (m, 2H), 7.55 (tt, J=9.1, 2.4 Hz, 1H), 4.08-3.98 (m, 4H), 3.92 (s, 3H), 3.79-3.73 (m, 4H).
HPLC (Method B): RT=5.06 min (purity: 100%).

Intermediate 41

8-Chloro-4-(3,5-difluorophenyl)-2-morpholin-4-ylpyrido[3,2-d]pyrimidine-6-carboxylic acid

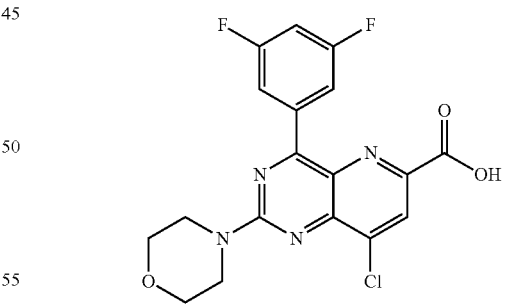

A mixture of Intermediate 40 (200 mg; 0.48 mmol) and 1M NaOH (4.7 mL, 4.7 mmol) in THF (5 mL) was stirred at room temperature for 3 hours then acidified to pH 2 with 1M HCl. Extraction with DCM, drying over magnesium sulfate and concentration in vacuo afforded the title compound (188 mg, 97%) as a yellow solid.
¹H NMR (300 MHz, DMSO-d₆): δ 13.60-13.32 (m, 1H), 8.39 (s, 1H), 8.30-8.24 (m, 2H), 7.56 (tt, J=9.2, 2.4 Hz, 1H), 4.06-3.99 (m, 4H), 3.79-3.73 (m, 4H).
HPLC (Method B): RT=4.30 min (purity: 98%).

Intermediate 42

Methyl 8-chloro-4-(3-cyanophenyl)-2-morpholin-4-ylpyrido[3,2-d]pyrimidine-6-carboxylate

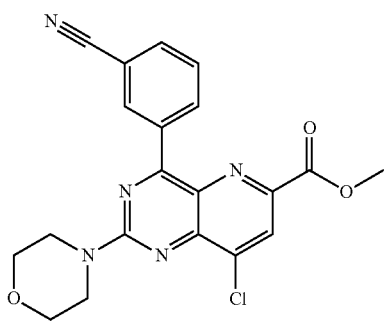 [SMILES: COC(=O)c1cc(Cl)c2nc(N3CCOCC3)nc(-c3cccc(C#N)c3)c2n1]

Intermediate 5 (200 mg, 0.56 mmol), 3-cyanophenyl boronic acid (124 mg, 0.85 mmol), CuTC (215 mg, 1.13 mmol) and Pd(PPh$_3$)$_4$ (33 mg, 0.03 mmol) were reacted in dioxane (7 mL) according to General Procedure A. Purification by recrystallization from MeOH afforded the title compound (194 mg, 84%) as a yellow solid.

$^1$H NMR (300 MHz, DMSO-d$_6$): δ 8.90 (s, 1H), 8.67 (d, J=7.9 Hz, 1H), 8.40 (s, 1H), 8.10 (d, J=7.4 Hz, 1H), 7.82-7.77 (m, 1H), 4.08-3.99 (m, 4H), 3.92 (s, 3H), 3.80-3.73 (m, 4H).

HPLC (Method B): RT=4.83 min (purity: 83%).

Intermediate 43

8-Chloro-4-(3-cyanophenyl)-2-morpholin-4-ylpyrido[3,2-d]pyrimidine-6-carboxylic acid

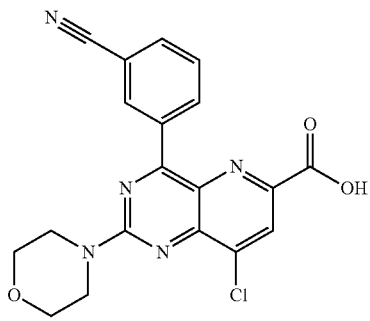 [SMILES: N#Cc1cccc(-c2nc(N3CCOCC3)nc3c(Cl)cc(C(=O)O)nc23)c1]

A mixture of Intermediate 42 (194 mg; 0.47 mmol) and 1M NaOH (5 mL, 5 mmol) in THF (10 mL) was stirred at room temperature for 4 hours then acidified to pH 2 with 1M HCl. Extraction with DCM, drying over magnesium sulfate and concentration in vacuo afforded the title compound (174 mg, 93%) as a yellow solid.

$^1$H NMR (300 MHz, DMSO-d$_6$): δ 13.60 (s, 1H), 8.88 (br s, 1H), 8.71-8.67 (m, 1H), 8.38 (s, 1H), 8.11-8.07 (m, 1H), 7.82-7.77 (m, 1H), 4.07-3.98 (m, 4H), 3.78-3.75 (m, 4H).

HPLC (Method B): RT=3.93 min (purity: 93%).

Example 1

8-Chloro-4-(3-methoxyphenyl)-2-morpholin-4-ylpyrido[3,2-d]pyrimidine-6-carboxylic acid

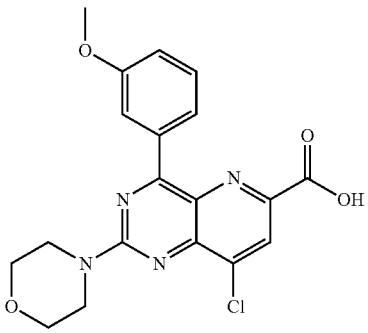 [SMILES: COc1cccc(-c2nc(N3CCOCC3)nc3c(Cl)cc(C(=O)O)nc23)c1]

Lithium hydroxide (46 mg, 1.93 mmol) was added to a solution of Intermediate 6 (200 mg, 0.48 mmol) in THF (10 mL), followed by water (10 mL), and the resulting mixture was stirred at room temperature for 3 hours. The THF was evaporated in vacuo and the residue diluted with water. The pH was adjusted to 2 with 5M HCl and the product extracted with DCM. The organic layer was dried over magnesium sulfate and concentrated in vacuo. The residue was suspended in ACN, stirred at 50° C. for 10 minutes, allowed to return to room temperature and filtered to afford the title compound (182 mg, 94%) as a yellow solid.

LC/MS (method B): RT=0.90 min (purity: 100%). MS (ES+): 401.1

$^1$H NMR (300 MHz, DMSO-d$_6$): δ 13.55 (s, 1H), 8.36 (s, 1H), 8.23-8.20 (m, 1H), 7.98 (d, J=7.8 Hz, 1H), 7.48 (t, J=8.0 Hz, 1H), 7.19 (dd, J=7.8, 2.3 Hz, 1H), 4.02 (br s, 4H), 3.86 (s, 3H), 3.76 (br t, J=4.6 Hz, 4H).

HPLC (Method B): RT=4.16 min (purity: 98%).

Example 2

4-(3-Methoxyphenyl)-2-morpholin-4-ylpyrido[3,2-d]pyrimidine-6-carboxylic acid

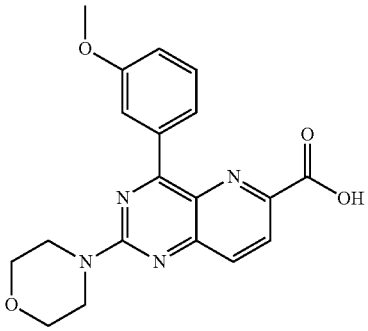 [SMILES: COc1cccc(-c2nc(N3CCOCC3)nc3ccc(C(=O)O)nc23)c1]

A mixture of Intermediate 7 (65 mg, 0.17 mmol) and NaOH (34 mg, 0.85 mmol) in water (5 mL) and THF (5 mL) was stirred at room temperature for 15 hours. The reaction mixture was diluted with water and washed with DCM. The pH was adjusted to 2 and the product extracted with DCM (2×). The combined organic layer was dried over magnesium sulfate and concentrated in vacuo. The residue was suspended in ACN, stirred at 60° C. for 10 minutes and allowed to return to room temperature. The precipitate was collected by filtration and dried to afford the title compound (50 mg, 80%) as a yellow solid.

LC/MS (method B): RT=0.78 min (purity: 99%). MS (ES+): 367.2

$^1$H NMR (300 MHz, DMSO-d$_6$): δ 13.34 (s, 1H), 8.30-8.22 (m, 2H), 8.05-7.99 (m, 2H), 7.48 (t, J=8.0 Hz, 1H), 7.20-7.14 (m, 1H), 4.01-3.91 (m, 4H), 3.87 (s, 3H), 3.74 (br t, J=4.6 Hz, 4H).

HPLC (Method B): RT=3.28 min (purity: 99%).

Example 3

4-(4-hydroxy-phenyl)-8-[(2-methoxy-ethyl)-methyl-amino]-2-morpholin-4-yl-pyrido[3,2-d]pyrimidine-6-carboxylic acid

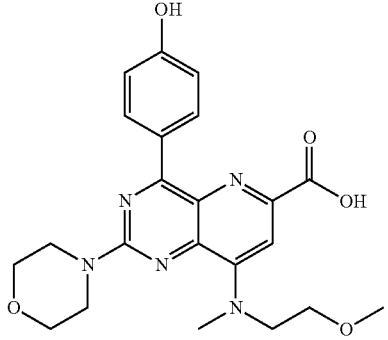 [SMILES: COCCN(C)c1cc(C(=O)O)nc2c(-c3ccc(O)cc3)nc(N3CCOCC3)nc12]

A mixture of Intermediate 9 (0.1 g, 0.25 mmol) and N-(2-methoxy ethyl)methyl amine (34 mg, 0.38 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.50 min (purity: 97%). MS (ES+): 440.0.

Example 4

8-Dimethylamino-4-(4-hydroxy-phenyl)-2-morpholin-4-yl-pyrido[3,2-d]pyrimidine-6-carboxylic acid

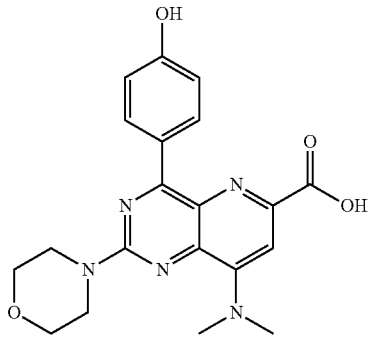 [SMILES: CN(C)c1cc(C(=O)O)nc2c(-c3ccc(O)cc3)nc(N3CCOCC3)nc12]

A mixture of Intermediate 9 (0.12 g, 0.31 mmol) and dimethylamine hydrochloride (39 mg, 0.47 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.32 min (purity: 99%). MS (ES+): 395.9

$^1$H NMR (400 MHz, DMSO-d$_6$): δ 10.03 (s, 1H), 8.45 (d, J=8.8 Hz, 2H), 7.33 (s, 1H), 6.87 (d, J=8.8 Hz, 1H), 4.00-3.84 (m, 4H), 3.74-3.73 (m, 4H), 3.27 (s, 6H).

HPLC (Method A): RT=2.88 min (purity: 91%).

Example 5

4-(4-Hydroxy-phenyl)-8-(2-methoxy-ethylamino)-2-morpholin-4-yl-pyrido[3,2-d]pyrimidine-6-carboxylic acid

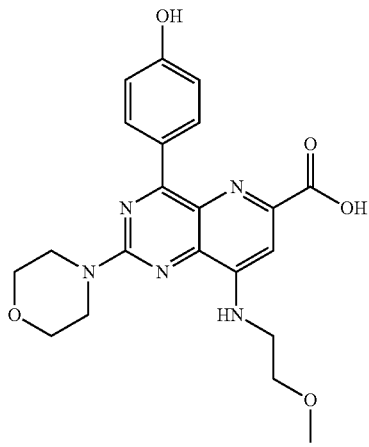 [SMILES: COCCNc1cc(C(=O)O)nc2c(-c3ccc(O)cc3)nc(N3CCOCC3)nc12]

A mixture of Intermediate 9 (0.12 g, 0.31 mmol) and 2-methoxyethylamine (35 mg, 0.46 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.11 min (purity: 99%). MS (ES+): 426.0

$^1$H NMR (400 MHz, DMSO-d$_6$): δ 12.83 (s, 1H), 10.07 (s, 1H), 8.59 (d, J=8.7 Hz, 2H), 7.20 (s, 1H), 7.15 (br s, 1H), 6.88 (d, J=8.8 Hz, 2H), 3.94-3.93 (m, 4H), 3.74-3.73 (m, 4H), 3.57-3.56 (m, 2H), 3.52-3.51 (m, 2H), 3.29 (s, 3H).

Example 6

4-(4-Hydroxy-phenyl)-8-(2-methoxy-ethoxy)-2-morpholin-4-yl-pyrido[3,2-d]pyrimidine-6-carboxylic acid

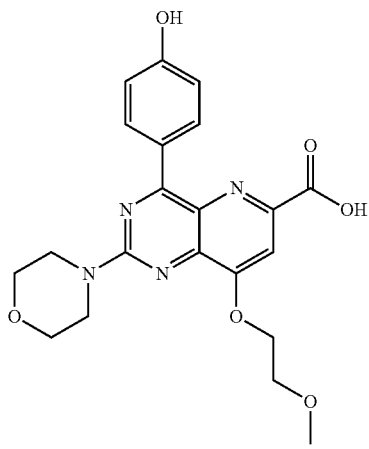 [SMILES: COCCOc1cc(C(=O)O)nc2c(-c3ccc(O)cc3)nc(N3CCOCC3)nc12]

Small pieces of sodium (21 mg, 0.9 mmol) were added 2-methoxy ethanol (1 mL), at 0° C., and the reaction mixture was stirred at room temperature for 30 min. The clear solution obtained was then added to a solution of Intermediate 8 (0.12 g, 0.31 mmol) in dimenthylformamide (3 mL) and the reaction mixture was stirred at 120° C. for 16 hours. After concentration in vacuo, the residue was taken up in water (5 mL), neutralized with 20% aqueous citric acid and extracted with ethyl acetate (2×50 mL). The organic layer was washed with brine (2×50 mL), dried over sodium sulfate and concentrated in vacuo. Purification by column chromatography (CHCl$_3$/MeOH, 9/1) afforded the title compound as a yellow solid.

LC/MS (method A): RT=3.00 min (purity: 96%). MS (ES+): 426.7

$^1$H NMR (400 MHz, DMSO-d$_6$): δ 10.20 (br s, 1H), 8.58 (d, J=8.7 Hz, 2H), 7.67 (s, 1H), 6.90 (d, J=8.8 Hz, 2H), 4.37 (t, J=4.4 Hz, 2H), 4.01 (s, 1H), 3.94-3.90 (m, 4H), 3.79 (t, J=4.4 Hz, 2H), 3.74-3.70 (m, 4H), 3.36 (s, 3H).

HPLC (Method A): RT=3.99 min (purity: 94%).

Example 7

8-(2-Hydroxy-ethylamino)-4-(4-hydroxy-phenyl)-2-morpholin-4-yl-pyrido[3,2-d]pyrimidine-6-carboxylic acid

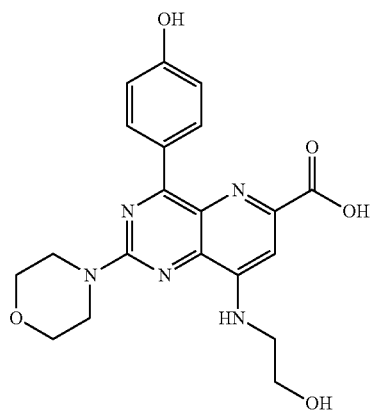 [SMILES: O=C(O)c1cc(NCCO)c2nc(N3CCOCC3)nc(-c3ccc(O)cc3)c2n1]

A mixture of Intermediate 9 (0.12 g, 0.31 mmol) and 2-amino ethanol (28 mg, 0.46 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.82 min (purity: 95%). MS (ES+): 412.0

$^1$H NMR (400 MHz, DMSO-d$_6$): δ 10.06 (br s, 1H), 8.60 (d, J=8.8 Hz, 2H), 7.20 (s, 1H), 7.10 (br s, 1H), 6.90 (d, J=8.8 Hz, 2H), 4.92 (br s, 1H), 3.95-3.93 (m, 4H), 3.75-3.74 (m, 4H), 3.66-3.62 (m, 2H), 3.41-3.39 (m, 2H).

HPLC (Method A): RT=4.05 min (purity: 92%).

Example 8

4-(4-Hydroxy-phenyl)-2-morpholin-4-yl-pyrido[3,2-d]pyrimidine-6-carboxylic acid

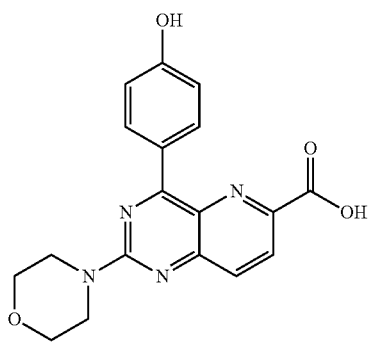 [SMILES: O=C(O)c1ccc2nc(N3CCOCC3)nc(-c3ccc(O)cc3)c2n1]

To a solution of Intermediate 10 (0.1 g, 0.27 mmol) in a mixture of methanol/THF/water (3/2/1, 12 mL), lithium hydroxide (0.02 g, 0.54 mmol) was added. The reaction mixture was stirred at 90° C. for 1 hour then concentrated under vacuum. The residue was dissolved in water (5 mL) and neutralized with 20% aqueous solution of citric acid. The aqueous layer was then extracted with ethyl acetate (2×25 mL), the combined organic phase washed with water (25 mL) and brine (25 mL) and dried over sodium sulfate to afford, after evaporation, the title compound as a yellow solid.

LC/MS (method A): RT=3.43 min (purity: 98%). MS (ES+): 353.2

$^1$H NMR (400 MHz, DMSO-d$_6$): δ 13.25 (br s 1H), 10.16 (s, 1H), 8.57 (d, J=8.8 Hz, 2H), 8.21 (d, J=8.8 Hz, 1H), 7.96 (d, J=8.8 Hz, 1H), 6.91 (d, J=8.8 Hz, 2H), 3.97-3.93 (m, 4H), 3.74-3.72 (m, 4H).

HPLC (Method A): RT=3.18 min (purity: 98%).

Example 9

8-Chloro-4-(3-hydroxyphenyl)-2-morpholin-4-ylpyrido[3,2-d]pyrimidine-6-carboxylic acid

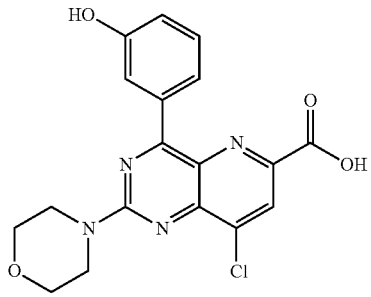 [SMILES: O=C(O)c1cc(Cl)c2nc(N3CCOCC3)nc(-c3cccc(O)c3)c2n1]

A mixture of 3-hydroxybenzeneboronic acid (238 mg, 1.73 mmol), Intermediate 4 (500 mg, 1.64 mmol), CuTC (627 mg, 3.29 mmol) and Pd(PPh$_3$)$_4$ (95 mg, 0.08 mmol) in dioxane (20 mL) was stirred at 50° C. for 6 hours. The dark solution was diluted with 5% aq. citric acid and extracted with DCM (2×). The combined organic phase was washed with brine, dried over sodium sulfate and filtered through a short pad of Celite®. After concentration in vacuo, the residue was washed with Et$_2$O to afford the crude dichloropyridopyrimidine derivative as a brown solid. The solid was suspended in ACN (15 mL) and morpholine (358 mg, 4.11 mmol) was added. The reaction mixture was stirred at room temperature for 16 hours then concentrated in vacuo. The residue was partitioned between DCM and 5% aq. citric acid. The aqueous phase was extracted with DCM and the combined organic layer washed with brine, dried over magnesium sulfate and concentrated in vacuo. The residue was filtered through a short plug of silica using increasing amount of MeOH in DCM as eluent to afford the crude ester as a yellow solid. The solid was taken up in dioxane (10 mL), 5M aq. NaOH (5 mL, 25 mmol) was added and the resulting mixture was stirred at room temperature for 14 hours. The solvent was evaporated in vacuo, the pH made acidic with 5N HCl and the compound extracted with DCM (3×). The combined organic layer was dried over magnesium sulfate and concentrated in vacuo. Purification by column chromatography (DCM/MeOH from 99/1 to 90/10) followed by trituration in ACN and filtration afforded the title compound as a yellow solid.

LC/MS (method B): RT=0.84 min (purity: 100%). MS (ES+): 387.1

$^1$H NMR (300 MHz, DMSO-d$_6$): δ 9.71 (br s, 1H), 8.33 (s, 1H), 7.89 (d, J=7.8 Hz, 1H), 7.75 (t, J=1.8 Hz, 1H), 7.33 (t, J=7.9 Hz, 1H), 6.99 (dd, J=8.0, 2.3 Hz, 1H), 4.04-3.92 (m, 4H), 3.80-3.68 (m, 4H)

HPLC (Method B): RT=3.56 min (purity: 98%).

Example 10

4-(3-Hydroxy-phenyl)-8-[(2-methoxy-ethyl)-methyl-amino]-2-morpholin-4-yl-pyrido[3,2-d]pyrimidine-6-carboxylic acid

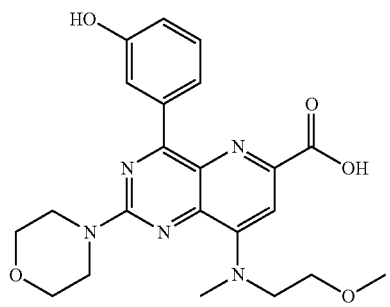 [SMILES: COCCN(C)c1cc(C(=O)O)nc2c(-c3cccc(O)c3)nc(N3CCOCC3)nc12]

A mixture of Example 9 (0.1 g, 0.25 mmol) and N-(2-methoxyethyl)methyl amine (34 mg, 0.38 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.96 min (purity: 98%). MS (ES+): 440.0

Example 11

4-(3-Hydroxy-phenyl)-8-(2-methoxy-ethoxy)-2-morpholin-4-yl-pyrido[3,2-d]pyrimidine-6-carboxylic acid

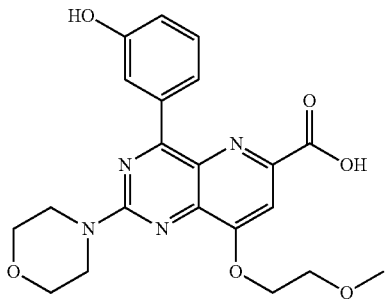 [SMILES: COCCOc1cc(C(=O)O)nc2c(-c3cccc(O)c3)nc(N3CCOCC3)nc12]

Small pieces of sodium (21 mg, 0.9 mmol) were added 2-methoxy ethanol (1 mL), at 0° C., and the reaction mixture was stirred at room temperature for 30 min. The clear solution obtained was then added to a solution of Intermediate 11 (0.12 g, 0.31 mmol) in DMF (3 mL) and the reaction mixture was stirred at 120° C. for 16 hours. After concentration in vacuo, the residue was taken up in water (5 mL), neutralized with 20% aq. citric acid and extracted with ethyl acetate (2×50 mL). The organic layer was washed with brine (2×50 mL), dried over sodium sulfate and concentrated in vacuo. Purification by column chromatography (CHCl$_3$/MeOH, 9/1) afforded the title compound as a yellow solid.

LC/MS (method A): RT=3.27 min (purity: 99%). MS (ES+): 427.0.

Example 12

8-(2-Hydroxy-ethylamino)-4-(3-hydroxy-phenyl)-2-morpholin-4-yl-pyrido[3,2-d]pyrimidine-6-carboxylic acid

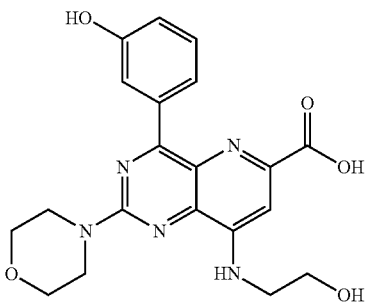 [SMILES: O=C(O)c1cc(NCCO)c2nc(N3CCOCC3)nc(-c3cccc(O)c3)c2n1]

A mixture of Example 9 (0.1 g, 0.25 mmol) and 2-amino ethanol (24 mg, 0.38 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.46 min (purity: 99%). MS (ES+): 412.0

Example 13

4-(3-hydroxyphenyl)-8-(2-methoxyphenyl)-2-morpholin-4-ylpyrido[3,2-d]pyrimidine-6-carboxylic acid

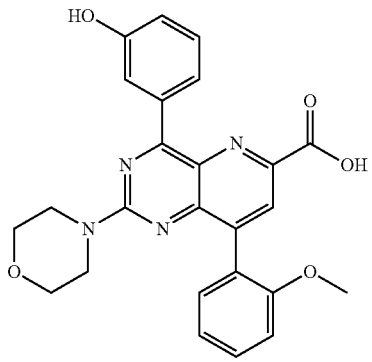 [SMILES: COc1ccccc1-c1cc(C(=O)O)nc2c(-c3cccc(O)c3)nc(N3CCOCC3)nc12]

A suspension of Intermediate 11 (170 mg, 0.42 mmol) and 2-methoxyphenyl boronic acid (97 mg, 0.64 mmol), Pd(PPh$_3$)$_4$ (25 mg, 0.02 mmol) and cesium carbonate (415 mg, 1.27 mmol) in dioxane (3 mL) was stirred at 90° C. for 4 hours. The reaction mixture was then partitioned between DCM and 5% aq. citric acid. The aqueous layer was extracted with DCM and the combined organic phase dried over magnesium sulfate, filtered through a short plug of Celite® and concentrated in vacuo. The residue was taken up in THF (2 mL) and 1M NaOH (2 mL) was added. The reaction mixture was stirred at room temperature for 14 hours then concentrated in vacuo. The residue was dissolved in water, the pH was made acidic with 1M HCl and the compound extracted with DCM (2×). The combined organic phase was dried over magnesium sulfate and concentrated in vacuo. Purification by column chromatography (increasing amount of MeOH in DCM) afforded the title compound as a yellow solid.

LC/MS (method B): RT=1.18 min. (purity: 85%). MS (ES+): 459.3

$^1$H NMR (300 MHz, DMSO-d$_6$): δ 13.30 (s, 1H), 9.64 (s, 1H), 8.14 (s, 1H), 7.88 (d, J=7.9 Hz, 1H), 7.77-7.74 (m, 1H), 7.50-7.39 (m, 2H), 7.35 (t, J=7.9 Hz, 1H), 7.18 (d, J=8.4 Hz, 1H), 7.07 (dt, J=0.7, 7.5 Hz, 1H), 7.00 (ddd, J=0.7, 2.5, 8.0 Hz, 1H), 3.90-3.75 (m, 4H), 3.73 (s, 3H), 3.72-3.60 (m, 4H).

HPLC (Method B): RT=4.06 min (purity: 100%).

Example 14

4-(3-Fluoro-5-hydroxy-phenyl)-8-[(2-methoxy-ethyl)-methyl-amino]-2-morpholin-4-yl-pyrido[3,2-d]pyrimidine-6-carboxylic acid

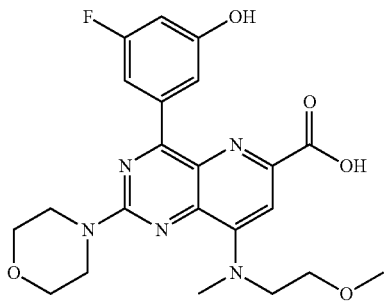 [SMILES: COCCN(C)c1cc(C(=O)O)nc2c(-c3cc(O)cc(F)c3)nc(N3CCOCC3)nc12]

A mixture of Intermediate 13 (0.12 g, 0.29 mmol) and N-(2-methoxyethyl)methyl amine (39 mg, 0.44 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.24 min (purity: 100%). MS (ES+): 457.9

$^1$H NMR (400 MHz, DMSO-d$_6$): δ 13.02 (br s, 1H), 10.07 (s, 1H), 7.80-77 (m, 1H), 7.61 (s, 1H), 7.33 (s, 1H), 6.79-6.73 (m, 1H), 4.22 (t, J=5.9 Hz, 2H), 3.88-3.80 (m, 4H), 3.75-3.74 (m, 4H).

Example 15

4-(3-Fluoro-5-hydroxy-phenyl)-8-(2-methoxy-ethoxy)-2-morpholin-4-yl-pyrido[3,2-d]pyrimidine-6-carboxylic acid

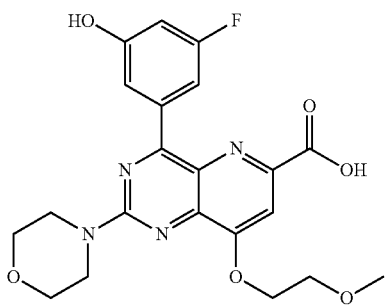 [SMILES: COCCOc1cc(C(=O)O)nc2c(-c3cc(O)cc(F)c3)nc(N3CCOCC3)nc12]

Small pieces of sodium (20 mg, 0.85 mmol) were added to 2-methoxy ethanol (1 mL), at 0° C., and the reaction mixture was stirred at room temperature for 30 min. The clear solution obtained was then added to a solution of Intermediate 12 (0.12 g, 0.28 mmol) in DMF (3 mL) and the reaction mixture was stirred at 120° C. for 16 hours. After concentration in vacuo, the residue was taken up in water (5 mL), neutralized with 20% aq. citric acid and extracted with ethyl acetate (2×50 mL). The organic layer was washed with brine (2×50 mL), dried over sodium sulfate and concentrated in vacuo. Purification by column chromatography (CHCl$_3$/MeOH, 9/1) afforded the title compound as a yellow solid.

LC/MS (method A): RT=3.63 min (purity: 96%). MS (ES+): 444.9.

Example 16

4-(3-Fluoro-5-hydroxy-phenyl)-8-(2-hydroxy-ethylamino)-2-morpholin-4-yl-pyrido[3,2-d]pyrimidine-6-carboxylic acid

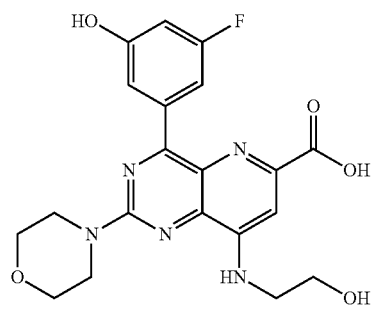

A mixture of Intermediate 13 (0.1 g, 0.24 mmol) and 2-aminoethanol (22 mg, 0.37 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.77 min (purity: 98%). MS (ES+): 429.9.

Example 17

8-Dimethylamino-4-(1H-indol-4-yl)-2-morpholin-4-yl-pyrido[3,2-d]pyrimidine-6-carboxylic acid

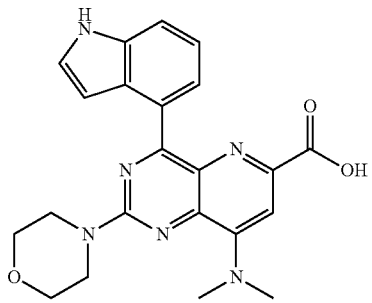 [SMILES: CN(C)c1cc(C(=O)O)nc2c(-c3cccc4[nH]ccc34)nc(N3CCOCC3)nc12]

A mixture of Intermediate 15 (0.1 g, 0.24 mmol), dimethylamine hydrochloride (29 mg, 0.24 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.10 min (purity: 99%). MS (ES+): 419.0.

Example 18

4-(1H-Indol-4-yl)-8-methylamino-2-morpholin-4-yl-pyrido[3,2-d]pyrimidine-6-carboxylic acid

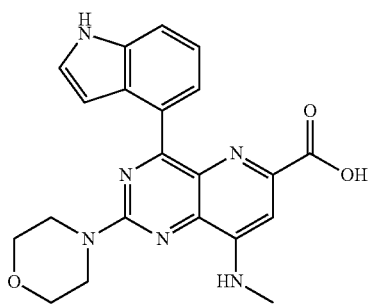 [SMILES: CNc1cc(C(=O)O)nc2c(-c3cccc4[nH]ccc34)nc(N3CCOCC3)nc12]

A mixture of Intermediate 15 (0.1 g, 0.24 mmol) and methylamine hydrochloride (24 mg, 0.36 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.93 min (purity: 97%). MS (ES+): 405.0.

Example 19

4-(1H-Indol-4-yl)-8-(2-methoxy-ethylamino)-2-morpholin-4-yl-pyrido[3,2-d]pyrimidine-6-carboxylic acid

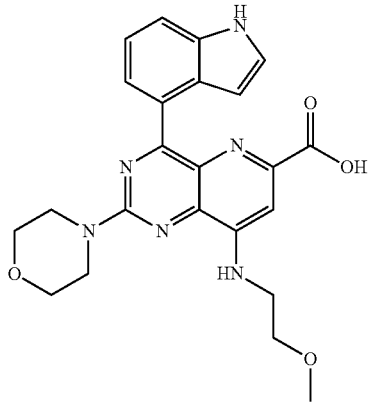 [SMILES: COCCNc1cc(C(=O)O)nc2c(-c3cccc4[nH]ccc34)nc(N3CCOCC3)nc12]

A mixture of Intermediate 15 (0.12 g, 0.29 mmol) and 2-methoxyethylamine (33 mg, 0.44 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.10 min (purity: 98%). MS (ES+): 449.1

$^1$H NMR (400 MHz, DMSO-d$_6$): δ 12.83 (s, 1H), 10.07 (s, 1H), 8.59 (d, J=8.7 Hz, 2H), 7.20 (s, 1H), 7.15 (br s, 1H), 6.88 (d, J=8.8 Hz, 2H), 3.94-3.93 (m, 4H), 3.74-3.73 (m, 4H), 3.57-3.56 (m, 2H), 3.52-3.51 (m, 2H), 3.29 (s, 3H).

Example 20

8-[(2-Hydroxy-ethyl)-methyl-amino]-4-(1H-indol-4-yl)-2-morpholin-4-yl-pyrido[3,2-d]pyrimidine-6-carboxylic acid

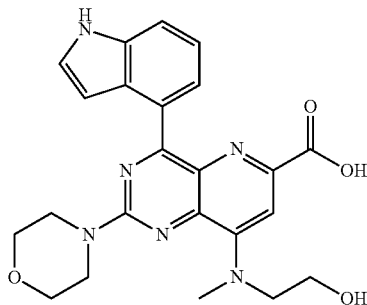 [SMILES: CN(CCO)c1cc(C(=O)O)nc2c(-c3cccc4[nH]ccc34)nc(N3CCOCC3)nc12]

A mixture of Intermediate 15 (0.1 g, 0.24 mmol) and 2-(methyl amino) ethanol (27 mg, 0.36 mmol) in DIEA (1 mL) and water (0.5 mL) was stirred at 170° C. for 2 hours. The two phases were separated and the aqueous layer concen-

Example 21

4-(1H-Indol-5-yl)-8-[(2-methoxy-ethyl)-methyl-amino]-2-morpholin-4-yl-pyrido[3,2-d]pyrimidine-6-carboxylic acid

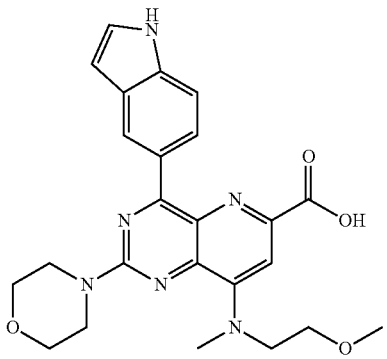 [SMILES: COCCN(C)c1cc(C(=O)O)nc2c(-c3ccc4[nH]ccc4c3)nc(N3CCOCC3)nc12]

A mixture of Intermediate 17 (0.1 g, 0.24 mmol) and N-(2-methoxyethyl)methyl amine (32 mg, 0.36 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.34 min (purity: 99%). MS (ES+): 463.1.

Example 22

4-(4-Hydroxymethyl-phenyl)-8-[(2-methoxy-ethyl)-methyl-amino]-2-morpholin-4-yl-pyrido[3,2-d]pyrimidine-6-carboxylic acid

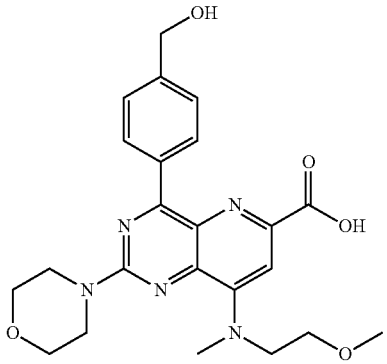 [SMILES: COCCN(C)c1cc(C(=O)O)nc2c(-c3ccc(CO)cc3)nc(N3CCOCC3)nc12]

A mixture of Intermediate 19 (0.1 g, 0.25 mmol) and N-(2-methoxyethyl)methyl amine (33 mg, 0.37 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.78 min (purity: 98%). MS (ES+): 454.0.

Example 23

8-Dimethylamino-4-(3-hydroxymethyl-phenyl)-2-morpholin-4-yl-pyrido[3,2-d]pyrimidine-6-carboxylic acid

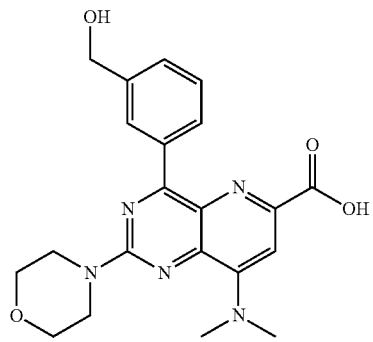

A mixture of Intermediate 21 (0.1 g, 0.25 mmol) and dimethylamine hydrochloride (30 mg, 0.37 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as an orange solid.

LC/MS (method A): RT=2.64 min (purity: 98%). MS (ES+): 409.9.

Example 24

8-[(2-Hydroxy-ethyl)-methyl-amino]-4-(3-hydroxymethyl-phenyl)-2-morpholin-4-yl-pyrido[3,2-d]pyrimidine-6-carboxylic acid

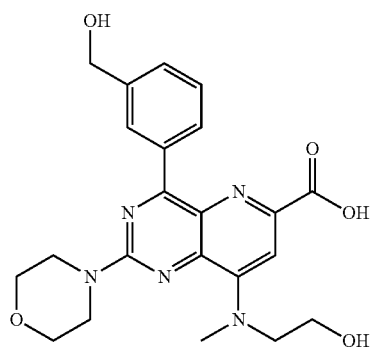

A mixture of Intermediate 21 (0.1 g, 0.25 mmol) and 2-(methyl amino)ethanol (28 mg, 0.37 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.40 min (purity: 98%). MS (ES+): 440.0.

Example 25

8-Dimethylamino-4-(3-methoxymethyl-phenyl)-2-morpholin-4-yl-pyrido[3,2-d]pyrimidine-6-carboxylic acid

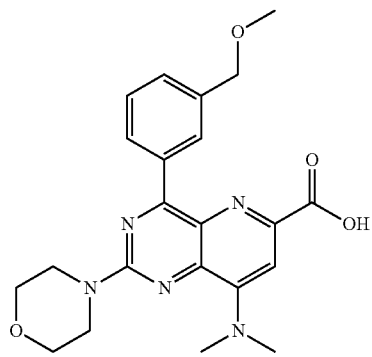 [SMILES: COCc1cccc(-c2nc(N3CCOCC3)nc3c(N(C)C)cc(C(=O)O)nc23)c1]

A mixture of Intermediate 23 (0.12 g, 0.29 mmol) and dimethylamine hydrochloride (36 mg, 0.43 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.13 min (purity: 99%). MS (ES+): 423.9

$^1$H NMR (400 MHz, DMSO-d$_6$): δ 9.11 (br s, 1H), 8.26-8.24 (m, 2H), 7.50-7.49 (m, 2H), 7.33 (s, 1H), 4.50 (s, 2H), 3.87-3.86 (m, 4H), 3.75-3.73 (m, 4H), 3.32 (s, 3H), 3.29 (s, 6H).

Example 26

8-(2-Methoxy-ethylamino)-4-(3-methoxymethyl-phenyl)-2-morpholin-4-yl-pyrido[3,2-d]pyrimidine-6-carboxylic acid

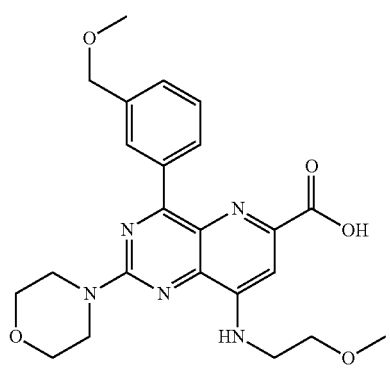 [SMILES: COCCNc1cc(C(=O)O)nc2c(-c3cccc(COC)c3)nc(N3CCOCC3)nc12]

A mixture of Intermediate 23 (0.1 g, 0.24 mmol) and 2-methoxyethylamine (27 mg, 0.36 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=3.15 min (purity: 97%). MS (ES+): 454.0.

Example 27

8-[(2-Hydroxy-ethyl)-methyl-amino]-4-(3-methoxymethyl-phenyl)-2-morpholin-4-yl-pyrido[3,2-d]pyrimidine-6-carboxylic acid

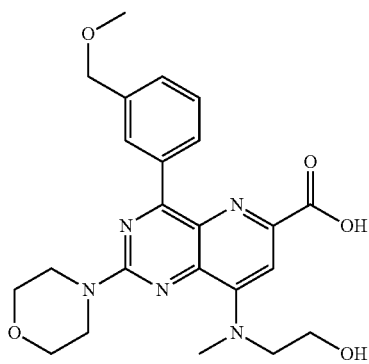 [SMILES: COCc1cccc(-c2nc(N3CCOCC3)nc3c(N(C)CCO)cc(C(=O)O)nc23)c1]

A mixture of Intermediate 23 (0.1 g, 0.24 mmol) and 2-(methyl amino) ethanol (27 mg, 0.36 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.86 min (purity: 94%). MS (ES+): 454.0.

Example 28

8-(2-Hydroxy-ethylamino)-4-(3-methoxymethyl-phenyl)-2-morpholin-4-yl-pyrido[3,2-d]pyrimidine-6-carboxylic acid

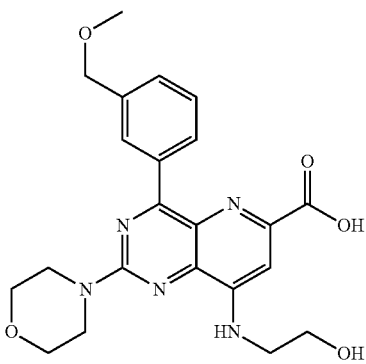 [SMILES: COCc1cccc(-c2nc(N3CCOCC3)nc3c(NCCO)cc(C(=O)O)nc23)c1]

A mixture of Intermediate 23 (0.1 g, 0.24 mmol), 2-aminoethanol (22 mg, 0.36 mmol) in DIEA (1 mL) and water (0.5 mL) was stirred at 170° C. for 2 hours. The two phases were separated and the aqueous layer concentrated in vacuo. Purification by column chromatography (increasing amount of MeOH in DCM) followed by washing with Et$_2$O afforded the title compound as a yellow solid.

LC/MS (method A): RT=2.79 min (purity: 99%). MS (ES+): 440.0.

Example 29

8-(Dimethylamino)-4-(5-fluoro-2-hydroxyphenyl)-2-morpholin-4-ylpyrido[3,2-d]pyrimidine-6-carboxylic acid

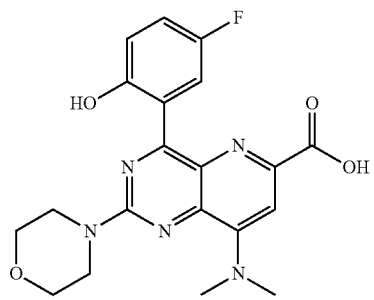 [SMILES: CN(C)c1cc(C(=O)O)nc2c(-c3cc(F)ccc3O)nc(N3CCOCC3)nc12]

The title compound was prepared as an orange solid as described for Example 15 starting from Intermediate 25 and dimethylamine hydrochloride.

LC/MS (method A): RT=3.29 min (purity: 97%). MS (ES+): 414.1.

Example 30

4-(5-Fluoro-2-hydroxyphenyl)-8-(methylamino)-2-morpholin-4-ylpyrido[3,2-d]pyrimidine-6-carboxylic acid

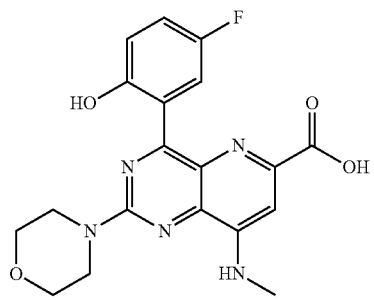

The title compound was prepared as an orange solid as described for Example 18 starting from Intermediate 25 and methylamine hydrochloride.

LC/MS (method A): RT=3.19 min (purity: 99%). MS (ES+): 400.1.

Example 31

4-(5-Fluoro-2-hydroxyphenyl)-8-[(2-methoxyethyl)amino]-2-morpholin-4-ylpyrido[3,2-d]pyrimidine-6-carboxylic acid

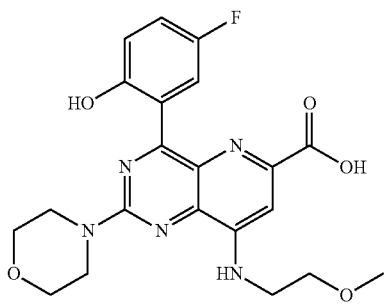 [SMILES: COCCNc1cc(C(=O)O)nc2c(-c3cc(F)ccc3O)nc(N3CCOCC3)nc12]

The title compound was prepared as a yellow solid as described for Example 26 starting from Intermediate 25 and 2-methoxyethylamine.

LC/MS (method A): RT=3.33 min (purity: 94%). MS (ES+): 444.2.

Example 32

8-[[2-(Dimethylamino)ethyl](methyl)amino]-4-(5-fluoro-2-hydroxyphenyl)-2-morpholin-4-ylpyrido[3,2-d]pyrimidine-6-carboxylic acid

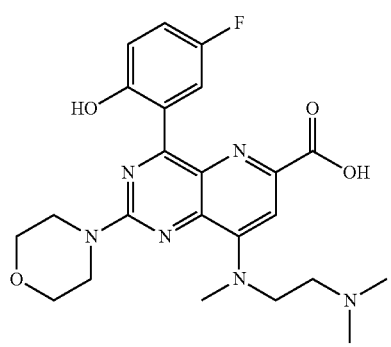 [SMILES: CN(C)CCN(C)c1cc(C(=O)O)nc2c(-c3cc(F)ccc3O)nc(N3CCOCC3)nc12]

The title compound was prepared as an orange solid as described for Example 18 starting from Intermediate 25 and N,N,N'-trimethylethane-1,2-diamine.

LC/MS (method A): RT=2.78 min (purity: 96%). MS (ES+): 471.1.

Example 33

4-(3-Fluoro-2-hydroxyphenyl)-8-[(2-methoxyethyl)(methyl)amino]-2-morpholin-4-ylpyrido[3,2-d]pyrimidine-6-carboxylic acid

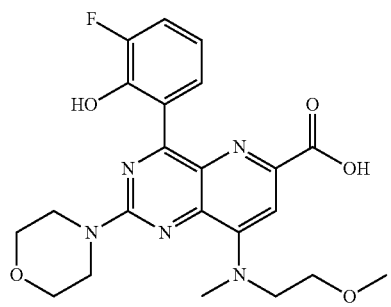 [SMILES: COCCN(C)c1cc(C(=O)O)nc2c(-c3cccc(F)c3O)nc(N3CCOCC3)nc12]

The title compound was prepared as an orange solid as described for Example 18 starting from Intermediate 27 and N-(2-methoxyethyl)methyl amine.

LC/MS (method A): RT=3.31 min (purity: 99%). MS (ES+): 457.9.

Example 34

8-(Dimethylamino)-4-(3-fluoro-2-hydroxyphenyl)-2-morpholin-4-ylpyrido[3,2-d]pyrimidine-6-carboxylic acid

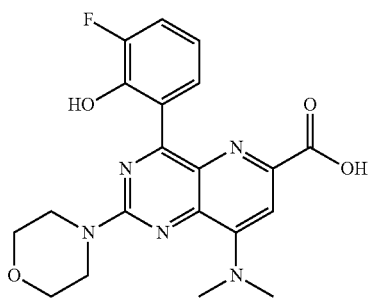 [SMILES: CN(C)c1cc(C(=O)O)nc2c(-c3cccc(F)c3O)nc(N3CCOCC3)nc12]

The title compound was prepared as an orange solid as described for Example 15 starting from Intermediate 27 and dimethylamine hydrochloride.

LC/MS (method A): RT=3.12 min (purity: 98%). MS (ES+): 414.1.

Example 35

4-(3-Fluoro-2-hydroxyphenyl)-8-(methylamino)-2-morpholin-4-ylpyrido[3,2-d]pyrimidine-6-carboxylic acid

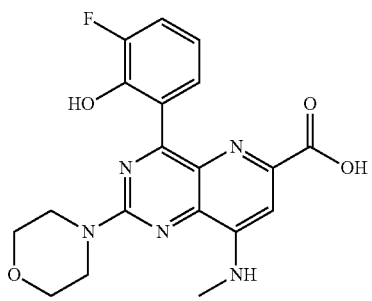

The title compound was prepared as an orange solid as described for Example 18 starting from Intermediate 27 and methylamine hydrochloride.

LC/MS (method A): RT=3.00 min (purity: 97%). MS (ES+): 400.1.

Example 36

4-(3-Fluoro-2-hydroxyphenyl)-8-[(2-methoxyethyl)amino]-2-morpholin-4-ylpyrido[3,2-d]pyrimidine-6-carboxylic acid

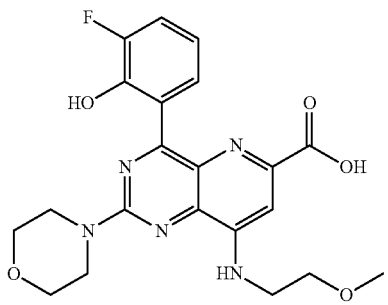 [SMILES: COCCNc1cc(C(=O)O)nc2c(-c3cccc(F)c3O)nc(N3CCOCC3)nc12]

The title compound was prepared as a brown solid as described for Example 26 starting from Intermediate 27 and 2-methoxyethylamine.

LC/MS (method A): RT=3.19 min (purity: 97%). MS (ES+): 444.2.

Example 37

4-(3-Fluoro-2-hydroxyphenyl)-8-[(2-hydroxyethyl)(methyl)amino]-2-morpholin-4-ylpyrido[3,2-d]pyrimidine-6-carboxylic acid

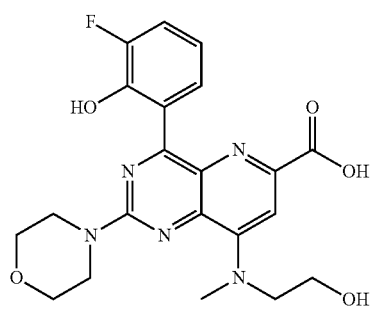 [SMILES: CN(CCO)c1cc(C(=O)O)nc2c(-c3cccc(F)c3O)nc(N3CCOCC3)nc12]

The title compound was prepared as an orange solid as described for Example 27 starting from Intermediate 27 and 2-(methylamino)ethanol.

LC/MS (method A): RT=2.80 min (purity: 99%). MS (ES+): 443.9.

Example 38

4-(3-Fluoro-2-hydroxyphenyl)-8-[(2-hydroxyethyl)amino]-2-morpholin-4-ylpyrido[3,2-d]pyrimidine-6-carboxylic acid

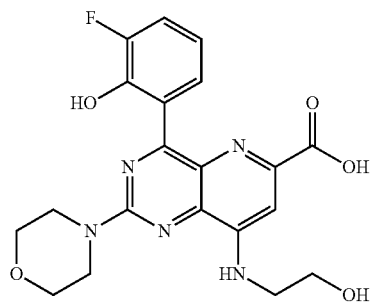

The title compound was prepared as an orange solid as described for Example 28 starting from Intermediate 27 and 2-aminoethanol.

LC/MS (method A): RT=2.76 min (purity: 98%). MS (ES+): 429.9.

Example 39

4-(3-fluoro-2-hydroxyphenyl)-8-(methyl)sulfonyl)-2-morpholin-4-ylpyrido[3,2-d]pyrimidine-6-carboxylic acid

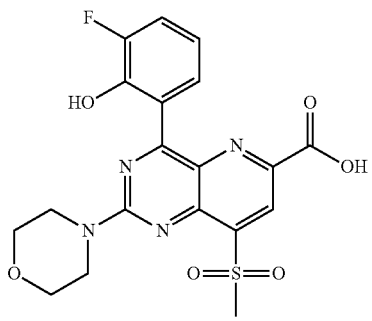

Step 1: 4-(3-Fluoro-2-hydroxyphenyl)-8-(methylthio)-2-morpholin-4-ylpyrido[3,2-d]pyrimidine-6-carboxylic acid Sodium thiomethoxide (78 mg, 1.1 mmol) was added to a solution of Intermediate 26 (155 mg, 0.37 mmol) in DMF (5 mL) and the reaction mixture was stirred at 115° C. for 16 hours in a sealed tube. The solution was diluted with DCM, washed with sat. aq. $NH_4Cl$ then brine, dried over magnesium sulfate and concentrated in vacuo. The residue was washed with cold ACN to afford the title compound as a yellow solid.

LC/MS (method A): RT=1.97 min (purity: 98%). MS (ES+): 417.0.

Step 2: 4-(3-Fluoro-2-hydroxyphenyl)-8-(methylsulfonyl)-2-morpholin-4-ylpyrido[3,2-d]pyrimidine-6-carboxylic acid 30% hydrogen peroxide (1 mL) was added at 0° C. over 30 minutes to a solution of 4-(3-fluoro-2-hydroxyphenyl)-8-(methylthio)-2-morpholin-4-ylpyrido[3,2-d]pyrimidine-6-carboxylic acid (104 mg, 0.25 mmol) and sodium tungstate dihydrate (250 mg, 0.07 mmol) in methanol (5 mL) and the resulting mixture was stirred at room temperature for 3 hours then concentrated in vacuo. The residue was taken up in DCM, washed with sat. aq. $NH_4Cl$ then brine, dried over magnesium sulfate and concentrated in vacuo. Purification by column chromatography (increasing amount of MeOH in DCM) afforded the title compound as an orange solid.

LC/MS (method A): RT=3.75 min (purity: 98%). MS (ES+): 449.1.

Example 40

4-(3-Hydroxyphenyl)-8-(methylamino)-2-morpholin-4-ylpyrido[3,2-d]pyrimidine-6-carboxylic acid

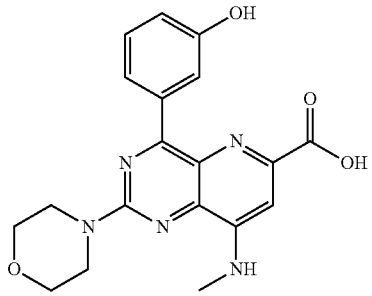 [SMILES: CNc1cc(C(=O)O)nc2c(-c3cccc(O)c3)nc(N3CCOCC3)nc12]

The title compound was prepared as a yellow solid as described for Example 18 starting from Example 9 and methylamine hydrochloride.

LC/MS (method A): RT=2.64 min (purity: 99%). MS (ES+): 381.9.

Example 41

4-(3-Hydroxyphenyl)-2-morpholin-4-ylpyrido[3,2-d]pyrimidine-6-carboxylic acid

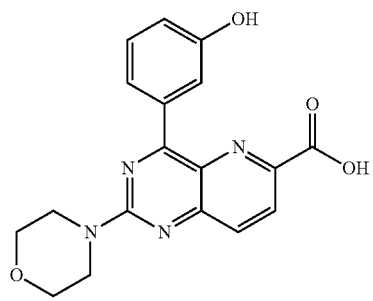 [SMILES: O=C(O)c1ccc2nc(N3CCOCC3)nc(-c3cccc(O)c3)c2n1]

The title compound was prepared as a yellow solid as described for Intermediate 10 and Example 8 starting from Intermediate 11.

LC/MS (method A): RT=3.12 min (purity: 97%). MS (ES+): 352.9.

Example 42

8-(Dimethylamino)-4-(2-hydroxyphenyl)-2-morpholin-4-ylpyrido[3,2-d]pyrimidine-6-carboxylic acid

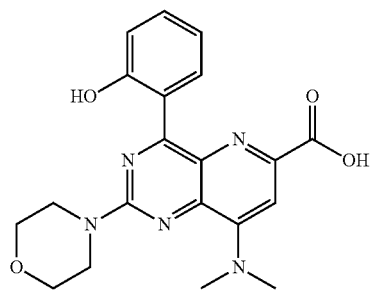 [SMILES: CN(C)c1cc(C(=O)O)nc2c(-c3ccccc3O)nc(N3CCOCC3)nc12]

The title compound was prepared as a yellow solid as described for Example 15 starting from Intermediate 29 and dimethylamine hydrochloride.

LC/MS (method A): RT=3.08 min (purity: 97%). MS (ES+): 395.9.

Example 43

8-[[2-(Dimethylamino)ethyl](methyl)amino]-4-(2-hydroxyphenyl)-2-morpholin-4-ylpyrido[3,2-d]pyrimidine-6-carboxylic acid

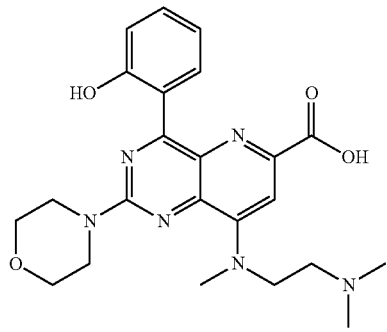 [SMILES: CN(C)CCN(C)c1cc(C(=O)O)nc2c(-c3ccccc3O)nc(N3CCOCC3)nc12]

The title compound was prepared as a yellow solid as described for Example 18 starting from Intermediate 29 and N,N,N'-trimethylethane-1,2-diamine.

LC/MS (method A): RT=2.56 min (purity: 94%). MS (ES+): 453.0.

Example 44

8-[(2-Hydroxyethyl)amino]-4-(2-hydroxyphenyl)-2-morpholin-4-ylpyrido[3,2-d]pyrimidine-6-carboxylic acid

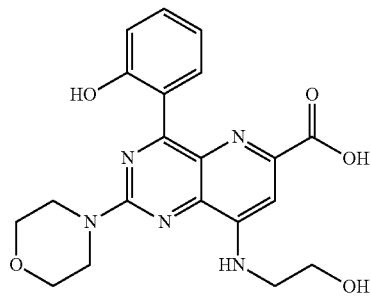 [SMILES: O=C(O)c1cc(NCCO)c2nc(N3CCOCC3)nc(-c3ccccc3O)c2n1]

The title compound was prepared as a yellow solid as described for Example 28 starting from Intermediate 29 and 2-aminoethanol.

LC/MS (method A): RT=2.75 min (purity: 97%). MS (ES+): 412.0.

Example 45

4-(3-Fluoro-4-hydroxyphenyl)-8-(methylsulfonyl)-2-morpholin-4-ylpyrido[3,2-d]pyrimidine-6-carboxylic acid

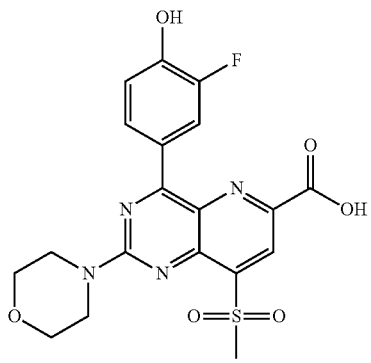

The title compound was prepared as a yellow solid as described for Example 39 starting from Intermediate 30 and sodium thiomethoxide.

LC/MS (method A): RT=3.44 min (purity: 96%). MS (ES+): 449.1.

Example 46

4-[4-(Hydroxymethyl)phenyl]-8-[(2-methoxyethyl)amino]-2-morpholin-4-ylpyrido[3,2-d]pyrimidine-6-carboxylic acid

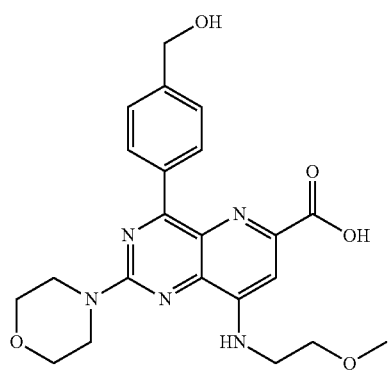 [SMILES: COCCNc1cc(C(=O)O)nc2c(-c3ccc(CO)cc3)nc(N3CCOCC3)nc12]

The title compound was prepared as a yellow solid as described for Example 26 starting from Intermediate 19 and 2-methoxyethylamine.

LC/MS (method A): RT=2.64 min (purity: 97%). MS (ES+): 440.0.

Example 47

4-[3-(Hydroxymethyl)phenyl]-8-[(2-methoxyethyl)(methyl)amino]-2-morpholin-4-ylpyrido[3,2-d]pyrimidine-6-carboxylic acid

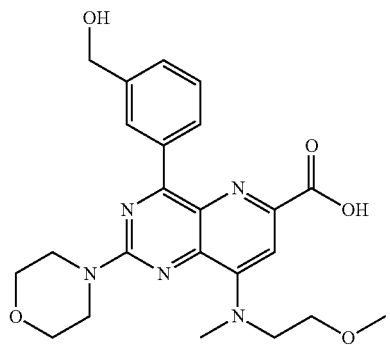 [SMILES: COCCN(C)c1cc(C(=O)O)nc2c(-c3cccc(CO)c3)nc(N3CCOCC3)nc12]

The title compound was prepared as a yellow solid as described for Example 22 starting from Intermediate 21 and N-(2-methoxyethyl)methyl amine.

LC/MS (method A): RT=2.81 min (purity: 100%). MS (ES+): 454.0.

Example 48

8-[(2-Hydroxyethyl)amino]-4-[3-(hydroxymethyl)phenyl]-2-morpholin-4-ylpyrido[3,2-d]pyrimidine-6-carboxylic acid

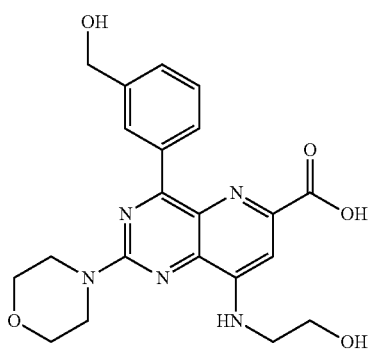 [SMILES: O=C(O)c1cc(NCCO)c2nc(N3CCOCC3)nc(-c3cccc(CO)c3)c2n1]

The title compound was prepared as a yellow solid as described for Example 28 starting from Intermediate 21 and 2-aminoethanol.

LC/MS (method A): RT=2.33 min (purity: 100%). MS (ES+): 426.0.

Example 49

8-(Dimethylamino)-4-[4-fluoro-3-(hydroxymethyl)phenyl]-2-morpholin-4-ylpyrido[3,2-d]pyrimidine-6-carboxylic acid

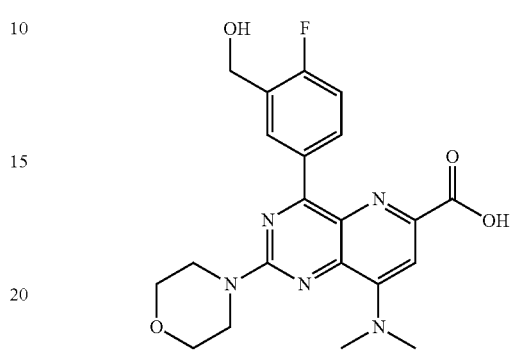

The title compound was prepared as a yellow solid as described for Example 15 starting from Intermediate 33 and dimethylamine hydrochloride.

LC/MS (method A): RT=2.81 min (purity: 97%). MS (ES+): 428.1.

Example 50

4-[4-Fluoro-3-(hydroxymethyl)phenyl]-8-[(2-hydroxyethyl)(methyl)amino]-2-morpholin-4-ylpyrido[3,2-d]pyrimidine-6-carboxylic acid

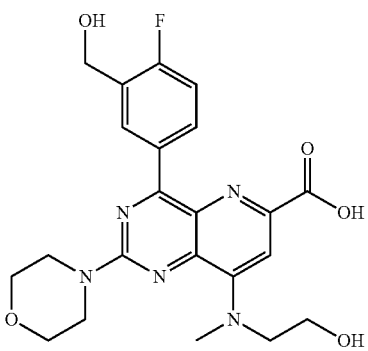 [SMILES: CN(CCO)c1cc(C(=O)O)nc2c(-c3ccc(F)c(CO)c3)nc(N3CCOCC3)nc12]

The title compound was prepared as a yellow solid as described for Example 27 starting from Intermediate 33 and 2-(methylamino)ethanol.

LC/MS (method A): RT=2.52 min (purity: 97%). MS (ES+): 457.9.

Example 51

4-(4-Fluoro-2-hydroxyphenyl)-8-[(2-methoxyethyl)(methyl)amino]-2-morpholin-4-ylpyrido[3,2-d]pyrimidine-6-carboxylic acid

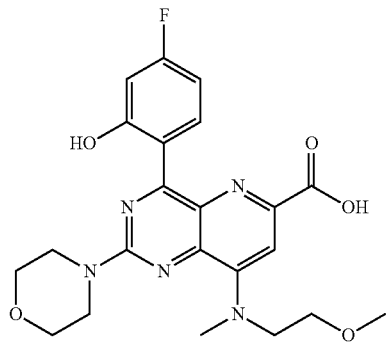 [SMILES: COCCN(C)c1cc(C(=O)O)nc2c(-c3ccc(F)cc3O)nc(N3CCOCC3)nc12]

The title compound was prepared as a yellow solid as described for Example 22 starting from Intermediate 35 and N-(2-methoxyethyl)methyl amine.

LC/MS (method A): RT=3.44 min (purity: 91%). MS (ES+): 458.2.

Example 52

8-(Dimethylamino)-4-(4-fluoro-2-hydroxyphenyl)-2-morpholin-4-ylpyrido[3,2-d]pyrimidine-6-carboxylic acid

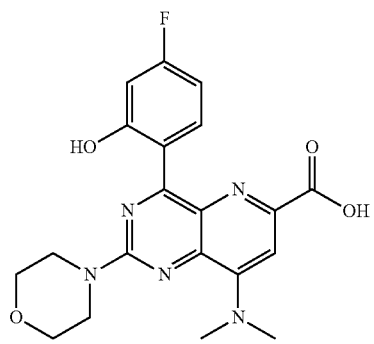 [SMILES: CN(C)c1cc(C(=O)O)nc2c(-c3ccc(F)cc3O)nc(N3CCOCC3)nc12]

The title compound was prepared as a yellow solid as described for Example 15 starting from Intermediate 35 and dimethylamine hydrochloride.

LC/MS (method A): RT=3.28 min (purity: 94%). MS (ES+): 414.1.

Example 53

4-(4-Fluoro-2-hydroxyphenyl)-8-(methylamino)-2-morpholin-4-ylpyrido[3,2-d]pyrimidine-6-carboxylic acid

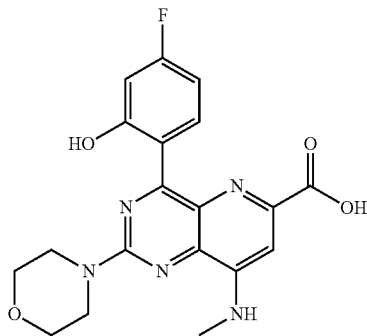 [SMILES: CNc1cc(C(=O)O)nc2c(-c3ccc(F)cc3O)nc(N3CCOCC3)nc12]

The title compound was prepared as an orange solid as described for Example 18 starting from Intermediate 35 and methylamine hydrochloride.

LC/MS (method A): RT=3.15 min (purity: 98%). MS (ES+): 400.1.

Example 54

4-(4-Fluoro-2-hydroxyphenyl)-8-[(2-methoxyethyl)amino]-2-morpholin-4-ylpyrido[3,2-d]pyrimidine-6-carboxylic acid

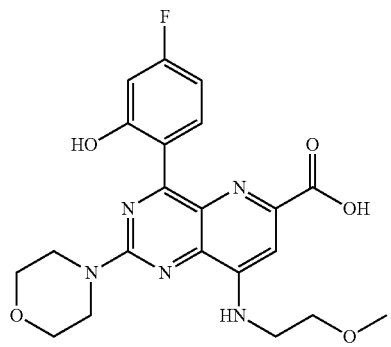 [SMILES: COCCNc1cc(C(=O)O)nc2c(-c3ccc(F)cc3O)nc(N3CCOCC3)nc12]

The title compound was prepared as an orange solid as described for Example 26 starting from Intermediate 35 and 2-methoxyethylamine.

LC/MS (method A): RT=3.34 min (purity: 91%). MS (ES+): 443.9.

Example 55

4-(5-Fluoro-2-hydroxyphenyl)-8-(methylsulfonyl)-2-morpholin-4-ylpyrido[3,2-d]pyrimidine-6-carboxylic acid

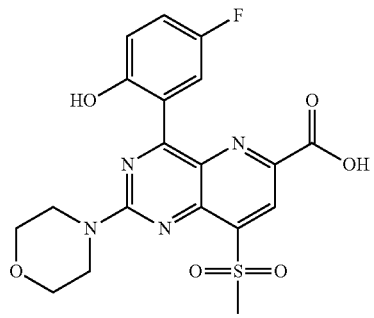 [SMILES: CS(=O)(=O)c1cc(C(=O)O)nc2c(-c3cc(F)ccc3O)nc(N3CCOCC3)nc12]

The title compound was prepared as an orange solid as described for Example 39 starting from Intermediate 24 and sodium thiomethoxide.

LC/MS (method A): RT=3.83 min (purity: 97%). MS (ES+): 449.1.

Example 56

4-(3-Fluoro-5-hydroxyphenyl)-8-(methylsulfonyl)-2-morpholin-4-ylpyrido[3,2-d]pyrimidine-6-carboxylic acid

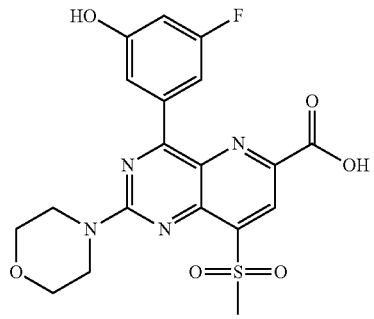 [SMILES: CS(=O)(=O)c1cc(C(=O)O)nc2c(-c3cc(O)cc(F)c3)nc(N3CCOCC3)nc12]

The title compound was prepared as a yellow solid as described for Example 39 starting from Intermediate 12 and sodium thiomethoxide.

LC/MS (method A): RT=3.57 min (purity: 93%). MS (ES+): 448.7.

Example 57

8-[[2-(Dimethylamino)ethyl](methyl)amino]-4-(1H-indol-4-yl)-2-morpholin-4-ylpyrido[3,2-d]pyrimidine-6-carboxylic acid

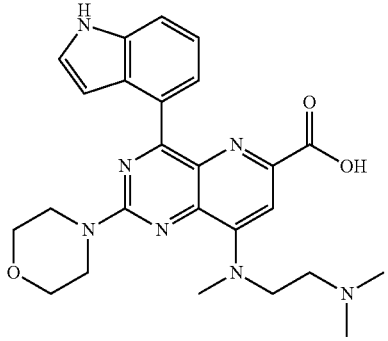 [SMILES: CN(C)CCN(C)c1cc(C(=O)O)nc2c(-c3cccc4[nH]ccc34)nc(N3CCOCC3)nc12]

The title compound was prepared as a brown solid as described for Example 18 starting from Intermediate 15 and N,N,N'-trimethylethane-1,2-diamine.

LC/MS (method A): RT=2.42 min (purity: 93%). MS (ES+): 476.0.

Example 58

8-[(2-Hydroxyethyl)(methyl)amino]-4-(4-hydroxy-2-methylphenyl)-2-morpholin-4-ylpyrido[3,2-d]pyrimidine-6-carboxylic acid

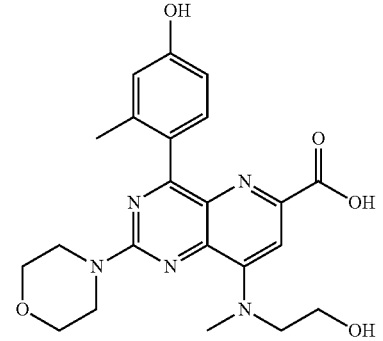 [SMILES: Cc1cc(O)ccc1-c1nc(N2CCOCC2)nc2c(N(C)CCO)cc(C(=O)O)nc12]

The title compound was prepared as a yellow solid as described for Example 27 starting from Intermediate 38 and 2-(methylamino)ethanol.

LC/MS (method A): RT=2.57 min (purity: 97%). MS (ES+): 440.0.

Example 59

4-(4-Fluoro-2-hydroxyphenyl)-8-[(2-hydroxyethyl)(methyl)amino]-2-morpholin-4-ylpyrido[3,2-d]pyrimidine-6-carboxylic acid,

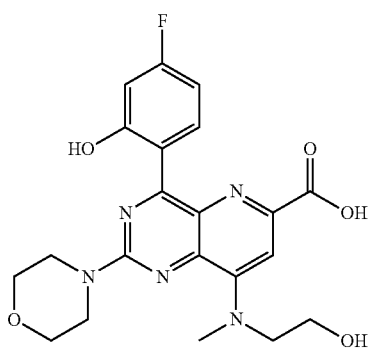 [SMILES: CN(CCO)c1cc(C(=O)O)nc2c(-c3ccc(F)cc3O)nc(N3CCOCC3)nc12]

The title compound was prepared as an orange solid as described for Example 27 starting from Intermediate 35 and 2-(methylamino)ethanol.

LC/MS (method A): RT=2.97 min (purity: 92%). MS (ES+): 443.9.

Example 60

8-(4-Acetylpiperazin-1-yl)-4-(3-hydroxyphenyl)-2-morpholin-4-ylpyrido[3,2-d]pyrimidine-6-carboxylic acid

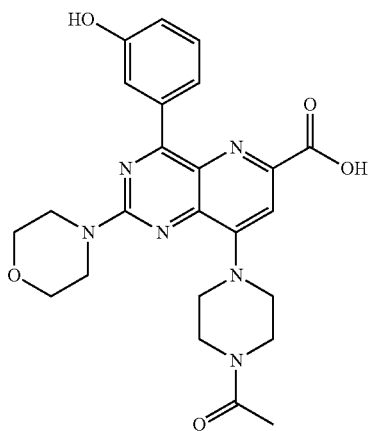 [SMILES: CC(=O)N1CCN(c2cc(C(=O)O)nc3c(-c4cccc(O)c4)nc(N4CCOCC4)nc23)CC1]

Acetyl chloride (5.4 mg; 0.07 mmol) was added dropwise at 0° C. to a solution of Intermediate 36 (30 mg, 0.07 mmol) in DCM (10 mL) and the reaction mixture was stirred at room temperature for 18 hours. The solution was partitioned between water and DCM and the two phases separated. The organic layer was dried over magnesium sulfate and concentrated in vacuo. The residue was taken up in a mixture of THF and 1M NaOH and stirred at room temperature for one hour. The THF was evaporated in vacuo and the aqueous layer neutralized with 1M HCl. The precipitate was filtered off and dried to afford the title compound as an orange solid.

HPLC (Method B): RT=2.62 min (purity: 95%). MS (ES+): 479.0.

$^1$H NMR (300 MHz, DMSO-$d_6$): δ 7.82 (d, J=9.0 Hz, 1H), 7.72 (s, 1H), 7.51 (s, 1H), 7.32 (t, J=9.0 Hz, 1H), 6.99 (dd, J=9.0, 3.0 Hz, 1H), 3.89-3.60 (m, 16H), 2.07 (s, 3H), 6.15-5.02 (m, 2H).

Example 61

4-(3-Hydroxyphenyl)-8-[4-(methylsulfonyl)piperazin-1-yl]-2-morpholin-4-ylpyrido[3,2-d]pyrimidine-6-carboxylic acid

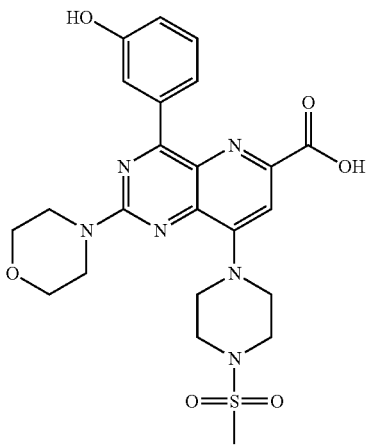 [SMILES: CS(=O)(=O)N1CCN(c2cc(C(=O)O)nc3c(-c4cccc(O)c4)nc(N4CCOCC4)nc23)CC1]

A mixture of Example 9 (130 mg; 0.34 mmol), 1-(methylsulfonyl)piperazine (276 mg; 1.68 mmol) and N,N-diethylethanamine (170 mg; 1.68 mmol) in THF (3 mL) and water (3 mL) was stirred at 115° C. for 48 hours then concentrated in vacuo. The residue was taken up in EA, washed with aq. citric acid, dried over magnesium sulfate and concentrated in vacuo. Purification by column chromatography (EA/EtOH/AcOH, 90/10/1) afforded the title compound as an orange solid.

HPLC (Method B): RT=3.09 min (purity: 96%). MS (ES+): 515.0.

$^1$H NMR (300 MHz, DMSO-$d_6$): δ 7.81-7.78 (m, 2H), 7.57 (s, 1H), 7.28 (t, J=9.0 Hz, 1H), 6.93 (dd, J=9.0, 3.0 Hz, 1H), 3.91-3.87 (m, 4H), 3.80-3.76 (m, 8H), 3.40-3.37 (m, 4H), 2.89 (s, 3H), 4.30-4.20 (m, 2H).

Example 62

4-(3-Hydroxyphenyl)-8-methyl-2-morpholin-4-ylpyrido[3,2-d]pyrimidine-6-carboxylic acid

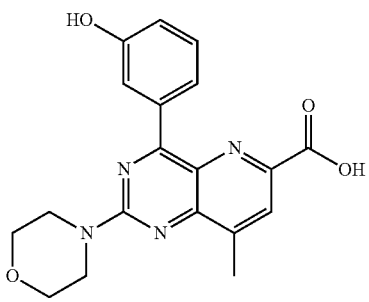 [SMILES: Cc1cc(C(=O)O)nc2c(-c3cccc(O)c3)nc(N3CCOCC3)nc12]

A mixture of Example 9 (30 mg; 0.08 mmol), Pd(PPh$_3$)$_4$ (4.5 mg) and 2M methylzinc chloride (0.16 mL, 0.31 mmol) in THF (5 mL) was stirred at 80° C. for 16 hours then concentrated in vacuo. The residue was partitioned between EA and aq. citric acid and the two phases separated. The aqueous layer was dried over magnesium sulfate and concentrated in vacuo. Purification by column chromatography (EA/EtOH/AcOH, 90/10/1) afforded the title compound as a yellow solid.

HPLC (Method B): RT=4.00 min (purity: 87%). MS (ES+): 367.0.

Example 63

4-(3-Hydroxyphenyl)-2-morpholin-4-yl-8-(1-naphthyl)pyrido[3,2-d]pyrimidine-6-carboxylic acid

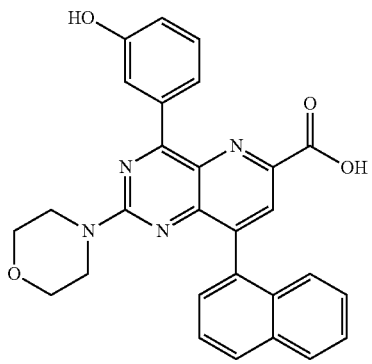 [SMILES: O=C(O)c1cc(-c2cccc3ccccc23)c2nc(N3CCOCC3)nc(-c3cccc(O)c3)c2n1]

A mixture of Example 9 (145 mg; 0.37 mmol), 1-naphthylboronic acid (142 mg; 0.82 mmol), cesium carbonate (489 mg; 1.50 mmol) and Pd(PPh$_3$)$_4$ (87 mg; 0.07 mmol) in DMF (4 mL) was stirred at 150° C. for one hour (microwave heating) then concentrated in vacuo. The residue was partitioned between EA and aq. citric acid and the two phases separated. The aqueous layer was dried over magnesium sulfate and concentrated in vacuo. Precipitation from EA/Et$_2$O afforded the title compound as a yellow solid.

HPLC (Method B): RT=4.38 min (purity: 96%). MS (ES−): 477.2.

$^1$H NMR (300 MHz, DMSO-d$_6$): δ 12.96 (s, 1H), 9.67 (s, 1H), 8.23-8.00 (m, 2H), 7.81 (s, 1H), 7.66-7.44 (m, 9H), 7.06-7.01 (m, 1H), 3.56-3.32 (m, 8H).

Example 64

8-Chloro-2-morpholin-4-yl-4-phenylpyrido[3,2-d]pyrimidine-6-carboxylic acid

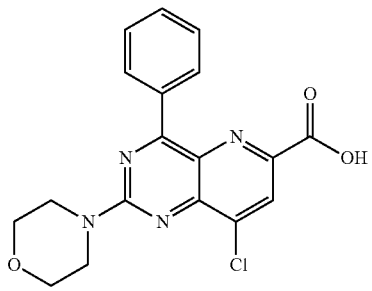 [SMILES: O=C(O)c1cc(Cl)c2nc(N3CCOCC3)nc(-c3ccccc3)c2n1]

A mixture of Intermediate 39 (200 mg; 0.52 mmol) and 1M NaOH (5.2 mL, 5.2 mmol) in THF (4 mL) was stirred at room temperature for 3 hours then acidified to pH 2 with 1M HCl. Extraction with DCM, drying over magnesium sulfate and concentration in vacuo afforded the title compound (183 mg, 95%) as a yellow solid.

HPLC (Method B): RT=4.16 min (purity: 96%). MS (ES+): 370.9

$^1$H NMR (300 MHz, DMSO-d$_6$): δ 13.52 (s, 1H), 8.40 (dd, J=8.0, 1.5 Hz, 2H), 8.37 (s, 1H), 7.65-7.54 (m, 3H), 4.07-3.98 (m, 4H), 3.80-3.72 (m, 4H).

Example 65

4-(3,5-Difluorophenyl)-8-[(2-methoxyethyl)(methyl)amino]-2-morpholin-4-ylpyrido[3,2-d]pyrimidine-6-carboxylic acid

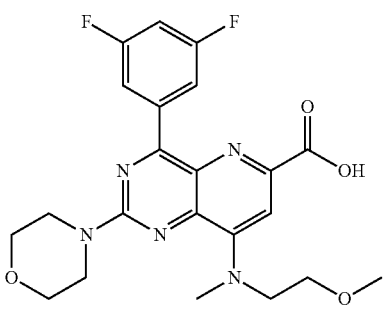 [SMILES: COCCN(C)c1cc(C(=O)O)nc2c(-c3cc(F)cc(F)c3)nc(N3CCOCC3)nc12]

A mixture of Intermediate 41 (176 mg; 0.43 mmol), N-(2-methoxyethyl)methylamine (46 mg; 0.52 mmol) in water (10 mL) and N-ethyldiisopropylamine (0.15 mL; 0.87 mmol) was stirred at 170° C. for 3 hours (microwave heating) then concentrated in vacuo. Purification by column chromatography (increasing amount of MeOH in DCM) followed by mass triggered preparative HPLC afforded the title compound as a yellow solid.

HPLC (Method B): RT=3.18 min (purity: 98%). MS (ES+): 460.0

$^1$H NMR (300 MHz, DMSO-d$_6$): δ 13.79-12.51 (m, 1H), 8.31 (d, J=7.9 Hz, 2H), 7.51-7.42 (m, 1H), 7.34 (s, 1H), 4.22 (t, J=6.0 Hz, 2H), 3.88-3.80 (m, 4H), 3.78-3.71 (m, 4H), 3.62 (t, J=6.0 Hz, 2H), 3.21 (s, 3H), 3.14 (s, 3H).

Example 66

4-(3-Cyanophenyl)-8-(dimethylamino)-2-morpholin-4-ylpyrido[3,2-d]pyrimidine-6-carboxylic acid

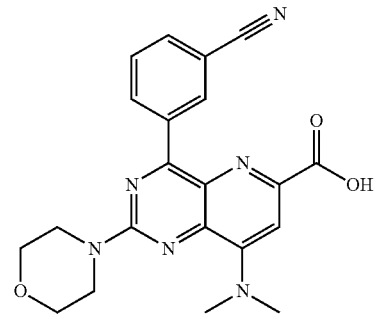 [SMILES: CN(C)c1cc(C(=O)O)nc2c(-c3cccc(C#N)c3)nc(N3CCOCC3)nc12]

A mixture of Intermediate 43 (122 mg; 0.31 mmol) and 40% dimethylamine (3.00 mL; 23.90 mmol) was stirred at 150° C. for 5 minutes (microwave heating) then concentrated in vacuo. Purification by mass triggered preparative HPLC afforded the title compound as a yellow solid.

HPLC (Method B): RT=2.67 min (purity: 100%). MS (ES+): 405.2.

$^1$H NMR (300 MHz, DMSO-$d_6$): δ 13.06 (s, 1H), 8.89 (s, 1H), 8.68 (d, J=8.0 Hz, 1H), 8.06-8.02 (m, 1H), 7.76 (t, J=8.0 Hz, 1H), 7.34 (s, 1H), 3.92-3.85 (m, 4H), 3.79-3.72 (m, 4H), 3.32 (s, 6H).

Example 67

8-[4-(Methylsulfonyl)piperazin-1-yl]-2-morpholin-4-yl-4-phenylpyrido[3,2-d]pyrimidine-6-carboxylic acid

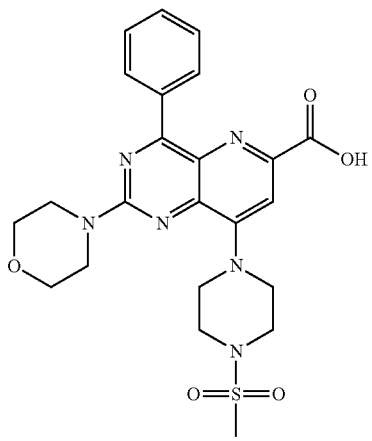 [SMILES: CS(=O)(=O)N1CCN(c2cc(C(=O)O)nc3c(-c4ccccc4)nc(N4CCOCC4)nc23)CC1]

A mixture of Intermediate 43 (150 mg; 0.4 mmol), 1-methanesulfonyl-piperazine (531 mg; 3.24 mmol) and triethylamine (0.11 mL; 0.81 mmol) in THF (5 mL) and water (5 mL) was stirred at 105° C. for 16 hours then concentrated in vacuo. The residue was taken up in 0.5M NaOH, washed with DCM and acidified to pH 2 with 1M HCl. Extraction with DCM, drying over magnesium sulfate, concentration in vacuo and purification by column chromatography afforded the title compound (40 mg, 20%) as a yellow powder.

HPLC (Method B): RT=3.62 min (purity: 98%). MS (ES+): 499.0.

$^1$H NMR (300 MHz, DMSO-$d_6$): δ 7.99-7.96 (m, 2H), 7.54-7.48 (m, 4H), 3.97-3.69 (m, 12H), 3.42-3.38 (m, 4H), 2.80 (s, 3H).

Example 68

Biological Assays

The efficacy of compounds of the invention in inhibiting the PI3K induced-lipid phosphorylation may be tested in the following binding assay. The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin. To a 96 wells MTP containing 10 μl of the test compound of Formula (I) (solubilized in 10% DMSO; to yield a concentration of 100, 25, 5.0, 1.25, 0.312, 0.078, 0.0195, 0.00488, 0.00122 and 0.0003 μM of the test compound), the following assay components are added: 1) 10 μL of lipid micelles 2) 20 mL of Kinase buffer ([$^{33}$P]γATP162 μM/300 nCi, $MgCl_2$ 2.5 mM, DTT 2.5 mM, $Na_3VO_4$ 25 μM in Hepes 40 mM, pH 7.4) and 3) 10 μL (100 ng) of Human recombinant GST-PI3K (in Hepes 40 mM, pH 7.4, ethylenglycol 4%). After incubation at room temperature for 120 minutes, with gentle agitation, the reaction is stopped by addition of 200 μL of a solution containing 250 μg of neomycin-coated PVT SPA beads, ATP 60 mM and EDTA 6.2 mM in PBS. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter. The values indicated in Table I below refer to the $IC_{50}$ (μM) with respect to PI3K, i.e. the amount necessary to achieve 50% inhibition of said target. Said values show a considerable inhibitory potency of pyridopyrimidine compounds with regard to PI3K.

Examples of inhibitory activities for compounds according to the invention are set out in Table I below.

TABLE I

| Example No | structures | Pi3K (IC50) (μM) |
|---|---|---|
| 1 | 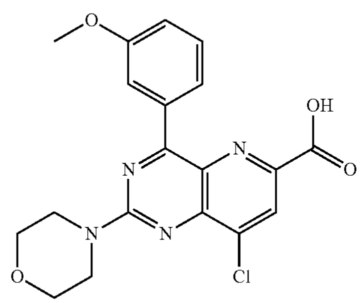 [SMILES: COc1cccc(-c2nc(N3CCOCC3)nc3c(Cl)cc(C(=O)O)nc23)c1] | 1.08 |
| 2 | 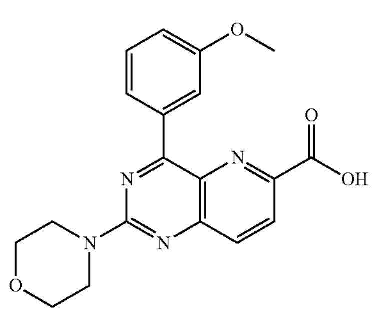 [SMILES: COc1cccc(-c2nc(N3CCOCC3)nc3ccc(C(=O)O)nc23)c1] | 4.49 |

TABLE I-continued
| Example No | structures | Pi3K (IC50) (μM) |
|---|---|---|
| 3 | 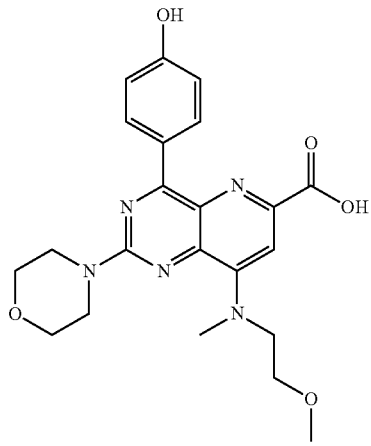 [SMILES: COCCN(C)c1cc(C(=O)O)nc2c(-c3ccc(O)cc3)nc(N3CCOCC3)nc12] | 0.290 |
| 4 | 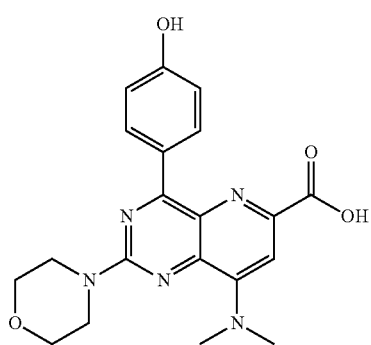 [SMILES: CN(C)c1cc(C(=O)O)nc2c(-c3ccc(O)cc3)nc(N3CCOCC3)nc12] | 0.350 |
| 5 | 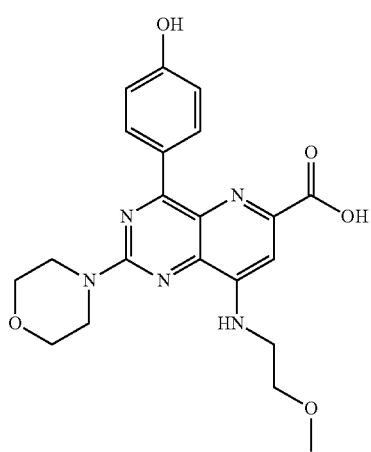 [SMILES: COCCNc1cc(C(=O)O)nc2c(-c3ccc(O)cc3)nc(N3CCOCC3)nc12] | 0.504 |
TABLE I-continued
| Example No | structures | Pi3K (IC50) (μM) |
|---|---|---|
| 6 | 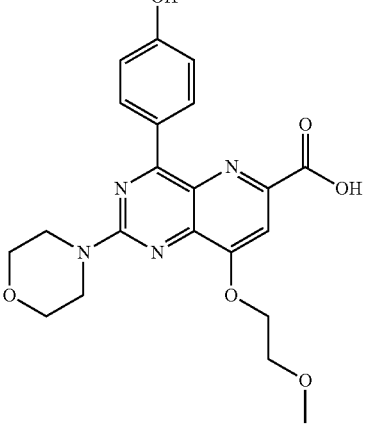 | 2.520 |
| 7 | 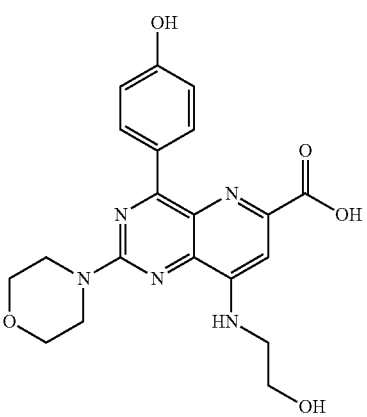 [SMILES: O=C(O)c1cc(NCCO)c2nc(N3CCOCC3)nc(-c3ccc(O)cc3)c2n1] | 0.732 |
| 8 | 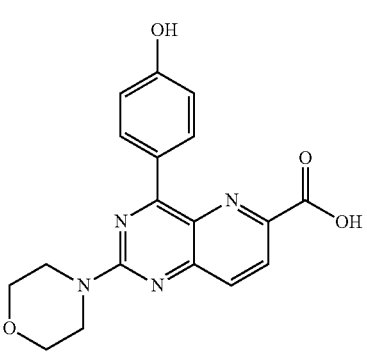 [SMILES: O=C(O)c1ccc2nc(N3CCOCC3)nc(-c3ccc(O)cc3)c2n1] | 0.855 |
| 9 | 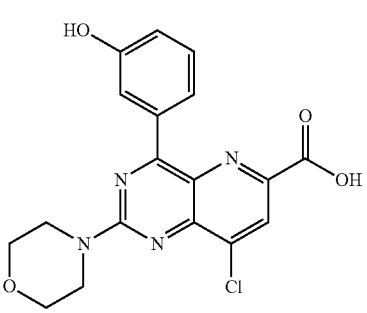 [SMILES: O=C(O)c1cc(Cl)c2nc(N3CCOCC3)nc(-c3cccc(O)c3)c2n1] | 0.108 |

TABLE I-continued
| Example No | structures | Pi3K (IC50) (μM) |
|---|---|---|
| 10 | 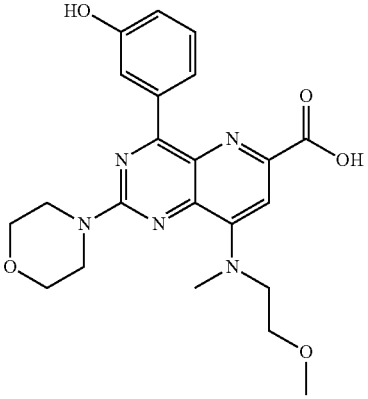 [SMILES: COCCN(C)c1cc(C(=O)O)nc2c(-c3cccc(O)c3)nc(N3CCOCC3)nc12] | 0.028 |
| 11 | 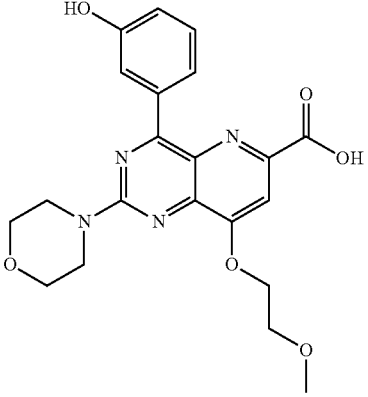 [SMILES: COCCOc1cc(C(=O)O)nc2c(-c3cccc(O)c3)nc(N3CCOCC3)nc12] | 0.255 |
| 12 | 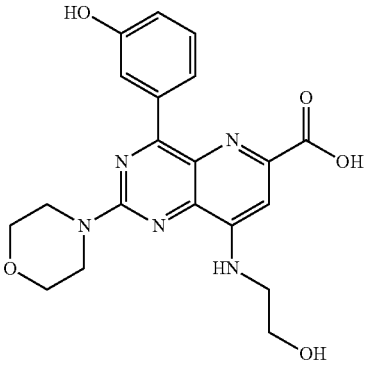 [SMILES: O=C(O)c1cc(NCCO)c2nc(N3CCOCC3)nc(-c3cccc(O)c3)c2n1] | 0.075 |
| 13 | 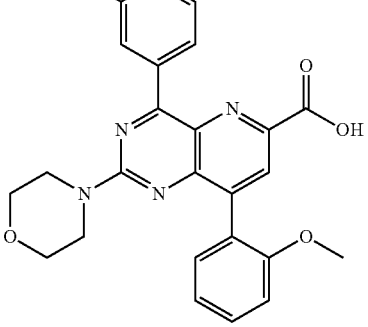 | 0.024 |
| 14 | 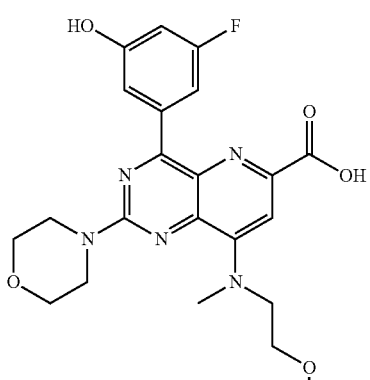 | 0.019 |
| 15 | 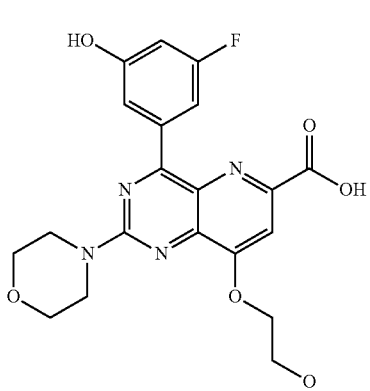 [SMILES: O=C(O)c1cc(NCCO)c2nc(N3CCOCC3)nc(-c3cc(O)cc(F)c3)c2n1] | 0.093 |
| 16 | 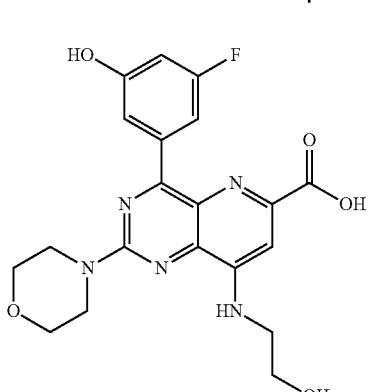 | 0.064 |
| 17 | 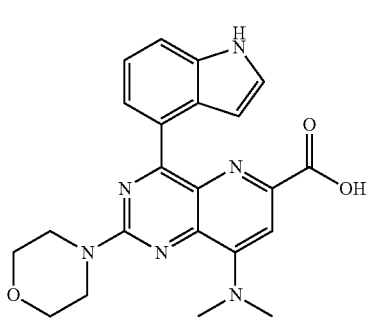 [SMILES: CN(C)c1cc(C(=O)O)nc2c(-c3cccc4[nH]ccc34)nc(N3CCOCC3)nc12] | 0.132 |

TABLE I-continued

| Example No | structures | Pi3K (IC50) (μM) |
|---|---|---|
| 18 | (structure) | 0.780 |
| 19 | (structure) | 0.128 |
| 20 | (structure) | 0.077 |
| 21 | (structure) | 0.169 |
| 22 | (structure) | 0.546 |
| 23 | (structure) | 0.034 |
| 24 | (structure) | 0.074 |
| 25 | (structure) | 5.050 |

TABLE I-continued

| Example No | structures | Pi3K (IC50) (μM) |
|---|---|---|
| 26 | (structure) | 1.830 |
| 27 | (structure) | 1.850 |
| 28 | (structure) | 2.490 |
| 29 | (structure) | 0.066 |
| 30 | (structure) | 0.304 |
| 31 | (structure) | 0.073 |
| 32 | (structure) | 0.564 |
| 33 | (structure) | 0.009 |

TABLE I-continued

| Example No | structures | Pi3K (IC50) (μM) |
|---|---|---|
| 34 | 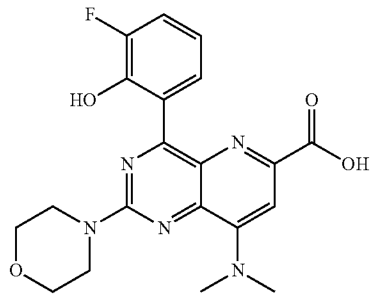 [SMILES: CN(C)c1cc(C(=O)O)nc2c(-c3cccc(F)c3O)nc(N3CCOCC3)nc12] | 0.013 |
| 35 | 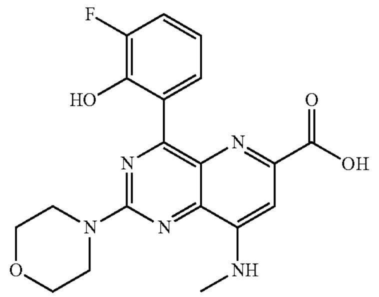 [SMILES: CNc1cc(C(=O)O)nc2c(-c3cccc(F)c3O)nc(N3CCOCC3)nc12] | 0.048 |
| 36 | 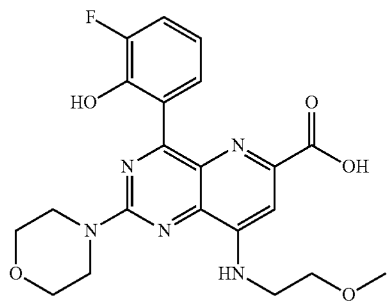 [SMILES: COCCNc1cc(C(=O)O)nc2c(-c3cccc(F)c3O)nc(N3CCOCC3)nc12] | 0.018 |
| 37 | 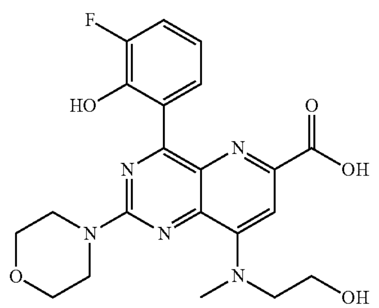 [SMILES: CN(CCO)c1cc(C(=O)O)nc2c(-c3cccc(F)c3O)nc(N3CCOCC3)nc12] | 0.010 |
| 38 | 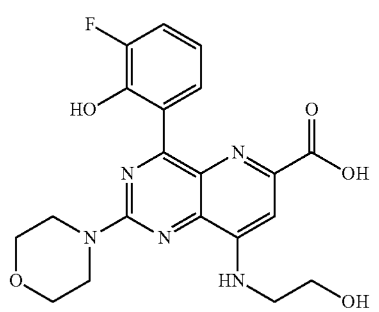 [SMILES: O=C(O)c1cc(NCCO)c2nc(N3CCOCC3)nc(-c3cccc(F)c3O)c2n1] | 0.043 |
| 39 | | 0.026 |
| 40 | | 0.144 |
| 41 | | 0.063 |
| 42 | | 0.023 |
| 43 | | 0.459 |

TABLE I-continued
| Example No | structures | Pi3K (IC50) (μM) |
|---|---|---|
| 44 | 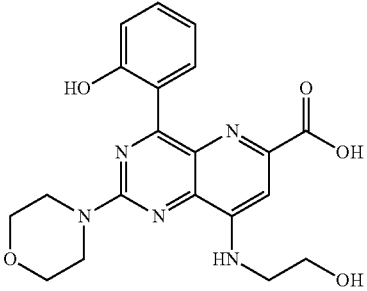 [SMILES: O=C(O)c1cc(NCCO)c2nc(N3CCOCC3)nc(-c3ccccc3O)c2n1] | 0.082 |
| 45 | 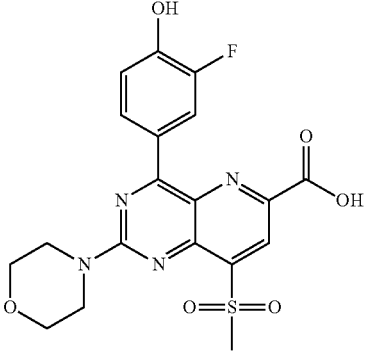 [SMILES: CS(=O)(=O)c1cc(C(=O)O)nc2c(-c3ccc(O)c(F)c3)nc(N3CCOCC3)nc12] | 0.335 |
| 46 | 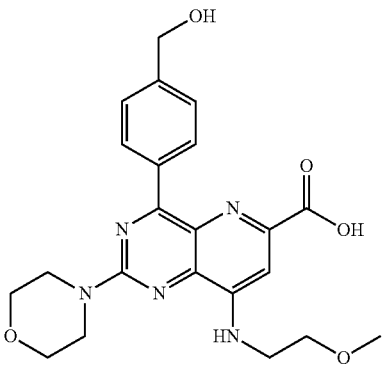 [SMILES: COCCNc1cc(C(=O)O)nc2c(-c3ccc(CO)cc3)nc(N3CCOCC3)nc12] | 0.346 |
| 47 | 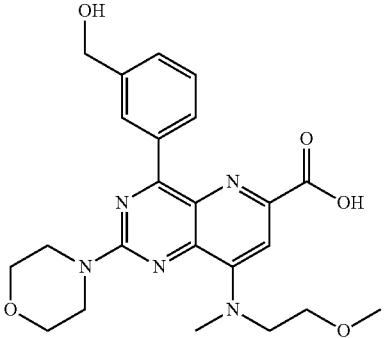 [SMILES: COCCN(C)c1cc(C(=O)O)nc2c(-c3cccc(CO)c3)nc(N3CCOCC3)nc12] | 0.008 |
TABLE I-continued
| Example No | structures | Pi3K (IC50) (μM) |
|---|---|---|
| 48 | 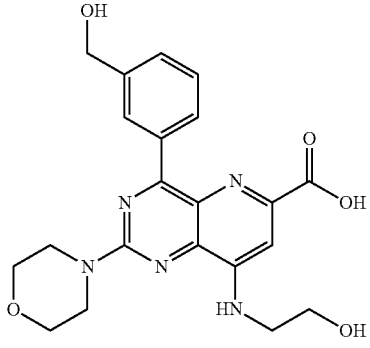 [SMILES: O=C(O)c1cc(NCCO)c2nc(N3CCOCC3)nc(-c3cccc(CO)c3)c2n1] | 0.027 |
| 49 | 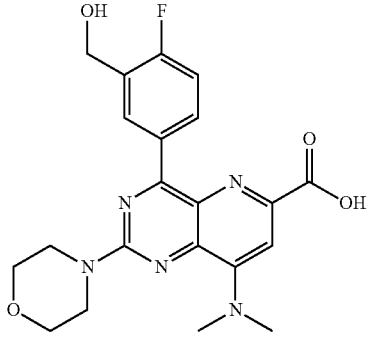 [SMILES: CN(C)c1cc(C(=O)O)nc2c(-c3ccc(F)c(CO)c3)nc(N3CCOCC3)nc12] | 0.329 |
| 50 | 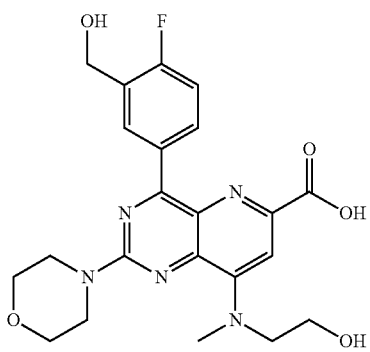 [SMILES: CN(CCO)c1cc(C(=O)O)nc2c(-c3ccc(F)c(CO)c3)nc(N3CCOCC3)nc12] | 0.303 |
| 51 | 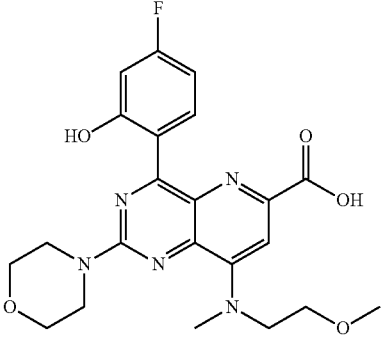 [SMILES: COCCN(C)c1cc(C(=O)O)nc2c(-c3ccc(F)cc3O)nc(N3CCOCC3)nc12] | 0.062 |

TABLE I-continued

| Example No | structures | Pi3K (IC50) (μM) |
|---|---|---|
| 52 | (structure) | 0.083 |
| 53 | (structure) | 0.412 |
| 54 | (structure) | 0.089 |
| 55 | (structure) | 0.139 |
| 56 | (structure) | 0.015 |
| 57 | (structure) | 0.137 |
| 58 | (structure) | 0.936 |
| 59 | (structure) | 0.220 |

TABLE I-continued

| Example No | structures | Pi3K (IC50) (µM) |
|---|---|---|
| 60 | (structure) | 0.080 |
| 61 | (structure) | 0.015 |
| 62 | (structure) | 0.225 |
| 63 | (structure) | 0.057 |
| 64 | (structure) | 0.678 |
| 65 | (structure) | 1.290 |
| 66 | (structure) | 1.100 |
| 67 | (structure) | 0.030 |

Example 69

Preparation of a Pharmaceutical Formulation

Formulation 1—Tablets

A compound of formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of formula (I) is dissolved in a buffered sterile saline injectable aqueous medium to a concentration of approximately 5 mg/mL.

The invention claimed is:

1. A compound of Formula (I):

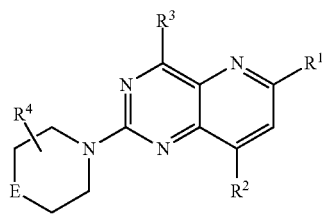

wherein:

$R^1$ denotes perfluoroalkyl, $-NH_2$, $-NA_2$, $A^*$, $-NH$-$A$, $-NH-(CH_2)_p$-$A$, $-SO$-$A$, $SO_2$-$A$, $-COOR^T$, $-(CH_2)_p-OR^T$, $-(CH_2)_p-SR^T$, $-COA$, $-CO$-Het, $-CO-N(H)_{2-m}(A)_m$, $-SO-N(H)_{2-m}(A)_m$, $SO_2-N(H)_{2-m}(A)_m$, $N(H)_{1-q}A_qSOA$, $N(H)_{1-q}A_qSO_2A$, $-(CH_2)_p-N(H)_{2-m}(A)_m$, $-CO-NH-(CH_2)_p-N(H)_{2-m}(A)_m$, $-(CH_2)_p-NH-(CH_2)_p-N(H)_{2-m}(A)_m$, Ar*, or Het, $R^2$ denotes H, Hal, $CF_3$, A, Ar, Het, SA, OA, OH, $-SOA$, $-SO_2A$, $-OCO$-$A$, $-N(H)_{2-m}(A)_m$, $-NH-(CH_2)_p-N(H)_{2-m}(A)_m$, $-NA$-$(CH_2)_p-N(H)_{2-m}(A)_m$, $-NA$-$(CH_2)_p-OR^T$, $-NH-(CH_2)_p-OA$, $-(CH_2)_p$Het, $-(CH_2)_p-N(H)_{2-m}(A)_m$, $-O(CH_2)_pOR^T$, or $-N(R^T)_2$, E denotes O, S, $CHR^T$, or $NR^T$, $R^3$ denotes Ar, Het, $R^4$ denotes H, perfluoroalkyl, $-NH_2$, $-NA_2$, A, $-NH$-$A$, $-NH-(CH_2)_p$-$A$, $-SO$-$A$, $SO_2$-$A$, $-COOR^T$, $-(CH_2)_p-OR^T$, $-(CH_2)_p-SR^T$, $-COA$, $-CO$-Het, $-CO-N(H)_{2-m}(A)_m$, $-SO-N(H)_{2-m}(A)_m$, $SO_2-N(H)_{2-m}(A)_m$, $-N(H)_{1-q}A_qSOA$, $N(H)_{1-q}A_qSO_2A$, $-(CH_2)_p-N(H)_{2-m}(A)_m$, $-CO-NH-(CH_2)_p-N(H)_{2-m}(A)_m$, $-(CH_2)_p-NH-(CH_2)_p-N(H)_{2-m}(A)_m$, Ar, or Het, $R^T$ denotes H, A, Ar, or Het, Ar denotes a monocyclic or bicyclic, aromatic carbocyclic ring having 6 to 14 carbon atoms, which is unsubstituted or monosubstituted, disubstituted or trisubstituted by, Hal, $CF_3$, $OCF_3$, $NO_2$, CN, perfluoroalkyl, A, OA, OH, $NH_2$, COH, $CONH_2$, $-NHCOA$, $-NHSO_2A$, $-NHSO_2-N(H)_{2-m}(A)_m$, $N(H)_{1-q}A_qCOA$, $N(H)_{1-q}A_qSO_2-N(H)_{2-m}(A)_m$, $-N(H)_{1-q}A_qCON(H)_{2-m}(A)_m$, $-COOA$, $-SO_2A$, $-SO_2N(H)_{2-m}(A)_m$, $-SO_2$Het, $-(CH_2)_p-N(H)_{2-m}(A)_m$, and/or $-(CH_2)_p-OR^T$, or disubstituted or trisubstituted by OH and 1 or 2 of above described substituents, Ar* denotes a monocyclic or bicyclic, aromatic carbocyclic ring having 6 to 14 carbon atoms, which is monosubstituted, disubstituted or trisubstituted by, Hal, $CF_3$, $OCF_3$, $NO_2$, CN, perfluoroalkyl, A, OA, OH, $NH_2$, COH, $CONH_2$, $-NHCOA$, $-NHSO_2A$, $-NHSO_2-N(H)_{2-m}(A)_m$, $N(H)_{1-q}A_qCOA$, $N(H)_{1-q}A_qSO_2-N(H)_{2-m}(A)_m$, $-N(H)_{1-q}A_qCON(H)_{2-m}(A)_m$, $-COOA$, $-SO_2A$, $-SO_2N(H)_{2-m}(A)_m$, $-SO_2$Het, $-(CH_2)_p-N(H)_{2-m}(A)_m$, and/or $-(CH_2)_p-OR^T$, or disubstituted or trisubstituted by OH and 1 or 2 of above described substituents, Het denotes a monocyclic or bicyclic saturated, unsaturated or aromatic heterocyclic ring having 1, 2, 3 or 4 N, O and/or S atoms which is unsubstituted or monosubstituted, disubstituted or trisubstituted by alkyl having 1 to 8 carbon atoms, alkoxy having 1 to 8 carbon atoms, Hal, $CF_3$, $OCF_3$, $NO_2$, CN, perfluoroalkyl, A, OA, OH, $NH_2$, COH, $CONH_2$, $-NHCOA$, $-NHSO_2A$, $-NHSO_2-N(H)_{2-m}(A)_m$, $N(H)_{1-q}A_qCOA$, $N(H)_{1-q}A_qSO_2-N(H)_{2-m}(A)_m$, $-N(H)_{1-q}A_qCON(H)_{2-m}(A)_m$, $-COOA$, $-SO_2A$, $-SO_2N(H)_{2-m}(A)_m$, $-SO_2$Het, $-(CH_2)_p-N(H)_{2-m}(A)_m$, and/or $-(CH_2)_p-OR^T$, m denotes 0, 1 or 2, p denotes 0, 1, 2, 3 or 4, q denotes 0 or 1, A is a branched or linear alkyl having 1 to 12 C-atoms, wherein one or more, H-atoms may be replaced by Hal, Ar, Het, $OR^6$, $-CN$, $-COO$alkyl or $N(R^6)_2$ and wherein one or more, non-adjacent $CH_2$-groups may be replaced by O, $NR^6$ or S and/or by $-CH=CH-$ or $-C\equiv C-$groups, or A denotes cycloalkyl or cycloalkylalkylene having 3-7 ring C atoms, A* is a branched or linear alkyl having 2 to 12 C-atoms, wherein one or more, H-atoms may be replaced by Hal, Ar, Het, $OR^6$, $-CN$, $-COO$alkyl or $N(R^6)_2$ and wherein one or more, non-adjacent $CH_2$-groups may be replaced by O, $NR^6$ or S and/or by $-CH=CH-$ or $-C\equiv C-$groups, or A* denotes cycloalkyl or cycloalkylalkylene having 3-7 ring C atoms, $R^6$ is H, A, $-(CH_2)_p-N(H)_{2-m}(A)_m$, $-(CH_2)_p-OA$; or $CH_2NH_2$, and tautomers, salts and stereoisomers thereof.

2. The compound of Formula (I) according to claim 1, wherein R³ is selected from the following groups:

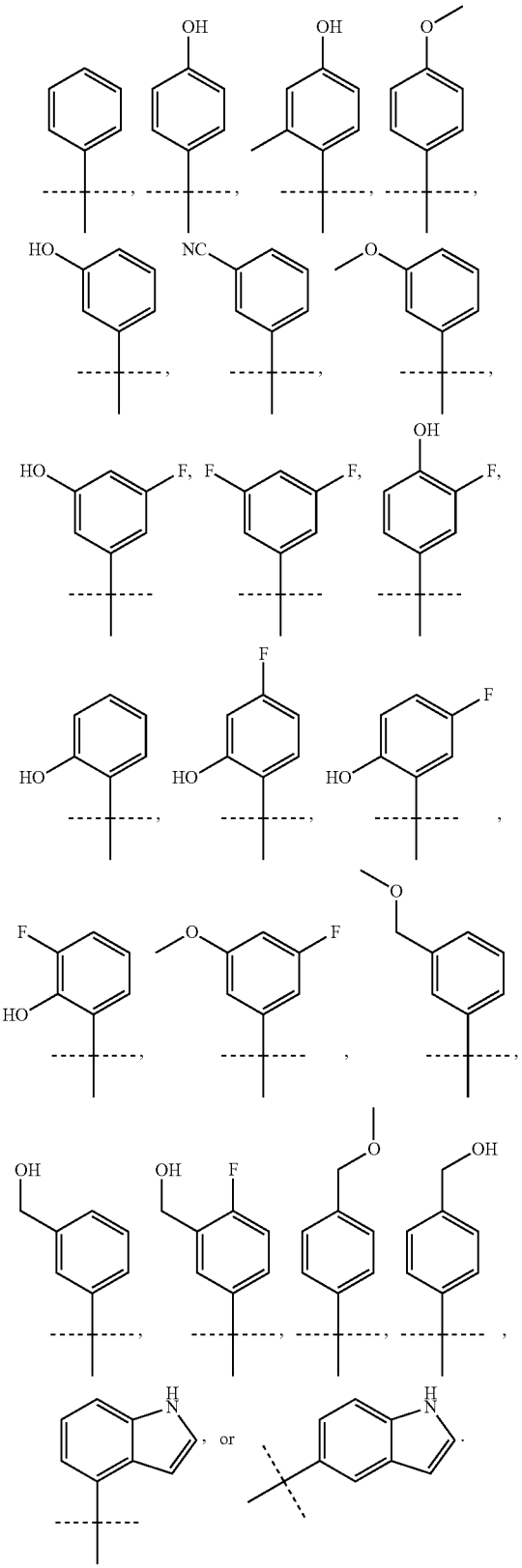

3. The compound according to claim 1, wherein said compound is of Formula (I')

(I')

wherein R² is as defined in claim 1,
X denotes CO, CS, or CH₂,
B denotes O, N, S, SO, SO₂ or a bond,
W denotes H, A, —(CH₂)$_p$—N(H)$_{2-m}$(A)$_m$, or —(CH₂)$_p$—OA,
Y is 1 or 2,
R$^a$ and R$^b$ denote independently from one another H, OH, OA, Hal, —(CH₂)$_p$OH, —(CH₂)$_p$OA, or —(CH₂)$_p$—N(H)$_{2-m}$(A)$_m$,
m and p are as defined in claim 1,
A is a branched or linear alkyl having 1 to 12 C-atoms, wherein one or more H-atoms may be replaced by Hal, Ar, Het, OR⁶, —CN, —COOalkyl or N(R⁶)₂ and wherein one or more, non-adjacent CH₂-groups may be replaced by O, NR⁶ or S and/or by —CH═CH— or —C≡C— groups, or A denotes cycloalkyl or cycloalkylalkylene having 3-7 ring C atoms,
and salts or stereoisomers thereof.

4. The compound according to claim 1, wherein said compound is of Formula (I'')

(I'')

wherein:
R² is as defined in claim 1,
X denotes CO, CS, or CH₂,
B denotes O, N, S, SO, SO₂ or a bond,
W denotes H, A, —(CH₂)$_p$—N(H)$_{2-m}$(A)$_m$, or —(CH₂)$_p$—OA,
Y is 1 or 2,
R$^a$ denotes H, OH, OA, Hal, —(CH₂)$_p$OH, —(CH₂)$_p$OA, or —(CH₂)$_p$—N(H)$_{2-m}$(A)$_m$,
L denotes H or A,
m and p are as defined in claim 1,
A is a branched or linear alkyl having 1 to 12 C-atoms, wherein one or more, H-atoms may be replaced by Hal, Ar, Het, OR⁶, —CN, —COOalkyl or N(R⁶)₂ and wherein one or more non-adjacent CH₂-groups may be replaced by O, NR⁶ or S and/or by —CH=CH— or —C≡C—groups, or A denotes cycloalkyl or cycloalkylalkylene having 3-7 ring C atoms, and pharmaceutically acceptable derivatives, solvates, tautomers, salts and stereoisomers thereof, including mixtures thereof in all ratios.

5. The compound of Formula (I) according to claim 1, said compound being selected from:

| Ex. No | Structures |
|---|---|
| 1 | 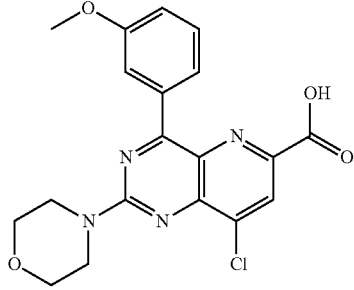 [SMILES: COc1cccc(-c2nc(N3CCOCC3)nc3c(Cl)cc(C(=O)O)nc23)c1] |
| 2 | 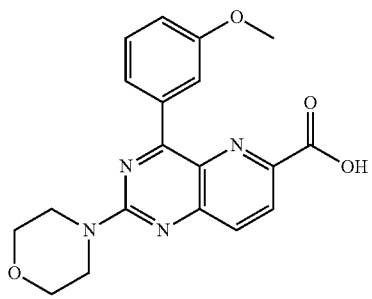 [SMILES: COc1cccc(-c2nc(N3CCOCC3)nc3ccc(C(=O)O)nc23)c1] |
| 3 | 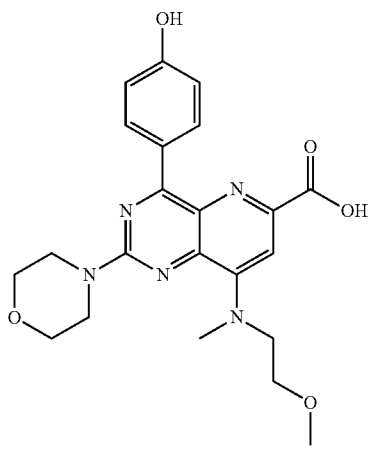 [SMILES: COCCN(C)c1cc(C(=O)O)nc2c(-c3ccc(O)cc3)nc(N3CCOCC3)nc12] |

-continued

| Ex. No | Structures |
|---|---|
| 4 | 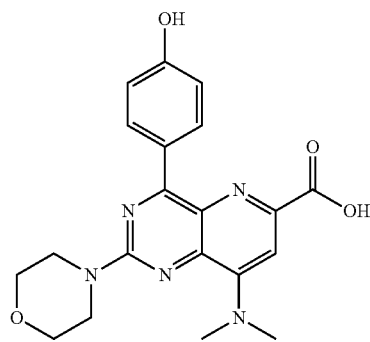 [SMILES: CN(C)c1cc(C(=O)O)nc2c(-c3ccc(O)cc3)nc(N3CCOCC3)nc12] |
| 5 | 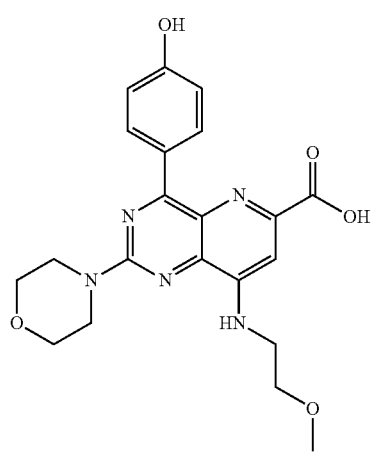 [SMILES: COCCNc1cc(C(=O)O)nc2c(-c3ccc(O)cc3)nc(N3CCOCC3)nc12] |
| 6 | 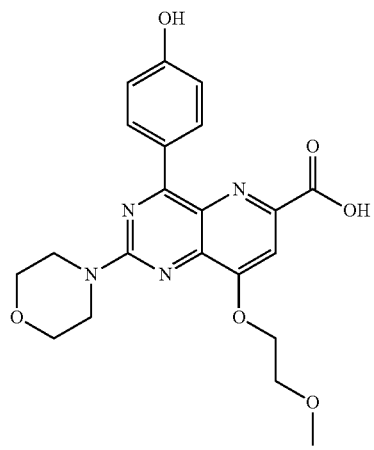 [SMILES: COCCOc1cc(C(=O)O)nc2c(-c3ccc(O)cc3)nc(N3CCOCC3)nc12] |

-continued
| Ex. No | Structures |
|---|---|
| 7 | 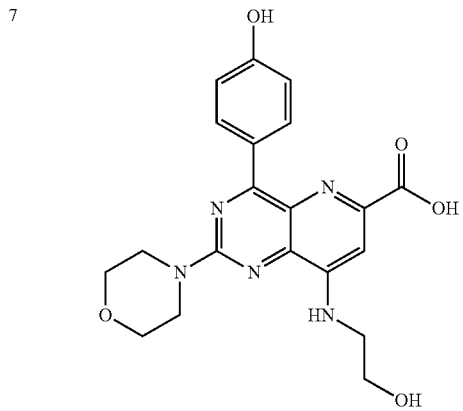 |
| 8 | 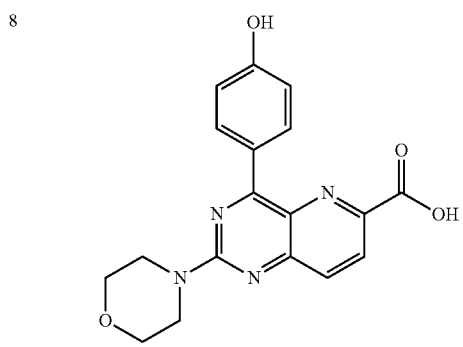 |
| 9 | 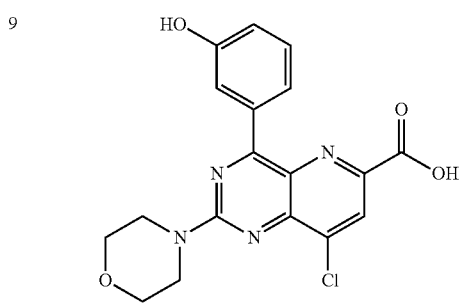 |
| 10 | 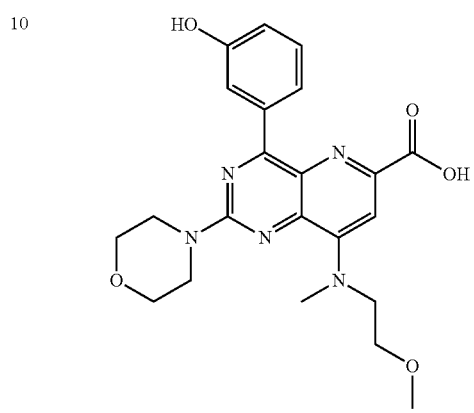 |
-continued
| Ex. No | Structures |
|---|---|
| 11 | 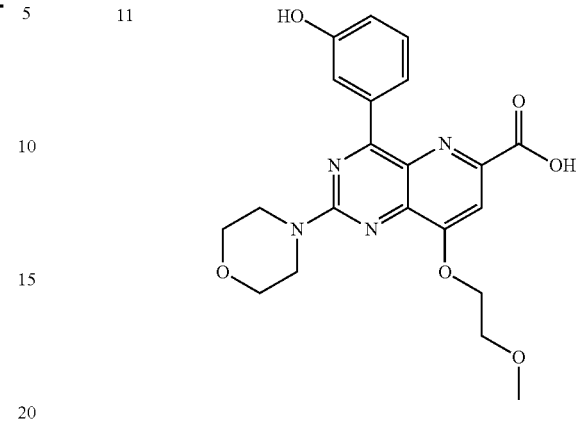 |
| 12 | 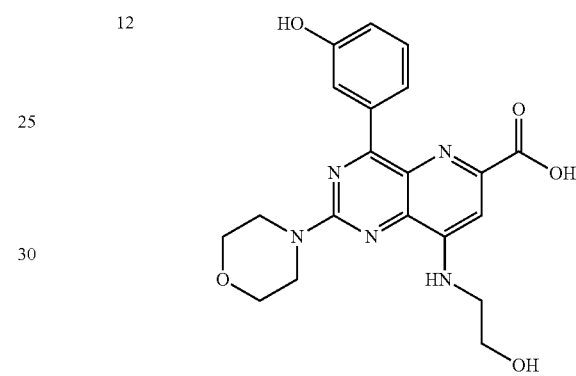 |
| 13 | 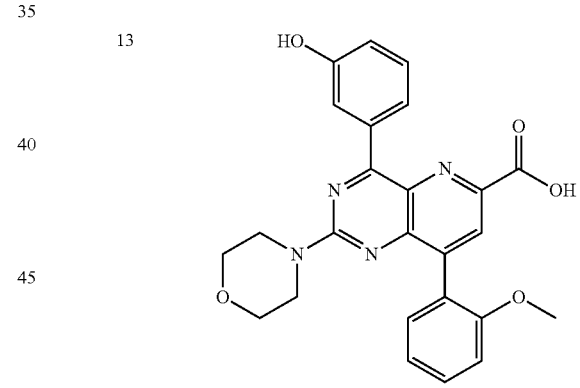 |
| 14 | 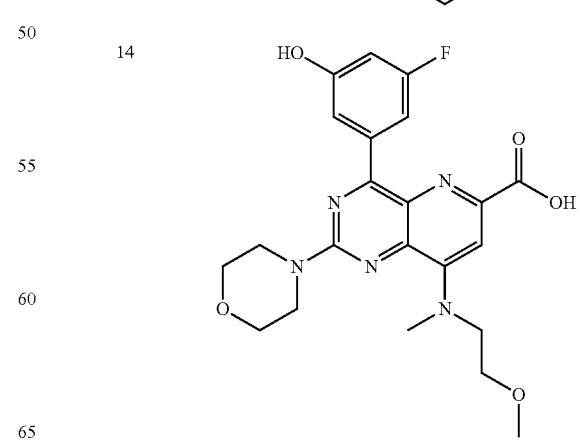 |

-continued
| Ex. No | Structures |
|---|---|
| 15 | 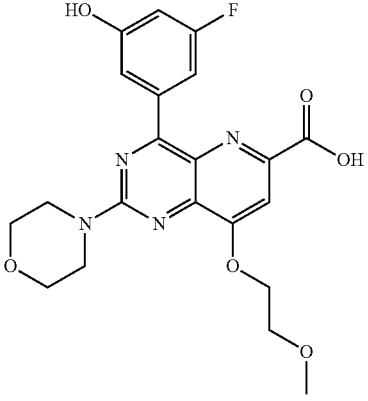 [SMILES: COCCOc1cc(C(=O)O)nc2c(-c3cc(O)cc(F)c3)nc(N3CCOCC3)nc12] |
| 16 | 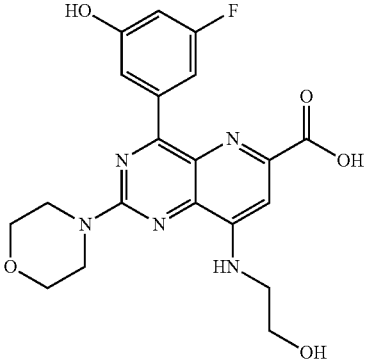 [SMILES: O=C(O)c1cc(NCCO)c2nc(N3CCOCC3)nc(-c3cc(O)cc(F)c3)c2n1] |
| 17 | 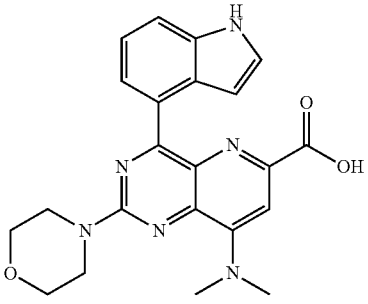 [SMILES: CN(C)c1cc(C(=O)O)nc2c(-c3cccc4[nH]ccc34)nc(N3CCOCC3)nc12] |
| 18 | 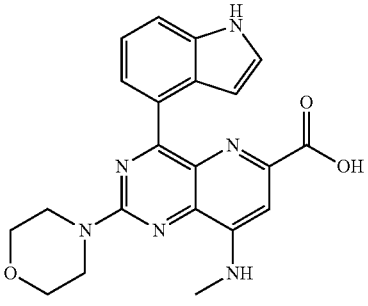 |
-continued
| Ex. No | Structures |
|---|---|
| 19 | 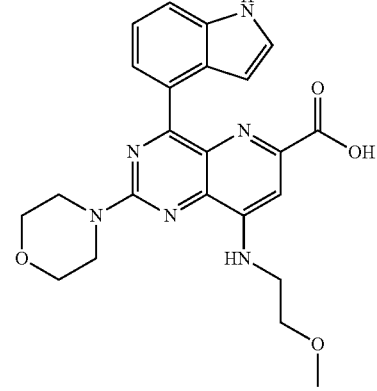 |
| 20 | 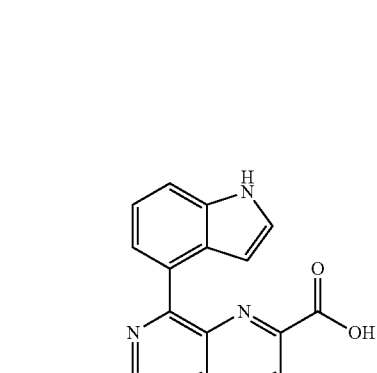 |
| 21 | 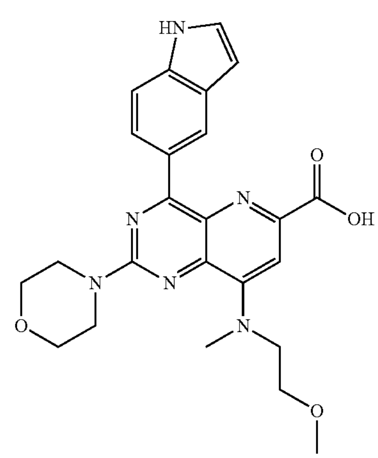 [SMILES: COCCN(C)c1cc(C(=O)O)nc2c(-c3ccc4[nH]ccc4c3)nc(N3CCOCC3)nc12] |

| Ex. No | Structures |
|---|---|
| 22 | 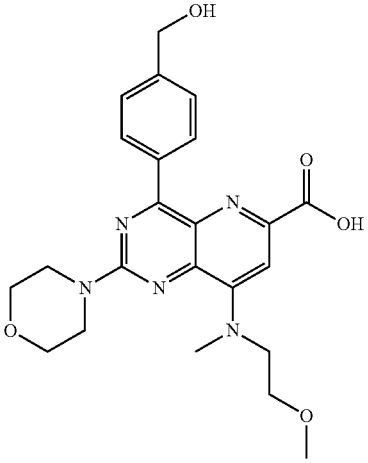 [SMILES: COCCN(C)c1cc(C(=O)O)nc2c(-c3ccc(CO)cc3)nc(N3CCOCC3)nc12] |
| 23 | 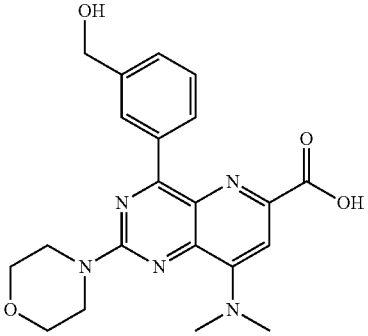 [SMILES: CN(C)c1cc(C(=O)O)nc2c(-c3cccc(CO)c3)nc(N3CCOCC3)nc12] |
| 24 | 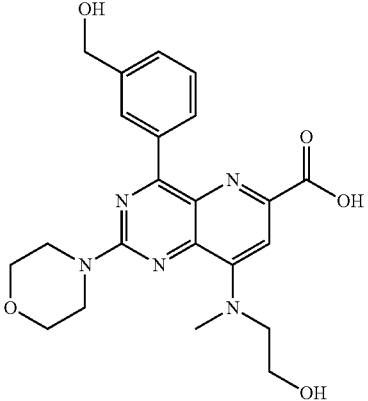 [SMILES: CN(CCO)c1cc(C(=O)O)nc2c(-c3cccc(CO)c3)nc(N3CCOCC3)nc12] |
| 25 | 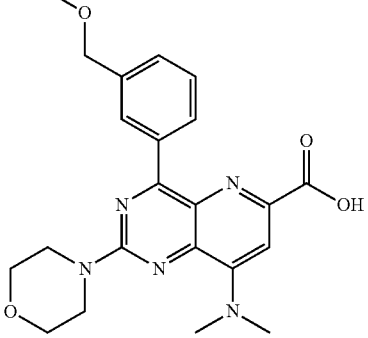 |
| Ex. No | Structures |
|---|---|
| 26 | 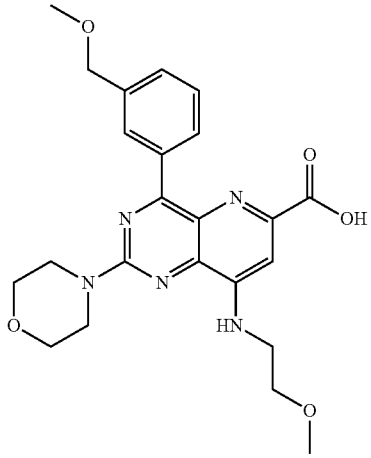 [SMILES: COCCNc1cc(C(=O)O)nc2c(-c3cccc(COC)c3)nc(N3CCOCC3)nc12] |
| 27 | 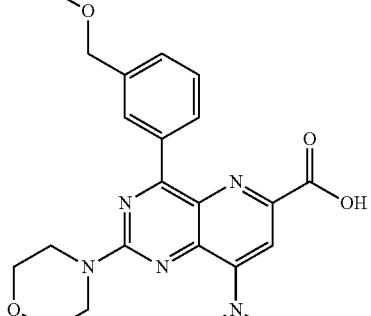 |
| 28 | 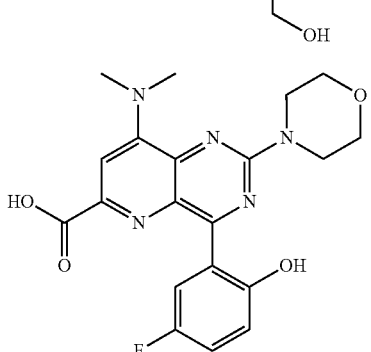 |
| 29 |  |

| Ex. No | Structures |
|---|---|
| 30 | (chemical structure) |
| 31 | (chemical structure) |
| 32 | (chemical structure) |
| 33 | (chemical structure) |
| 34 | (chemical structure) |
| 35 | (chemical structure) |
| 36 | (chemical structure) |
| 37 | (chemical structure) |

-continued

| Ex. No | Structures |
|--------|------------|
| 38 | 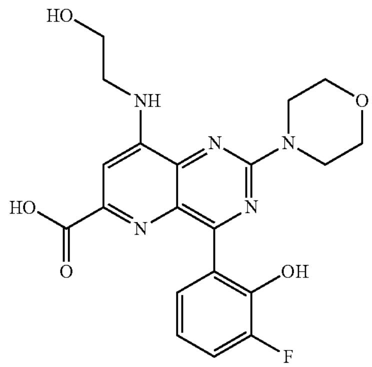 [SMILES: O=C(O)c1cc(NCCO)c2nc(N3CCOCC3)nc(-c3cccc(F)c3O)c2n1] |
| 39 | 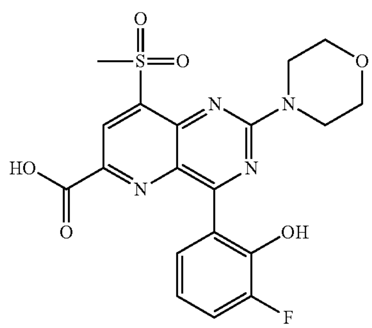 [SMILES: CS(=O)(=O)c1cc(C(=O)O)nc2c(-c3cccc(F)c3O)nc(N3CCOCC3)nc12] |
| 40 | 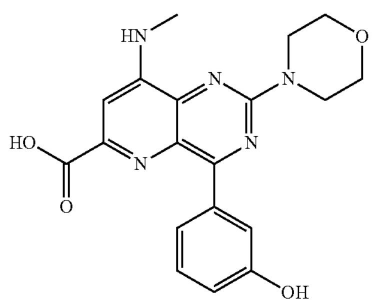 [SMILES: CNc1cc(C(=O)O)nc2c(-c3cccc(O)c3)nc(N3CCOCC3)nc12] |
| 41 | 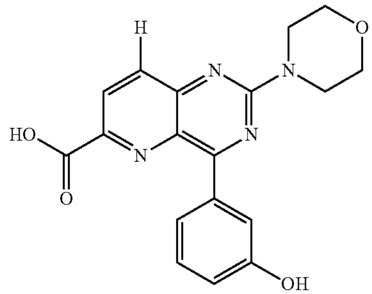 [SMILES: O=C(O)c1ccc2nc(N3CCOCC3)nc(-c3cccc(O)c3)c2n1] |
| 42 | 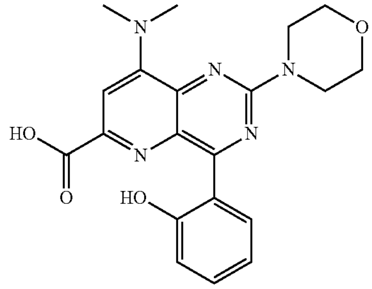 [SMILES: CN(C)c1cc(C(=O)O)nc2c(-c3ccccc3O)nc(N3CCOCC3)nc12] |

-continued

| Ex. No | Structures |
|--------|------------|
| 43 | 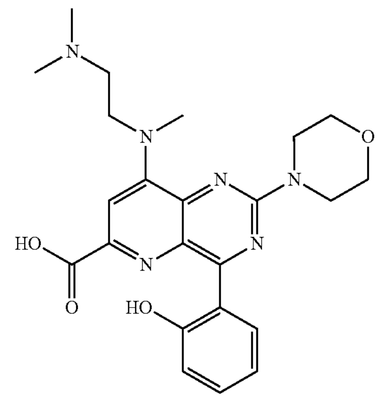 [SMILES: CN(C)CCN(C)c1cc(C(=O)O)nc2c(-c3ccccc3O)nc(N3CCOCC3)nc12] |
| 44 | 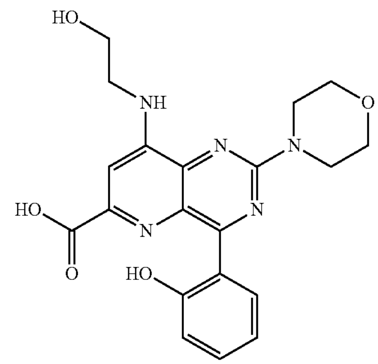 [SMILES: O=C(O)c1cc(NCCO)c2nc(N3CCOCC3)nc(-c3ccccc3O)c2n1] |
| 45 | 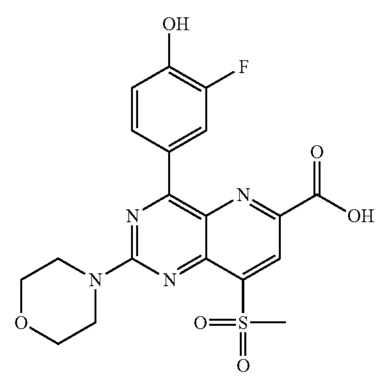 [SMILES: CS(=O)(=O)c1cc(C(=O)O)nc2c(-c3ccc(O)c(F)c3)nc(N3CCOCC3)nc12] |
| 46 | 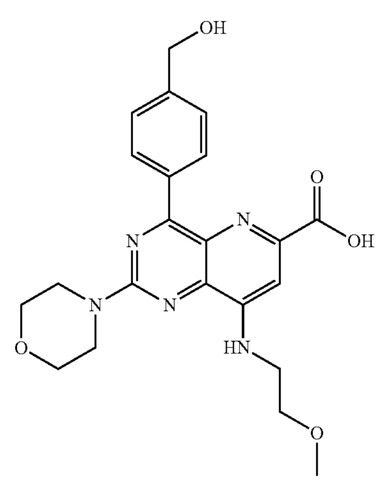 [SMILES: COCCNc1cc(C(=O)O)nc2c(-c3ccc(CO)cc3)nc(N3CCOCC3)nc12] |

-continued
| Ex. No | Structures |
|---|---|
| 47 | 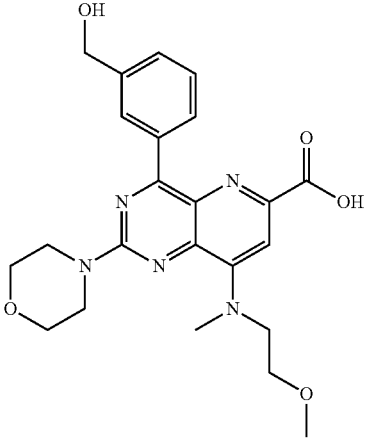 [SMILES: COCCN(C)c1cc(C(=O)O)nc2c(-c3cccc(CO)c3)nc(N3CCOCC3)nc12] |
| 48 | 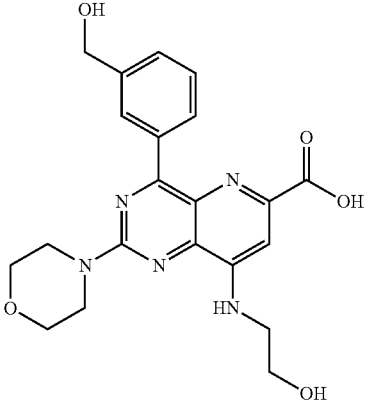 [SMILES: O=C(O)c1cc(NCCO)c2nc(N3CCOCC3)nc(-c3cccc(CO)c3)c2n1] |
| 49 | 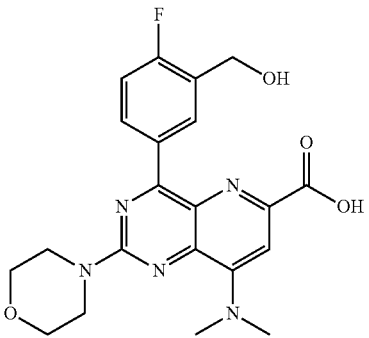 [SMILES: CN(C)c1cc(C(=O)O)nc2c(-c3ccc(F)c(CO)c3)nc(N3CCOCC3)nc12] |
| 50 | 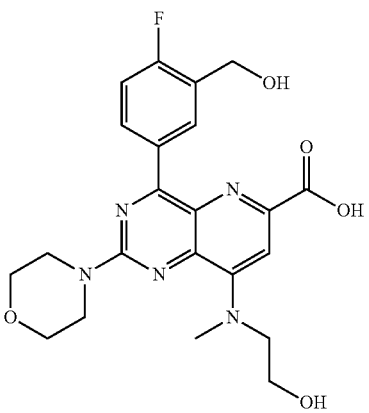 [SMILES: CN(CCO)c1cc(C(=O)O)nc2c(-c3ccc(F)c(CO)c3)nc(N3CCOCC3)nc12] |
-continued
| Ex. No | Structures |
|---|---|
| 51 | 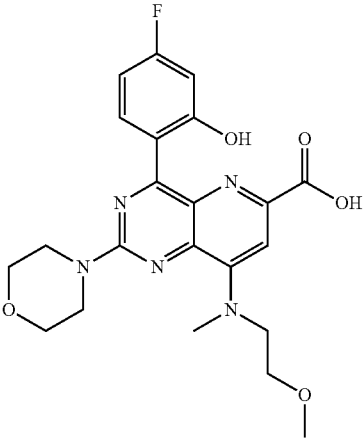 [SMILES: COCCN(C)c1cc(C(=O)O)nc2c(-c3ccc(F)cc3O)nc(N3CCOCC3)nc12] |
| 52 | 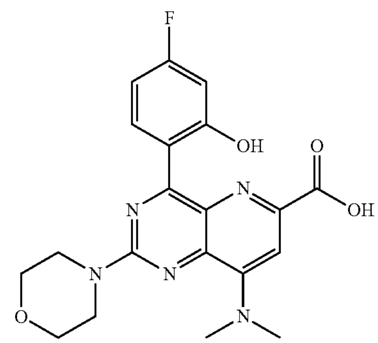 [SMILES: CN(C)c1cc(C(=O)O)nc2c(-c3ccc(F)cc3O)nc(N3CCOCC3)nc12] |
| 53 | 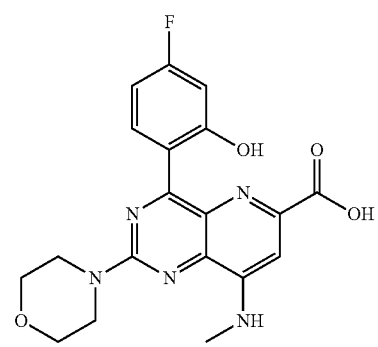 [SMILES: CNc1cc(C(=O)O)nc2c(-c3ccc(F)cc3O)nc(N3CCOCC3)nc12] |
| 54 | 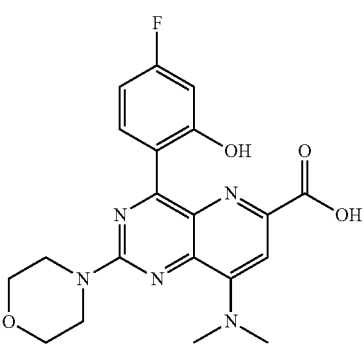 |

| Ex. No | Structures |
|---|---|
| 55 | (structure) |
| 56 | (structure) |
| 57 | (structure) |
| 58 | (structure) |
| 59 | (structure) |
| 60 | (structure) |
| 61 | (structure) |
| 62 | (structure) |

-continued

| Ex. No | Structures |
|---|---|
| 63 | 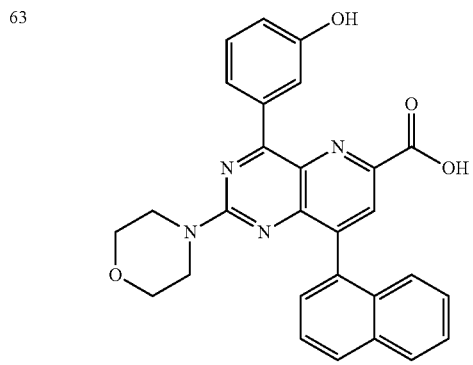 |
| 64 | 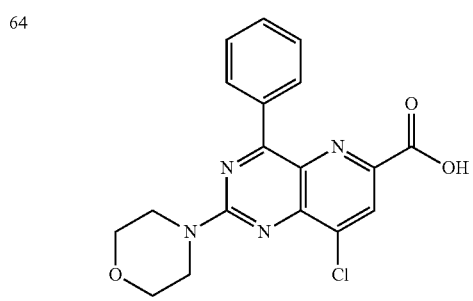 |
| 65 | 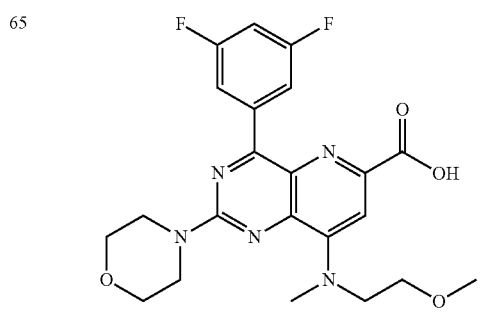 |
| 66 | 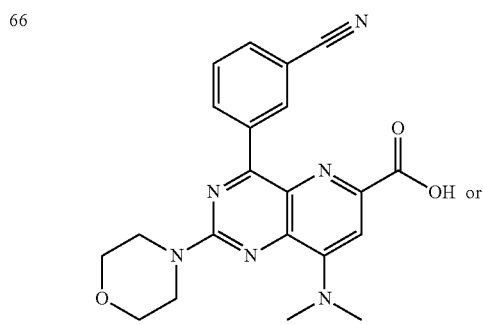 |

-continued

| Ex. No | Structures |
|---|---|
| 67 | 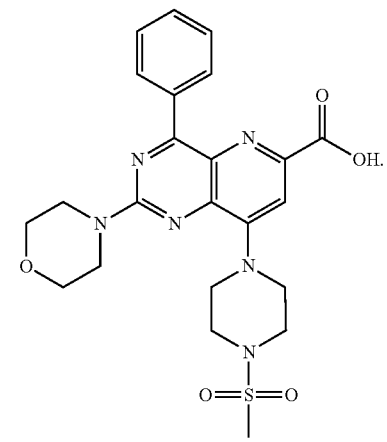 [SMILES: CS(=O)(=O)N1CCN(c2cc(C(=O)O)nc3c(-c4ccccc4)nc(N4CCOCC4)nc23)CC1] |

6. A pharmaceutical composition comprising at least one of the compounds of Formula (I) according to claim 1.

7. A process for producing compounds of Formula (I) comprising the reaction of intermediate M,

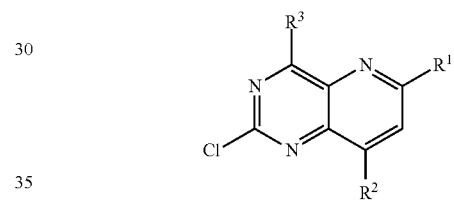

wherein $R^1$ is $CO_2(C_1$-$C_8)$alkyl or H, $R^2$ is Hal or H, and $R^3$ is SA, Ar or Het, with the amine (VII)

wherein E and $R^4$ are as defined in claim 1.

8. A process for producing compounds of Formula (I) comprising the reaction of morpholine with intermediate M,

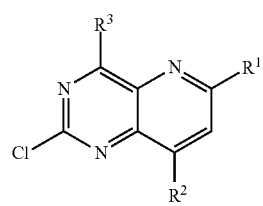

wherein $R^1$ is $CO_2(C_1$-$C_8)$alkyl or H, $R^2$ is Hal or H, and $R^3$ is SA, Ar, or Het.

* * * * *

UNITED STATES PATENT AND TRADEMARK OFFICE
CERTIFICATE OF CORRECTION

PATENT NO. : 8,609,666 B2  Page 1 of 1
APPLICATION NO. : 13/147449
DATED : December 17, 2013
INVENTOR(S) : Cyril Montagne et al.

It is certified that error appears in the above-identified patent and that said Letters Patent is hereby corrected as shown below:

In the Specification

Column 7,
Lines 5-6, "–$CH_2$–OA;" should read -- –$CH_2)_p$–OA;--.

Column 8,
Line 66, "R and R'," should read --R' and R",--.

Column 9,
Line 1, "foun a" should read --form a--.
Line 55, "$C_1$ or $CF_3$" should read --Cl or $CF_3$--.

Column 70,
Line 44, "[1,2-d]" should read --[3,2-*d*]--.

In the Claims

Column 128,
Line 6, "–$N(H)_{1-q}A_qSOA$," should read --$N(H)_{1-q}A_qSOA$,--.

Signed and Sealed this
Thirty-first Day of March, 2015

Michelle K. Lee
*Director of the United States Patent and Trademark Office*